United States Patent
Pfleger et al.

(10) Patent No.: US 10,844,410 B2
(45) Date of Patent: Nov. 24, 2020

(54) MUTANT THIOESTERASES

(71) Applicant: WISCONSIN ALUMNI RESEARCH FOUNDATION, Madison, WI (US)

(72) Inventors: Brian F. Pfleger, Madison, WI (US); Nestor Hernandez-Lozada, Madison, WI (US); Rung-Yi Lai, Changhua (TW)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/357,635

(22) Filed: Mar. 19, 2019

(65) Prior Publication Data

US 2019/0284588 A1 Sep. 19, 2019

Related U.S. Application Data

(60) Provisional application No. 62/644,954, filed on Mar. 19, 2018.

(51) Int. Cl.
| | |
|---|---|
| *C12N 9/16* | (2006.01) |
| *C12N 15/52* | (2006.01) |
| *C12N 15/00* | (2006.01) |
| *C12P 7/64* | (2006.01) |
| *C12N 15/70* | (2006.01) |

(52) U.S. Cl.
CPC ............. *C12P 7/6409* (2013.01); *C12N 9/16* (2013.01); *C12N 15/52* (2013.01); *C12N 15/70* (2013.01); *C12Y 301/02* (2013.01)

(58) Field of Classification Search
CPC ........... C12N 9/16; C12N 15/52; C12N 15/00
See application file for complete search history.

(56) References Cited

U.S. PATENT DOCUMENTS

| 9,587,231 B2 | 3/2017 | Hom et al. |
| 2016/0046914 A1 | 2/2016 | Hom et al. |

FOREIGN PATENT DOCUMENTS

| WO | WO 2008/147781 A2 | 12/2008 |
| WO | WO 2009/085278 A1 | 7/2009 |

OTHER PUBLICATIONS

Mittendorf et al., UniProt Database, accession No. Q9SMI9, May 2000.*
Agnew, D. E., Stevermer, A. K., Youngquist, J. T. & Pfleger, B. F. Engineering *Escherichia coli* for production of $C_{12}$-$C_{14}$ polyhydroxyalkanoate from glucose. *Metab. Eng.* 14, 705-13 (2012).
Amann, E., Ochs, B. & Abel, K. J. Tightly regulated tac promoter vectors useful for the expression of unfused and fused proteins in *Escherichia coli. Gene* 69, 301-315 (1988).
Beld, J., Finzel, K. & Burkart, M. D. Versatility of acyl-acyl carrier protein synthetases. *Chem. Biol.* 21, 1293-1299 (2014).
Benning, C. Mechanisms of lipid transport involved in organelle biogenesis in plant cells. *Annu. Rev. Cell Dev. Biol.* 25, 71-91 (2009).
Biermann, U. et al. Oils and fats as renewable raw materials in chemistry. *Angew. Chemie—Int. Ed.* 50, 3854-3871 (2011).
Cantu, D. C., Chen, Y., Lemons, M. L. & Reilly, P. J. Thyme: a database for thioester-active enzymes. *Nucleic Acids Res.* 39, D342-6 (2011).
Choi Y J & Lee S Y (2013) "Microbial production of short-chain alkanes," *Nature* 502(7472):571-574.
Cho, H. & Cronan, J. E. Defective export of a periplasmic enzyme disrupts regulation of fatty acid synthesis. *J. Biol. Chem.* 270, 4216-9 (1995).
Cronan JE, Zhao X, Jiang Y. Function, attachment and synthesis of lipoic acid in *Escherichia coli. Adv Microb Physiol.* 2005;50:103-46.
Datsenko, K. A. & Wanner, B. L. One-step inactivation of chromosomal genes in *Escherichia coli* K-12 using PCR products. *Proc. Natl. Acad. Sci. U. S. A.* 97, 6640-6645 (2000).
Dehesh, K., Edwards, P., Hayes, T., Cranmer, A. M. & Fillatti, J. Two novel thioesterases are key determinants of the bimodal distribution of acyl chain length of Cuphea palustris seed oil. *Plant Physiol.* 110, 203-210 (1996).
Devereux et al., A comprehensive set of sequence analysis programs for the VAX, *Nucl. Acid Res.,* 12:387-395, 1984.
Dormann, Voelker, & Ohlrogge (1995) "Cloning and Expression in *Escherichia coli* of a Novel Thioesterase from *Arabidopsis-thaliana* Specific for Long-Chain Acyl-Acyl Carrier Proteins," *Arch Biochem Biophys* 316(1):612-618.
Feng, Y. et al. Structural Insight into Acyl-ACP Thioesterase toward Substrate Specificity Design. *ACS Chem. Biol.* 12, 2830-2836 (2017).
Ferrari et al., Genetics, in Hardwood et al, (eds.), *Bacillus,* Plenum Publishing Corp., pp. 57-72, 1989 (Book).
Gibson, D. G. et al. Enzymatic assembly of DNA molecules up to several hundred kilobases. *Nat. Methods* 6, 343-5 (2009).
Graham, S. A., Hirsinger, F. & Robbelen, G. Fatty Acids of Cuphea (Lythraceae) Seed Lipids and Their Systematic Significance. *Am. J. Bot.* 68, 908 (1981).
Grisewood, M. J. et al. Computational Redesign of Acyl-ACP Thioesterase with Improved Selectivity toward Medium-Chain-Length Fatty Acids. *ACS Catal.* 3837-3849 (2017). doi:10.1021/acscatal.7b00408.
Guerot-Fleury, Antibiotic-resistance cassettes for *Bacillus subtillis, Gene,* 167:335-337, 1995.
Guzman, L.-M., Belin, D., Carson, M. J. & Beckwith, J. Tight Regulation, Modulation, and High-Level Expression by Vectors Containing the Arabinose P BAD Promoter. *J. Bacteriol.* 177, 4121-4130 (1995).
Hernández Lozada NJ, Lai RY, Simmons TR, Thomas KA, Chowdhury R, Maranas CD, Pfleger BF. Highly Active C(8)-Acyl-ACP Thioesterase Variant Isolated by a Synthetic Selection Strategy. *ACS Synth Biol.* Sep. 21, 2018;7(9):2205-2215.

(Continued)

*Primary Examiner* — Maryam Monshipouri
(74) *Attorney, Agent, or Firm* — Daniel A. Blasiole; DeWitt LLP

(57) ABSTRACT

Mutant thioesterases having enhanced medium chain substrate activity, polynucleotides encoding and configured to express the mutant thioesterases in a transformed host cell, host cells transformed to contain the polynucleotides, and methods of using same.

24 Claims, 21 Drawing Sheets
(20 of 21 Drawing Sheet(s) Filed in Color)
Specification includes a Sequence Listing.

(56) References Cited

OTHER PUBLICATIONS

Jing, F. et al. Phylogenetic and experimental characterization of an acyl-ACP thioesterase family reveals significant diversity in enzymatic specificity and activity. *BMC Biochem.* 12, 44 (2011).

Jing, F., Zhao, L., Yandeau-Nelson, M. D. & Nikolau, B. J. Two distinct domains contribute to the substrate acyl chain length selectivity of plant acyl-ACP thioesterase. *Nat. Commun.* 9, 860 (2018).

Kim, S., Clomburg, J. M. & Gonzalez, R. Synthesis of medium-chain length (C6-C10) fuels and chemicals via β-oxidation reversal in *Escherichia coli. J. Ind. Microbiol. Biotechnol.* 42, 465-475 (2015).

Larkin M. A., et al., CLUSTALW2, ClustalW and ClustalX version 2, *Bioinformatics* 23(21): 2947-2948, 2007.

Lee SK, Chou H, Ham TS, Lee TS, & Keasling JD (2008) "Metabolic engineering of microorganisms for biofuels production: from bugs to synthetic biology to fuels," *Curr Opin Biotech* 19(6):556-563.

Lennen, R. M., Braden, D. J., West, R. M., Dumesic, J. A. & Pfleger, B. F. A process for microbial hydrocarbon synthesis: Overproduction of fatty acids in *Escherichia coli* and catalytic conversion to alkanes. *Biotechnol. Bioeng.* 106, 193-202 (2010).

Lennen, R. M. & Pfleger, B. F. Engineering *Escherichia coli* to synthesize free fatty acids. *Trends Biotechnol.* 30, 659-667 (2012).

Lennen, R. M. & Pfleger, B. F. Microbial production of fatty acid-derived fuels and chemicals. *Curr. Opin. Biotechnol.* 24, 1044-1053 (2013).

Lennen, R. M. & Pfleger, B. F. Modulating Membrane Composition Alters Free Fatty Acid Tolerance in *Escherichia coli. PLoS One* 8, e54031 (2013).

Li, Y. et al. Metabolic engineering of *Escherichia coli* using CRISPR-Cas9 meditated genome editing. *Metab. Eng.* 31, 13-21 (2015).

Lo, Lin, Shaw, & Liaw (2005) "Substrate Specificities of *Escherichia coli* Thioesterase I/Protease I/Lysophospholipase L1 Are Governed by Its Switch Loop Movement," *Biochemistry* 44(6):1971-1979.

Lu X, et al. (2008) "Overproduction of free fatty acids in *E. coli:* implications for biodiesel production," *Metabolic Engineering* 10(6):333-339.

Lu, Z., Wang, Q., Jiang, S., Zhang, G. & Ma, Y. Truncation of the unique N-terminal domain improved the thermos-stability and specific activity of alkaline α-amylase Amy703. *Sci. Rep.* 6, 1-10 (2016).

Mendonça, L. M. F. & Marana, S. R. Single mutations outside the active site affect the substrate specificity in a β-glycosidase. *Biochim. Biophys. Acta—Proteins Proteomics* 1814, 1616-1623 (2011).

Muscle: a multiple sequence alignment method with reduced time and space complexity, *BMC Bioinformatics* 5:113, 2004.

Mukherjee, K., Bhattacharyya, S. & Peralta-Yahya, P. GPCR-Based Chemical Biosensors for Medium-Chain Fatty Acids. *ACS Synth. Biol.* 4, 1261-1269 (2015).

Needleman and Wunsch, A General Method Applicable to the Search for Similarities in the Amino Acid Sequence of Two Proteins, *J. Mol. Biol.,* 48:443, 1970.

Neidhardt, F. C., Bloch, P. L. & Smith, D. F. Culture Medium for Enterobacteria. *J. Bacteriol.* 119, 736-747 (1974).

Notredame et al., T-Coffee: A novel method for multiple sequence alignments, *Journal of Molecular Biology* 302: 205-217, 2000.

Palmeros et al., A family of removable cassettes designed to obtain antibiotic-resistance-free genomic modifications of *Escherichia coli* and other bacteria, *Gene,* 247:255-264, 2000.

Pantazes, R. J., Grisewood, M. J., Li, T., Gifford, N. P. & Maranas, C. D. The Iterative Protein Redesign and Optimization (IPRO) suite of programs. *J. Comput. Chem.* 36, 251-263 (2015).

Pearson and Lipman, Improved tools for biological sequence comparison, *Proc. Natl. Acad. Sci. USA* 85:2444, 1988.

Pfleger, B. F., Gossing, M. & Nielsen, J. Metabolic engineering strategies for microbial synthesis of oleochemicals. *Metab. Eng.* 29, 1-11 (2015).

Rodriguez GM, Tashiro Y, Atsumi S. Expanding ester biosynthesis in *Escherichia coli. Nat Chem Biol.* Apr. 2014;10(4):259-65.

Royce, L. A., Liu, P., Stebbins, M. J., Hanson, B. C. & Jarboe, L. R. The damaging effects of short chain fatty acids on *Escherichia coli* membranes. *Appl. Microbiol. Biotechnol.* 97, 8317-27 (2013).

Royce, L. A. et al. Evolution for exogenous octanoic acid tolerance improves carboxylic acid production and membrane integrity. *Metab. Eng.* 1-9 (2015). doi:10.1016/j.ymben.2015.03.014.

Rupilius, W. & Ahmad, S. Palm oil and palm kernel oil as raw materials for basic oleochemicals and biodiesel. *Eur. J. Lipid Sci. Technol.* 109, 433-439 (2007).

Salimon, J., Salih, N. & Yousif, E. Industrial development and applications of plant oils and their biobased oleochemicals. *Arab. J. Chem.* 5, 135-145 (2012).

Sarria, S., Kruyer, N. S. & Peralta-Yahya, P. Microbial synthesis of medium-chain chemicals from renewables. *Nat. Biotechnol.* 35, 1158-1166 (2017).

Smith and Waterman, Comparison of Biosequences, *Adv. Appl. Math.,* 2:482, 1981.

Steen EJ, et al. (2010) "Microbial production of fatty-acid-derived fuels and chemicals from plant biomass," *Nature,* 463(7280):559-U182.

Thompson J. D., Higgins D. G., Gibson T. J., Clustal W: improving the sensitivity of progressive multiple sequence alignment through sequence weighting, position-specific gap penalties and weight matrix choice, *Nucleic Acids Research* 22: 4673-4680, 1994.

Torella, J. P. et al. Tailored fatty acid synthesis via dynamic control of fatty acid elongation. *Proc. Natl. Acad. Sci. U. S. A.* 110, 11290-5 (2013).

Trieu-Cuot P, Courvalin P. Nucleotide sequence of the *Streptococcus faecalis* plasmid gene encoding the 3'5"-aminoglycoside phosphotransferase type III. *Gene.* Sep. 1983;23(3):331-41.

Voelker, T. A. & Davies, H. M. Alteration of the specificity and regulation of fatty acid synthesis of *Escherichia coli* by expression of a plant medium-chain acyl-acyl carrier protein thioesterase. *J. Bacteriol.* 176, 7320-7 (1994).

Robert M. Willis, Bradley D. Wahlen, Lance C. Seefeldt, and Brett M. Barney. Characterization of a Fatty Acyl-CoA Reductase from Marinobacter aquaeolei VT8: A Bacterial Enzyme Catalyzing the Reduction of Fatty Acyl-CoA to Fatty Alcohol. *Biochemistry* 2011 50 (48), 10550-10558.

Youngquist, J. T., Rose, J. P. & Pfleger, B. F. Free fatty acid production in *Escherichia coli* under phosphate-limited conditions. *Appl. Microbiol. Biotechnol.* 97, 5149-5159 (2013).

Youngquist, J. T. et al. Production of medium chain length fatty alcohols from glucose in *Escherichia coli. Metab. Eng.* 20, 177-186 (2013).

Zhang X, et al. (2011) "Efficient free fatty acid production in *Escherichia coli* using plant acyl-ACP thioesterases," *Metabolic engineering* 13(6):713-722.

Zhang, F. et al. Enhancing fatty acid production by the expression of the regulatory transcription factor FadR. *Metab. Eng.* 14, 653-60 (2012).

Zhang, F., Carothers, J. M. & Keasling, J. D. Design of a dynamic sensor-regulator system for production of chemicals and fuels derived from fatty acids. *Nat. Biotechnol.* 30, 354-359 (2012).

Zhao, X., Miller, J. R., Jiang, Y., Marletta, M. A. & Cronan, J. E. Assembly of the Covalent Linkage between Lipoic Acid and Its Cognate Enzymes. *Chem. Biol.* 10, 1293-1302 (2003).

* cited by examiner

↓CpFatB1

MVAAAASSACFPVPSPGASPKPGKLGNWSSSLSPSLKPKSIPNGGFQVKANASAHPKANGSAVTLK

↓CpFatB1.2　　　　　　　　↓CpFatB1.3

SGSLNTQEDTLSSSPPPRAFFNQLPDWSMLLTAITTVFVAPEKRWTMFDRKSKRPNMLMDSFGLER

↓CpFatB1.4

VVQDGLVFRQSFSIRSYEICADRTASIETVMNHVQETSLNQCKSIGLLDDGFGRSPEMCKRDLIWV
VTRMKIMVNRYPTWGDTIEVSTWLSQSGKIGMGRDWLISDCNTGEILVRATSVYAMMNQKTRRFSK
LPHEVRQEFAPHFLDSPPAIEDNDGKLQKFDVKTGDSIRKGLTPGWYDLDVNQHVSNVKYIGWILE
SMPTEVLETQELCSLTLEYRRECGRDSVLESVTSMDPSKVGDRFQYRHLLRLEDGADIMKGRTEWR
PKNAGTNGAISTGKT* (SEQ ID NO:2)

FIG. 3A

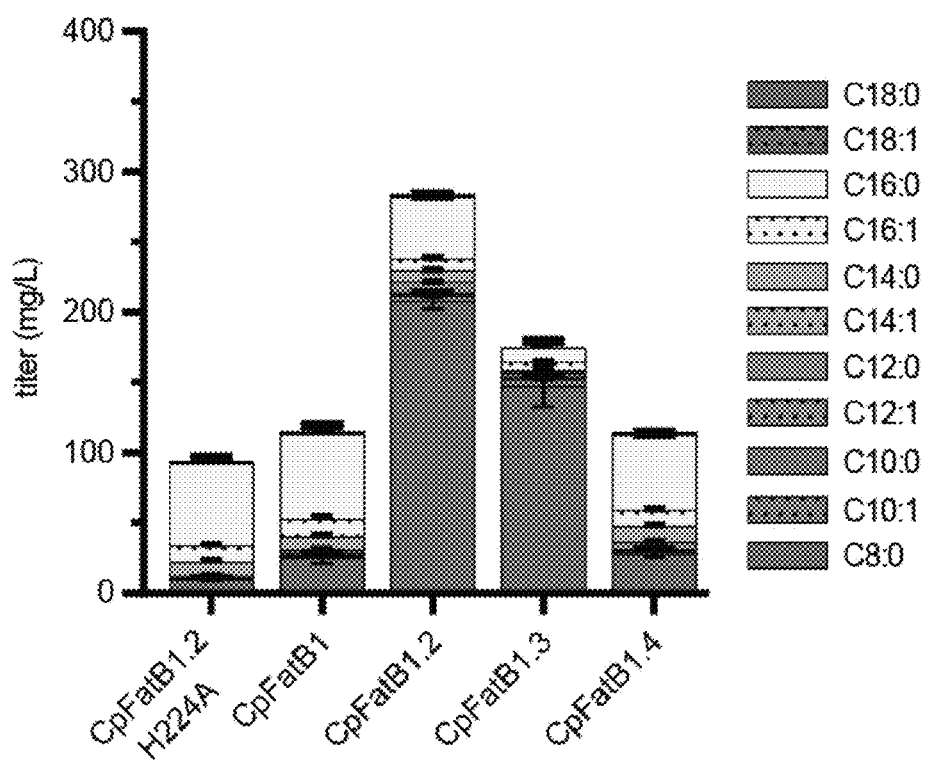

FIG. 3B

Random mutagenesis
CpFatB1.2 Coding sequence
    Mutant 1    X  X          X
    Mutant 2    X                      X
    Mutant n    X        X    X
Minimal media plates
 0.2% glucose + 20 µM IPTG

| plasmid | Media + 50 µM C8:0 | Media No C8:0 |
|---|---|---|
| Empty plasmid | 2 days | No growth |
| CpFatB1.2 | 2 days | 4 days |
| CpFatB1.2 variants | 2 days | 3 days |

| Mutant | Residue changes |
|---|---|
| CpFatB1.2 | n/a |
| CpFatB1.2-M1 | A59S, K296R |
| CpFatB1.2-M2 | M29T, T117S, Q163L |
| CpFatB1.2-M3 | A59S, K296R |
| CpFatB1.2-M4 | ΔA$_{54}$ (new start codon at M19), N28S, I65M |
| CpFatB1.2-M5 | W17R, T204S |
| CpFatB1.2-M6 | L251M, L265I, |
| CpFatB1.2-M7 | n/a |
| CpFatB1.2-M8 | K15E, S207T |
| CpFatB1.2-M9 | R261S |
| CpFatB1.2-M10 | n/a |

```
                    1          10         20         30         40         50         60         70         80
                    +----+----+----+----+----+----+----+----+----+----+----+----+----+----+----+----+----+----+
CpFatB1.2           MLLTAITTVFVAPEKRWTMFDRKSKRPNMLMDSFGLERVVQDGLVFRQSFSIRSYEICADRTASIETVMNHVQETSLNQCKSIGL...
CpFatB1.2-M4        YAAHRDYHRVRCAGKRWTMFDRKSKRPS*LL*DSFGLERVVQDGLVFRQSFSIRSYEICADRTASIETV*NHVQETSLNQCKSIGL...
CpFatB1.2-M4-287    **************MFDRKSKRPS*LL*DSFGLERVVQDGLVFRQSFSIRSYEICADRTASmETVMNHVQETSLNQCKSIGL...
CpFatB1.2-M4-288    ******************MLMDSFGLERVVQDGLVFRQSFSIRSYEICADRTASmETVMNHVQETSLNQCKSIGL...
CpFatB1.2-M4-289    ********************MDSFGLERVVQDGLVFRQSFSIRSYEICADRTASmETVMNHVQETSLNQCKSIGL...
CpFatB1.2-M4-290    **********************************************ETVMNHVQETSLNQCKSIGL...
CpFatB1.2-M4-291    ******************************************************mETVMNHVQETSLNQCKSIGL...

CpFatB1.2           ... (Positions 1-85 of SEQ ID NO:4)
CpFatB1.2-M4        ... (Positions 1-85 of SEQ ID NO:12)
CpFatB1.2-M4-287    ... (Positions 1-67 of SEQ ID NO:14)
CpFatB1.2-M4-288    ... (Positions 11-67 of SEQ ID NO:14)
CpFatB1.2-M4-289    ... (Positions 13-67 of SEQ ID NO:14)
CpFatB1.2-M4-290    ... (Positions 47-67 of SEQ ID NO:14)
CpFatB1.2-M4-291    ... (Positions 51-67 of SEQ ID NO:14)
```

FIG. 10A

| Mutant | kcat (min⁻¹) | Km (µM) | kcat/Km (µM⁻¹ min⁻¹) |
|---|---|---|---|
| CpFatB1.2 | 68.6 ± 2.1 | 5.92 ± 1.1 | 11.6 ± 2.2 |
| CpFatB1.2-M4 | 1076 ± 21 | 36.8 ± 2.3 | 29.2 ± 1.9 |
| TesA-R3.M4 | 1028 ± 66 | 606 ± 56 | 1.70 ± 0.2 |

SEQUENCE LISTING

<160> NUMBER OF SEQ ID NOS: 18

<210> SEQ ID NO 1
<211> LENGTH: 1236
<212> TYPE: DNA
<213> ORGANISM: Cuphea palustris

<400> SEQUENCE: 1

```
atggtagctg ctgcggcgag tagcgcttgc tttccagtgc cgtctccggg cgcaagcccg      60
aaaccgggga aactgggtaa ctggagctct tcgctgagtc cgagcctgaa accgaaatct     120
attccgaacg gcggctttca ggttaaagca aacgcgtccg cacatccgaa ggcaaacggc     180
tccgcggtta ctctgaaaag cggtagcctg aacacgcagg aagacacact gtccagcagc     240
cctccgccgc gtgctttctt caaccagctg ccggactgga gcatgctgct caccgcgatt     300
accaccgtgt tcgttgcgcc ggaaaaaacgt tggactatgt tcgaccgcaa atctaaacgt     360
ccgaacatgc tgatggatag cttcggtctg aacgtgttg tccaggatgg tctggttttc     420
cgccaatcct tctccattcg tagctacgaa atctgtgcgg accgcacggc gagcatcgag     480
accgtgatga ccacgttca ggaaaccagc ctgaaccagt gtaagtccat cggcctgctg     540
gacgacggtt tcggtcgctc accggaaatg tgtaaacgcg acctgatttg ggttgtaacc     600
cgtatgaaaa ttatggtaaa ccgttatccg acctggggcg acaccattga agtctccacc     660
tggctgtccc agtccggtaa aattggcatg ggtcgcgact ggctgattag cgattgtaat     720
accggtgaaa tactggttcg tgcaacctca gtttacgcca tgatgaacca gaaaacgcgt     780
cgcttctcta aactgcccca cgaagtacgc caggagttcg cgccgcactt cttagactcc     840
ccgccggcca ttgaagacaa cgacggtaaa ctgcagaaat cgatgtgaa aaccggtgat     900
tccatccgca aggtctgac cccgggctgg tacgacctgg acgtaaacca gcacgtttcc     960
aatgtcaaat atatcggttg gatcctggaa tccatgccga ccgaagttct ggaaacccaa    1020
gaactttgca gcctgactct cgaataccgt cgcgaatgcg gtcgcgactc agtacttgag    1080
agcgtaacct ccatggaccc gtctaaagtt ggtgatcgtt ttcagtatcg tcatctgctg    1140
cgtctggaag atggtgcgga cattatgaag ggccgtaccg aatggcgtcc gaaaaacgcg    1200
ggcactaatg gtgctatctc cactgggaaa acataa                              1236
```

<210> SEQ ID NO 2
<211> LENGTH: 411
<212> TYPE: PRT
<213> ORGANISM: Cuphea palustris

<400> SEQUENCE: 2

Met Val Ala Ala Ala Ser Ser Ala Cys Phe Pro Val Pro Ser Pro
1               5                   10                  15

Gly Ala Ser Pro Lys Pro Gly Lys Leu Gly Asn Trp Ser Ser Ser Leu
            20                  25                  30

Ser Pro Ser Leu Lys Pro Lys Ser Ile Pro Asn Gly Gly Phe Gln Val
        35                  40                  45

Lys Ala Asn Ala Ser Ala His Pro Lys Ala Asn Gly Ser Ala Val Thr
    50                  55                  60

Leu Lys Ser Gly Ser Leu Asn Thr Gln Glu Asp Thr Leu Ser Ser Ser
65                  70                  75                  80

Pro Pro Pro Arg Ala Phe Phe Asn Gln Leu Pro Asp Trp Ser Met Leu
                85                  90                  95

Leu Thr Ala Ile Thr Thr Val Phe Val Ala Pro Glu Lys Arg Trp Thr
            100                 105                 110

Met Phe Asp Arg Lys Ser Lys Arg Pro Asn Met Leu Met Asp Ser Phe
        115                 120                 125

Gly Leu Glu Arg Val Val Gln Asp Gly Leu Val Phe Arg Gln Ser Phe
    130                 135                 140

Ser Ile Arg Ser Tyr Glu Ile Cys Ala Asp Arg Thr Ala Ser Ile Glu
145                 150                 155                 160

Thr Val Met Asn His Val Gln Glu Thr Ser Leu Asn Gln Cys Lys Ser
                165                 170                 175

Ile Gly Leu Leu Asp Asp Gly Phe Gly Arg Ser Pro Glu Met Cys Lys
            180                 185                 190

Arg Asp Leu Ile Trp Val Val Thr Arg Met Lys Ile Met Val Asn Arg
        195                 200                 205

Tyr Pro Thr Trp Gly Asp Thr Ile Glu Val Ser Thr Trp Leu Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Val Tyr Ala Met Met Asn
                245                 250                 255

Gln Lys Thr Arg Arg Phe Ser Lys Leu Pro His Glu Val Arg Gln Glu
            260                 265                 270

Phe Ala Pro His Phe Leu Asp Ser Pro Ala Ile Glu Asp Asn Asp
        275                 280                 285

Gly Lys Leu Gln Lys Phe Asp Val Lys Thr Gly Asp Ser Ile Arg Lys
    290                 295                 300

Gly Leu Thr Pro Gly Trp Tyr Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Asp Ser Val Leu Glu Ser Val Thr Ser Met Asp Pro Ser
        355                 360                 365

Lys Val Gly Asp Arg Phe Gln Tyr Arg His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr
                405                 410

<210> SEQ ID NO 3
<211> LENGTH: 954
<212> TYPE: DNA
<213> ORGANISM: Artificial Sequence
<220> FEATURE:
<223> OTHER INFORMATION: CpFatB1 1.2 Trucation

<400> SEQUENCE: 3
atgctgctca ccgcgattac caccgtgttc gttgcgccgg aaaaacgttg gactatgttc      60
gaccgcaaat ctaaacgtcc gaacatgctg atggatagct tcggtctgga acgtgttgtc     120
caggatggtc tggttttccg ccaatccttc tccattcgta gctacgaaat ctgtgcggac     180
cgcacggcga gcatcgagac cgtgatgaac cacgttcagg aaaccagcct gaaccagtgt     240
aagtccatcg gcctgctgga cgacggtttc ggtcgctcac cggaaatgtg taaacgcgac     300

-continued

```
ctgatttggg ttgtaacccg tatgaaaatt atggtaaacc gttatccgac ctggggcgac    360
accattgaag tctccacctg gctgtcccag tccggtaaaa ttggcatggg tcgcgactgg    420
ctgattagcg attgtaatac cggtgaaata ctggttcgtg caacctcagt ttacgccatg    480
atgaaccaga aaacgcgtcg cttctctaaa ctgccccacg aagtacgcca ggagttcgcg    540
ccgcacttct tagactcccc gccggccatt gaagacaacg acggtaaact gcagaaattc    600
gatgtgaaaa ccggtgattc catccgcaaa ggtctgaccc cgggctggta cgacctggac    660
gtaaaccagc acgtttccaa tgtcaaatat atcggttgga tcctggaatc catgccgacc    720
gaagttctgg aaacccaaga actttgcagc ctgactctcg aataccgtcg cgaatgcggt    780
cgcgactcag tacttgagag cgtaacctcc atggacccgt ctaaagttgg tgatcgtttt    840
cagtatcgtc atctgctgcg tctggaagat ggtgcggaca ttatgaaggg ccgtaccgaa    900
tggcgtccga aaacgcggg cactaatggt gctatctcca ctgggaaaac ataa           954
```

<210> SEQ ID NO 4
<211> LENGTH: 317
<212> TYPE: PRT
<213> ORGANISM: Artificial Sequence
<220> FEATURE:
<223> OTHER INFORMATION: CpFatB 1.2 Truncation

<400> SEQUENCE: 4

```
Met Leu Leu Thr Ala Ile Thr Thr Val Phe Val Ala Pro Glu Lys Arg
1               5                   10                  15

Trp Thr Met Phe Asp Arg Lys Ser Lys Arg Pro Asn Met Leu Met Asp
                20                  25                  30

Ser Phe Gly Leu Glu Arg Val Val Gln Asp Gly Leu Val Phe Arg Gln
            35                  40                  45

Ser Phe Ser Ile Arg Ser Tyr Glu Ile Cys Ala Asp Arg Thr Ala Ser
        50                  55                  60

Ile Glu Thr Val Met Asn His Val Gln Glu Thr Ser Leu Asn Gln Cys
65                  70                  75                  80

Lys Ser Ile Gly Leu Leu Asp Asp Gly Phe Gly Arg Ser Pro Glu Met
                85                  90                  95

Cys Lys Arg Asp Leu Ile Trp Val Val Thr Arg Met Lys Ile Met Val
            100                 105                 110

Asn Arg Tyr Pro Thr Trp Gly Asp Thr Ile Glu Val Ser Thr Trp Leu
        115                 120                 125

Ser Gln Ser Gly Lys Ile Gly Met Gly Arg Asp Trp Leu Ile Ser Asp
    130                 135                 140

Cys Asn Thr Gly Glu Ile Leu Val Arg Ala Thr Ser Val Tyr Ala Met
145                 150                 155                 160

Met Asn Gln Lys Thr Arg Arg Phe Ser Lys Leu Pro His Glu Val Arg
                165                 170                 175

Gln Glu Phe Ala Pro His Phe Leu Asp Ser Pro Ala Ile Glu Asp
            180                 185                 190

Asn Asp Gly Lys Leu Gln Lys Phe Asp Val Lys Thr Gly Asp Ser Ile
        195                 200                 205

Arg Lys Gly Leu Thr Pro Gly Trp Tyr Asp Leu Asp Val Asn Gln His
    210                 215                 220

Val Ser Asn Val Lys Tyr Ile Gly Trp Ile Leu Glu Ser Met Pro Thr
225                 230                 235                 240

Glu Val Leu Glu Thr Gln Glu Leu Cys Ser Leu Thr Leu Glu Tyr Arg
                245                 250                 255
```

Arg Glu Cys Gly Arg Asp Ser Val Leu Glu Ser Val Thr Ser Met Asp
            260                 265                 270

Pro Ser Lys Val Gly Asp Arg Phe Gln Tyr Arg His Leu Leu Arg Leu
        275                 280                 285

Glu Asp Gly Ala Asp Ile Met Lys Gly Arg Thr Glu Trp Arg Pro Lys
    290                 295                 300

Asn Ala Gly Thr Asn Gly Ala Ile Ser Thr Gly Lys Thr
305                 310                 315

<210> SEQ ID NO 5
<211> LENGTH: 891
<212> TYPE: DNA
<213> ORGANISM: Artificial Sequence
<220> FEATURE:
<223> OTHER INFORMATION: CpFatB 1.3 Truncation

<400> SEQUENCE: 5
atgaaatcta aacgtccgaa catgctgatg gatagcttcg gtctggaacg tgttgtccag    60
gatggtctgg ttttccgcca atccttctcc attcgtagct acgaaatctg tgcggaccgc   120
acggcgagca tcgagaccgt gatgaaccac gttcaggaaa ccagcctgaa ccagtgtaag   180
tccatcggcc tgctggacga cggtttcggt cgctcaccgg aaatgtgtaa acgcgacctg   240
atttgggttg taacccgtat gaaaattatg gtaaaccgtt atccgacctg ggcgacacc   300
attgaagtct ccacctggct gtcccagtcc ggtaaaattg catgggtcg cgactggctg   360
attagcgatt gtaataccgg tgaaatactg gttcgtgcaa cctcagttta cgccatgatg   420
aaccagaaaa cgcgtcgctt ctctaaactg ccccacgaag tacgccagga gttcgcgccg   480
cacttcttag actccccgcc ggccattgaa acaacgacg taaactgca gaaattcgat   540
gtgaaaaccg tgattccat ccgcaaaggt ctgaccccgg ctggtacga cctgacgta   600
aaccagcacg tttccaatgt caaatatatc ggttggatcc tggaatccat gccgaccgaa   660
gttctgaaa cccaagaact ttgcagcctg actctcgaat accgtcgcga atgcggtcgc   720
gactcagtac ttgagagcgt aacctccatg acccgtcta agttggtga tcgttttcag   780
tatcgtcatc tgctgcgtct ggaagatggt gcggacatta tgaagggccg taccgaatgg   840
cgtccgaaaa acgcgggcac taatggtgct atctccactg gaaaacata a             891

<210> SEQ ID NO 6
<211> LENGTH: 296
<212> TYPE: PRT
<213> ORGANISM: Artificial Sequence
<220> FEATURE:
<223> OTHER INFORMATION: CpFatB 1.3 Truncation

<400> SEQUENCE: 6

Met Lys Ser Lys Arg Pro Asn Met Leu Met Asp Ser Phe Gly Leu Glu
1               5                   10                  15

Arg Val Val Gln Asp Gly Leu Val Phe Arg Gln Ser Phe Ser Ile Arg
            20                  25                  30

Ser Tyr Glu Ile Cys Ala Asp Arg Thr Ala Ser Ile Glu Thr Val Met
        35                  40                  45

Asn His Val Gln Glu Thr Ser Leu Asn Gln Cys Lys Ser Ile Gly Leu
    50                  55                  60

Leu Asp Asp Gly Phe Gly Arg Ser Pro Glu Met Cys Lys Arg Asp Leu
65                  70                  75                  80

Ile Trp Val Val Thr Arg Met Lys Ile Met Val Asn Arg Tyr Pro Thr
                85                  90                  95

Trp Gly Asp Thr Ile Glu Val Ser Thr Trp Leu Ser Gln Ser Gly Lys
        100                 105                 110

Ile Gly Met Gly Arg Asp Trp Leu Ile Ser Asp Cys Asn Thr Gly Glu
    115                 120                 125

Ile Leu Val Arg Ala Thr Ser Val Tyr Ala Met Met Asn Gln Lys Thr
130                 135                 140

Arg Arg Phe Ser Lys Leu Pro His Glu Val Arg Gln Glu Phe Ala Pro
145                 150                 155                 160

His Phe Leu Asp Ser Pro Pro Ala Ile Glu Asp Asn Asp Gly Lys Leu
                165                 170                 175

Gln Lys Phe Asp Val Lys Thr Gly Asp Ser Ile Arg Lys Gly Leu Thr
            180                 185                 190

Pro Gly Trp Tyr Asp Leu Asp Val Asn Gln His Val Ser Asn Val Lys
        195                 200                 205

Tyr Ile Gly Trp Ile Leu Glu Ser Met Pro Thr Glu Val Leu Glu Thr
    210                 215                 220

Gln Glu Leu Cys Ser Leu Thr Leu Glu Tyr Arg Arg Glu Cys Gly Arg
225                 230                 235                 240

Asp Ser Val Leu Glu Ser Val Thr Ser Met Asp Pro Ser Lys Val Gly
                245                 250                 255

Asp Arg Phe Gln Tyr Arg His Leu Leu Arg Leu Glu Asp Gly Ala Asp
            260                 265                 270

Ile Met Lys Gly Arg Thr Glu Trp Arg Pro Lys Asn Ala Gly Thr Asn
        275                 280                 285

Gly Ala Ile Ser Thr Gly Lys Thr
        290                 295

<210> SEQ ID NO 7
<211> LENGTH: 831
<212> TYPE: DNA
<213> ORGANISM: Artificial Sequence
<220> FEATURE:
<223> OTHER INFORMATION: CpFatB 1.4 Truncation

<400> SEQUENCE: 7
atgggtctgg ttttccgcca atccttctcc attcgtagct acgaaatctg tgcggaccgc    60
acggcgagca tcgagaccgt gatgaaccac gttcaggaaa ccagcctgaa ccagtgtaag   120
tccatcggcc tgctggacga cggtttcggt cgctcaccgg aaatgtgtaa acgcgacctg   180
atttggttg taacccgtat gaaaattatg gtaaaccgtt atccgacctg ggcgacacc    240
attgaagtct ccacctggct gtcccagtcc ggtaaaattg gcatgggtcg cgactggctg   300
attagcgatt gtaataccgg tgaaatactg gttcgtgcaa cctcagttta cgccatgatg   360
aaccagaaaa cgcgtcgctt ctctaaactg ccccacgaag tacgccagga gttcgcgccg   420
cacttcttag actccccgcc ggccattgaa gacaacgacg gtaaactgca gaaattcgat   480
gtgaaaaccg gtgattccat ccgcaaaggt ctgaccccgg gctggtacga cctggacgta   540
aaccagcacg tttccaatgt caaatatatc ggttggatcc tggaatccat gccgaccgaa   600
gttctggaaa cccaagaact tgcagcctg actctcgaat accgtcgcga atgcggtcgc    660
gactcagtac ttgagagcgt aacctccatg gaccgtctca agttggtga tcgttttcag    720
tatcgtcatc tgctgcgtct ggaagatggt gcggacatta tgaagggccg taccgaatgg   780
cgtccgaaaa acgcgggcac taatggtgct atctccactg gaaaacata a            831

<210> SEQ ID NO 8
<211> LENGTH: 276
<212> TYPE: PRT
<213> ORGANISM: Artificial Sequence
<220> FEATURE:
<223> OTHER INFORMATION: CpFatB 1.4 Truncation

<400> SEQUENCE: 8

```
Met Gly Leu Val Phe Arg Gln Ser Phe Ser Ile Arg Ser Tyr Glu Ile
1               5                   10                  15

Cys Ala Asp Arg Thr Ala Ser Ile Glu Thr Val Met Asn His Val Gln
            20                  25                  30

Glu Thr Ser Leu Asn Gln Cys Lys Ser Ile Gly Leu Leu Asp Asp Gly
        35                  40                  45

Phe Gly Arg Ser Pro Glu Met Cys Lys Arg Asp Leu Ile Trp Val Val
    50                  55                  60

Thr Arg Met Lys Ile Met Val Asn Arg Tyr Pro Thr Trp Gly Asp Thr
65                  70                  75                  80

Ile Glu Val Ser Thr Trp Leu Ser Gln Ser Gly Lys Ile Gly Met Gly
                85                  90                  95

Arg Asp Trp Leu Ile Ser Asp Cys Asn Thr Gly Glu Ile Leu Val Arg
            100                 105                 110

Ala Thr Ser Val Tyr Ala Met Met Asn Gln Lys Thr Arg Arg Phe Ser
        115                 120                 125

Lys Leu Pro His Glu Val Arg Gln Glu Phe Ala Pro His Phe Leu Asp
    130                 135                 140

Ser Pro Pro Ala Ile Glu Asp Asn Asp Gly Lys Leu Gln Lys Phe Asp
145                 150                 155                 160

Val Lys Thr Gly Asp Ser Ile Arg Lys Gly Leu Thr Pro Gly Trp Tyr
                165                 170                 175

Asp Leu Asp Val Asn Gln His Val Ser Asn Val Lys Tyr Ile Gly Trp
            180                 185                 190

Ile Leu Glu Ser Met Pro Thr Glu Val Leu Glu Thr Gln Glu Leu Cys
        195                 200                 205

Ser Leu Thr Leu Glu Tyr Arg Arg Glu Cys Gly Arg Asp Ser Val Leu
    210                 215                 220

Glu Ser Val Thr Ser Met Asp Pro Ser Lys Val Gly Asp Arg Phe Gln
225                 230                 235                 240

Tyr Arg His Leu Leu Arg Leu Glu Asp Gly Ala Asp Ile Met Lys Gly
                245                 250                 255

Arg Thr Glu Trp Arg Pro Lys Asn Ala Gly Thr Asn Gly Ala Ile Ser
            260                 265                 270

Thr Gly Lys Thr
        275
```

<210> SEQ ID NO 9
<211> LENGTH: 954
<212> TYPE: DNA
<213> ORGANISM: Artificial Sequence
<220> FEATURE:
<223> OTHER INFORMATION: CpFatB 1.2 M3 Mutant

<400> SEQUENCE: 9

```
atgctgctca ccgcgattac caccgtgttc gttgcgccgg aaaaacgttg gactatgttc      60
gaccgcaaat ctaaacgtcc gaacatgctg atggatagct tcggtctgga acgtgttgtc     120
caggatggtc tggttttccg ccaatccttc tccattcgta gctacgaaat ctgttcggac     180
```

```
cgcacggcga gcatcgagac cgtgatgaac cacgttcagg aaaccagcct gaaccagtgt    240
aagtccatcg gcctgctgga cgacggtttc ggtcgctcac cggaaatgtg taaacgcgac    300
ctgatttggg ttgtaacccg tatgaaaatt atggtaaacc gttatccgac ctggggcgac    360
accattgaag tctccacctg gctgtcccag tccggtaaaa ttggcatggg tcgcgactgg    420
ctgattagcg attgtaatac cggtgaaata ctggttcgtg caacctcagt ttacgccatg    480
atgaaccaga aaacgcgtcg cttctctaaa ctgccccacg aagtacgcca ggagttcgcg    540
ccgcacttct tagactcccc gccggccatt gaagacaacg acggtaaact gcagaaattc    600
gatgtgaaaa ccggtgattc catccgcaaa ggtctgaccc cgggctggta cgacctggac    660
gtaaaccagc acgtttccaa tgtcaaatat atcggttgga tcctggaatc catgccgacc    720
gaagttctgg aaacccaaga actttgcagc ctgactctcg aataccgtcg cgaatgcggt    780
cgcgactcag tacttgagag cgtaacctcc atggacccgt ctaaagttgg tgatcgtttt    840
cagtatcgtc atctgctgcg tctggaagat ggtgcggaca ttatgagggg ccgtaccgaa    900
tggcgtccga aaacgcgggg cactaatggt gctatctcca ctgggaaaac ataa          954
```

<210> SEQ ID NO 10
<211> LENGTH: 317
<212> TYPE: PRT
<213> ORGANISM: Artificial Sequence
<220> FEATURE:
<223> OTHER INFORMATION: CpFatB1.2 M3 Mutant

<400> SEQUENCE: 10

```
Met Leu Leu Thr Ala Ile Thr Thr Val Phe Val Ala Pro Glu Lys Arg
1               5                   10                  15

Trp Thr Met Phe Asp Arg Lys Ser Lys Arg Pro Asn Met Leu Met Asp
            20                  25                  30

Ser Phe Gly Leu Glu Arg Val Val Gln Asp Gly Leu Val Phe Arg Gln
        35                  40                  45

Ser Phe Ser Ile Arg Ser Tyr Glu Ile Cys Ser Asp Arg Thr Ala Ser
    50                  55                  60

Ile Glu Thr Val Met Asn His Val Gln Glu Thr Ser Leu Asn Gln Cys
65                  70                  75                  80

Lys Ser Ile Gly Leu Leu Asp Asp Gly Phe Gly Arg Ser Pro Glu Met
                85                  90                  95

Cys Lys Arg Asp Leu Ile Trp Val Val Thr Arg Met Lys Ile Met Val
            100                 105                 110

Asn Arg Tyr Pro Thr Trp Gly Asp Thr Ile Glu Val Ser Thr Trp Leu
        115                 120                 125

Ser Gln Ser Gly Lys Ile Gly Met Gly Arg Asp Trp Leu Ile Ser Asp
    130                 135                 140

Cys Asn Thr Gly Glu Ile Leu Val Arg Ala Thr Ser Val Tyr Ala Met
145                 150                 155                 160

Met Asn Gln Lys Thr Arg Arg Phe Ser Lys Leu Pro His Glu Val Arg
                165                 170                 175

Gln Glu Phe Ala Pro His Phe Leu Asp Ser Pro Ala Ile Glu Asp
            180                 185                 190

Asn Asp Gly Lys Leu Gln Lys Phe Asp Val Lys Thr Gly Asp Ser Ile
        195                 200                 205

Arg Lys Gly Leu Thr Pro Gly Trp Tyr Asp Leu Asp Val Asn Gln His
    210                 215                 220
```

Val Ser Asn Val Lys Tyr Ile Gly Trp Ile Leu Glu Ser Met Pro Thr
225                 230                 235                 240

Glu Val Leu Glu Thr Gln Glu Leu Cys Ser Leu Thr Leu Glu Tyr Arg
            245                 250                 255

Arg Glu Cys Gly Arg Asp Ser Val Leu Glu Ser Val Thr Ser Met Asp
            260                 265                 270

Pro Ser Lys Val Gly Asp Arg Phe Gln Tyr Arg His Leu Leu Arg Leu
        275                 280                 285

Glu Asp Gly Ala Asp Ile Met Arg Gly Arg Thr Glu Trp Arg Pro Lys
290                 295                 300

Asn Ala Gly Thr Asn Gly Ala Ile Ser Thr Gly Lys Thr
305                 310                 315

<210> SEQ ID NO 11
<211> LENGTH: 953
<212> TYPE: DNA
<213> ORGANISM: Artificial Sequence
<220> FEATURE:
<223> OTHER INFORMATION: CpFatB1.2 M4 Mutant

<400> SEQUENCE: 11
atgctgctca ccgcgattac caccgtgttc gttgcgccgg aaaacgttgg actatgtttg      60
accgcaaatc taaacgtccg agcatgctga tggatagctt cggtctggaa cgtgttgtcc    120
aggatggtct ggttttccgc caatccttct ccattcgtag ctacgaaatc tgtgcggacc    180
gcacggcgag catggagacc gtgatgaacc acgttcagga aaccagcctg aaccagtgta    240
agtccatcgg cctgctggac gacggtttcg gtcgctcacc ggaaatgtgt aaacgcgacc    300
tgatttgggt tgtaacccgt atgaaaatta tggtaaaccg ttatccgacc tggggcgaca    360
ccattgaagt ctccacctgg ctgtcccagt ccggtaaaat tggcatgggt cgcgactggc    420
tgattagcga ttgtaatacc ggtgaaatac tggttcgtgc aacctcagtt tacgccatga    480
tgaaccagaa aacgcgtcgc ttctctaaac tgccccacga agtacgccag gagttcgcgc    540
cgcacttctt agactccccg ccggccattg aagacaacga cggtaaactg cagaaattcg    600
atgtgaaaac cggtgattcc atccgcaaag gtctgacccc gggctggtac gacctggacg    660
taaaccagca cgtttccaat gtcaaatata tcggttggat cctggaatcc atgccgaccg    720
aagttctgga aacccaagaa ctttgcagcc tgactctcga ataccgtcgc gaatgcggtc    780
gcgactcagt acttgagagc gtaacctcca tggacccgtc taaagttggt gatcgttttc    840
agtatcgtca tctgctgcgt ctggaagatg gtgcggacat tatgaagggc cgtaccgaat    900
ggcgtccgaa aaacgcgggc actaatggtg ctatctccac tgggaaaaca taa           953

<210> SEQ ID NO 12
<211> LENGTH: 317
<212> TYPE: PRT
<213> ORGANISM: Artificial Sequence
<220> FEATURE:
<223> OTHER INFORMATION: CpFatB1.2 M4 Mutant

<400> SEQUENCE: 12

Tyr Ala Ala His Arg Asp Tyr His Arg Val Arg Cys Ala Gly Lys Arg
1               5                   10                  15

Trp Thr Met Phe Asp Arg Lys Ser Lys Arg Pro Ser Met Leu Met Asp
            20                  25                  30

Ser Phe Gly Leu Glu Arg Val Val Gln Asp Gly Leu Val Phe Arg Gln
        35                  40                  45

```
Ser Phe Ser Ile Arg Ser Tyr Glu Ile Cys Ala Asp Arg Thr Ala Ser
    50                  55                  60

Met Glu Thr Val Met Asn His Val Gln Glu Thr Ser Leu Asn Gln Cys
65                  70                  75                  80

Lys Ser Ile Gly Leu Leu Asp Asp Gly Phe Gly Arg Ser Pro Glu Met
                85                  90                  95

Cys Lys Arg Asp Leu Ile Trp Val Val Thr Arg Met Lys Ile Met Val
            100                 105                 110

Asn Arg Tyr Pro Thr Trp Gly Asp Thr Ile Glu Val Ser Thr Trp Leu
        115                 120                 125

Ser Gln Ser Gly Lys Ile Gly Met Gly Arg Asp Trp Leu Ile Ser Asp
    130                 135                 140

Cys Asn Thr Gly Glu Ile Leu Val Arg Ala Thr Ser Val Tyr Ala Met
145                 150                 155                 160

Met Asn Gln Lys Thr Arg Arg Phe Ser Lys Leu Pro His Glu Val Arg
                165                 170                 175

Gln Glu Phe Ala Pro His Phe Leu Asp Ser Pro Ala Ile Glu Asp
            180                 185                 190

Asn Asp Gly Lys Leu Gln Lys Phe Asp Val Lys Thr Gly Asp Ser Ile
        195                 200                 205

Arg Lys Gly Leu Thr Pro Gly Trp Tyr Asp Leu Asp Val Asn Gln His
    210                 215                 220

Val Ser Asn Val Lys Tyr Ile Gly Trp Ile Leu Glu Ser Met Pro Thr
225                 230                 235                 240

Glu Val Leu Glu Thr Gln Glu Leu Cys Ser Leu Thr Leu Glu Tyr Arg
                245                 250                 255

Arg Glu Cys Gly Arg Asp Ser Val Leu Glu Ser Val Thr Ser Met Asp
            260                 265                 270

Pro Ser Lys Val Gly Asp Arg Phe Gln Tyr Arg His Leu Leu Arg Leu
        275                 280                 285

Glu Asp Gly Ala Asp Ile Met Lys Gly Arg Thr Glu Trp Arg Pro Lys
    290                 295                 300

Asn Ala Gly Thr Asn Gly Ala Ile Ser Thr Gly Lys Thr
305                 310                 315

<210> SEQ ID NO 13
<211> LENGTH: 900
<212> TYPE: DNA
<213> ORGANISM: Artificial Sequence
<220> FEATURE:
<223> OTHER INFORMATION: CpFatB1.2 M4-287 Mutant

<400> SEQUENCE: 13
atgtttgacc gcaaatctaa acgtccgagc atgctgatgg atagcttcgg tctggaacgt    60
gttgtccagg atggtctggt tttccgccaa tccttctcca ttcgtagcta cgaaatctgt   120
gcggaccgca cggcgagcat ggagaccgtg atgaaccacg ttcaggaaac cagcctgaac   180
cagtgtaagt ccatcggcct gctggacgac ggtttcggtc gctcaccgga aatgtgtaaa   240
cgcgacctga tttgggttgt aacccgtatg aaaattatgg taaaccgtta tccgacctgg   300
ggcgacacca ttgaagtctc cacctggctg tcccagtccg gtaaaattgg catgggtcgc   360
gactggctga ttagcgattg taataccggt gaaatactgg tcgtgcaac ctcagtttac   420 gccatgatga accagaaaac gcgtcgcttc tctaaactgc cccacgaagt acgccaggag   480
ttcgcgccgc acttcttaga ctccccgccg gccattgaag acaacgacgg taaactgcag   540
```

```
aaattcgatg tgaaaaccgg tgattccatc cgcaaaggtc tgaccccggg ctggtacgac      600
ctggacgtaa accagcacgt ttccaatgtc aaatatatcg gttggatcct ggaatccatg      660
ccgaccgaag ttctggaaac caagaactt tgcagcctga ctctcgaata ccgtcgcgaa       720
tgcggtcgcg actcagtact tgagagcgta acctccatgg acccgtctaa agttggtgat      780
cgttttcagt atcgtcatct gctgcgtctg gaagatggtg cggacattat gaagggccgt      840
accgaatggc gtccgaaaaa cgcgggcact aatggtgcta tctccactgg gaaaacataa      900
```

<210> SEQ ID NO 14
<211> LENGTH: 299
<212> TYPE: PRT
<213> ORGANISM: Artificial Sequence
<220> FEATURE:
<223> OTHER INFORMATION: CpFatB1.2 M4-287 Mutant

<400> SEQUENCE: 14

```
Met Phe Asp Arg Lys Ser Lys Arg Pro Ser Met Leu Met Asp Ser Phe
1               5                   10                  15

Gly Leu Glu Arg Val Val Gln Asp Gly Leu Val Phe Arg Gln Ser Phe
            20                  25                  30

Ser Ile Arg Ser Tyr Glu Ile Cys Ala Asp Arg Thr Ala Ser Met Glu
        35                  40                  45

Thr Val Met Asn His Val Gln Glu Thr Ser Leu Asn Gln Cys Lys Ser
    50                  55                  60

Ile Gly Leu Leu Asp Asp Gly Phe Gly Arg Ser Pro Glu Met Cys Lys
65                  70                  75                  80

Arg Asp Leu Ile Trp Val Val Thr Arg Met Lys Ile Met Val Asn Arg
                85                  90                  95

Tyr Pro Thr Trp Gly Asp Thr Ile Glu Val Ser Thr Trp Leu Ser Gln
            100                 105                 110

Ser Gly Lys Ile Gly Met Gly Arg Asp Trp Leu Ile Ser Asp Cys Asn
        115                 120                 125

Thr Gly Glu Ile Leu Val Arg Ala Thr Ser Val Tyr Ala Met Met Asn
    130                 135                 140

Gln Lys Thr Arg Arg Phe Ser Lys Leu Pro His Glu Val Arg Gln Glu
145                 150                 155                 160

Phe Ala Pro His Phe Leu Asp Ser Pro Ala Ile Glu Asp Asn Asp
                165                 170                 175

Gly Lys Leu Gln Lys Phe Asp Val Lys Thr Gly Asp Ser Ile Arg Lys
            180                 185                 190

Gly Leu Thr Pro Gly Trp Tyr Asp Leu Asp Val Asn Gln His Val Ser
        195                 200                 205

Asn Val Lys Tyr Ile Gly Trp Ile Leu Glu Ser Met Pro Thr Glu Val
    210                 215                 220

Leu Glu Thr Gln Glu Leu Cys Ser Leu Thr Leu Glu Tyr Arg Arg Glu
225                 230                 235                 240

Cys Gly Arg Asp Ser Val Leu Glu Ser Val Thr Ser Met Asp Pro Ser
                245                 250                 255

Lys Val Gly Asp Arg Phe Gln Tyr Arg His Leu Leu Arg Leu Glu Asp
            260                 265                 270

Gly Ala Asp Ile Met Lys Gly Arg Thr Glu Trp Arg Pro Lys Asn Ala
        275                 280                 285

Gly Thr Asn Gly Ala Ile Ser Thr Gly Lys Thr
    290                 295
```

<210> SEQ ID NO 15
<211> LENGTH: 1812
<212> TYPE: DNA
<213> ORGANISM: Mycobacterium tuberculosis

<400> SEQUENCE: 15

| | | | | | |
|---|---|---|---|---|---|
| atgagcgatt | attatggtgg | tgcacatacc | accgttcgtc | tgattgatct | ggcaacccgt | 60 |
| atgcctcgtg | ttctggcaga | tacaccggtt | attgttcgtg | gtgcaatgac | cggtctgctg | 120 |
| gcacgtccga | atagcaaagc | aagcattggc | accgtttttc | aggatcgtgc | agcacgttat | 180 |
| ggtgatcgtg | ttttttctgaa | atttggtgat | cagcaactga | cctatcgtga | tgcaaatgca | 240 |
| accgcaaatc | gttatgcagc | agtgctggca | gcacgtggtg | ttggtccggg | tgatgttgtt | 300 |
| ggtattatgc | tgcgtaatag | cccgagcacc | gttctggcaa | tgctggcaac | cgttaaatgt | 360 |
| ggtgccattg | caggtatgct | gaattatcat | cagcgtggtg | aagttctggc | acatagcctg | 420 |
| ggcctgctgg | atgcaaaagt | tctgattgca | gaaagcgatc | tggttagcgc | agttgcagaa | 480 |
| tgcggtgcaa | gccgtggtcg | tgttgccggt | gatgttctga | ccgttgaaga | tgttgaacgt | 540 |
| tttgcaacca | ccgctccggc | aaccaatccg | gcaagcgcaa | gcgcagttca | ggcaaaagat | 600 |
| accgcctttt | atatctttac | cagcggcacc | accggttttc | cgaaagcaag | cgttatgacc | 660 |
| catcatcgtt | ggctgcgtgc | actggcagtt | tttggtggta | tgggtctgcg | tctgaaaggt | 720 |
| agcgataccc | tgtatagctg | tctgccgctg | tatcataata | atgcactgac | cgtggcagtt | 780 |
| tccagcgtga | ttaatagcgg | tgcaaccctg | gcactgggta | aaagttttag | cgcaagccgt | 840 |
| ttttgggatg | aagttattgc | aaatcgtgca | accgcctttg | tgtatattgg | tgaaatttgt | 900 |
| cgctatctgc | tgaatcagcc | tgcaaaaccg | accgatcgtg | cacatcaggt | tcgtgttatt | 960 |
| tgtggtaatg | gcctgcgtcc | ggaaatctgg | gatgaattta | ccacccgttt | tggtgttgca | 1020 |
| cgtgtttgtg | agttttatgc | agccagcgaa | ggtaatagcg | cctttattaa | cattttaac | 1080 |
| gttccgcgta | ccgcaggcgt | tagcccgatg | ccgctggcat | tgttgaata | tgatctggat | 1140 |
| accggtgatc | cgctgcgtga | tgcgagcggt | cgtgttcgtc | gtgtgccgga | tggtgaaccg | 1200 |
| ggtctgctgc | tgagccgtgt | taatcgtctg | caaccgtttg | atggttatac | cgatccggtt | 1260 |
| gcaagcgaaa | aaaaactggt | tcgtaatgca | tttcgtgatg | gcgattgttg | gtttaataca | 1320 |
| ggtgatgtta | tgagtccgca | gggtatgggc | catgcagcct | tgttgatcg | tctgggtgat | 1380 |
| acctttcgtt | ggaaaggtga | aaatgttgcc | accacccagg | ttgaagcagc | actggcaagc | 1440 |
| gatcagaccg | tggaagaatg | taccgtttat | ggtgtgcaga | ttcctcgtac | cggtggtcgt | 1500 |
| gccggtatgg | cagcaattac | cctgcgtgcc | ggtgcagaat | tgatggtca | ggcactggca | 1560 |
| cgcaccgtgt | atggtcatct | gcctggttat | gcactgcctc | tgtttgttcg | tgttgtgggt | 1620 |
| agcctggcgc | ataccacaac | ctttaaaagc | cgtaaagttg | aactgcgtaa | tcaggcctat | 1680 |
| ggtgcagata | ttgaagatcc | gctgtatgta | ctggcaggtc | cggatgaagg | ttatgttccg | 1740 |
| tattatgcag | aatatccgga | agaagttagc | ctgggtcgtc | gtcctcaggg | tcatcatcat | 1800 |
| caccatcatt | aa | | | | | 1812 |

<210> SEQ ID NO 16
<211> LENGTH: 603
<212> TYPE: PRT
<213> ORGANISM: Mycobacterium tuberculosis

<400> SEQUENCE: 16

```
Met Ser Asp Tyr Tyr Gly Gly Ala His Thr Thr Val Arg Leu Ile Asp
1               5                   10                  15

Leu Ala Thr Arg Met Pro Arg Val Leu Ala Asp Thr Pro Val Ile Val
            20                  25                  30

Arg Gly Ala Met Thr Gly Leu Leu Ala Arg Pro Asn Ser Lys Ala Ser
        35                  40                  45

Ile Gly Thr Val Phe Gln Asp Arg Ala Ala Arg Tyr Gly Asp Arg Val
    50                  55                  60

Phe Leu Lys Phe Gly Asp Gln Gln Leu Thr Tyr Arg Asp Ala Asn Ala
65                  70                  75                  80

Thr Ala Asn Arg Tyr Ala Ala Val Leu Ala Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
        355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Val Pro Asp Gly Glu Pro
385                 390                 395                 400

Gly Leu Leu Leu Ser Arg Val Asn Arg Leu Gln Pro Phe Asp Gly Tyr
                405                 410                 415
```

```
Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
                435                 440                 445

Met Gly His Ala Ala Phe Val Asp Arg Leu Gly Asp Thr Phe Arg Trp
        450                 455                 460

Lys Gly Glu Asn Val Ala Thr Thr Gln Val Glu Ala Ala Leu Ala Ser
465                 470                 475                 480

Asp Gln Thr Val Glu Cys Thr Val Tyr Val Gln Ile Pro Arg
                485                 490                 495

Thr Gly Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
            580                 585                 590

Arg Arg Pro Gln Gly His His His His His
            595                 600
```

```
<210> SEQ ID NO 17
<211> LENGTH: 1701
<212> TYPE: DNA
<213> ORGANISM: Pseudomonas putida

<400> SEQUENCE: 17
```

| | | | | |
|---|---|---|---|---|
| atgttgcaga cacgcatcat caagcccgcc gagggcgcct atgcctatcc attgctgatc | 60 |
| aagcgcctgc tgatgtccgg cagccgctat gaaaagaccc gggaaatcgt ctaccgcgac | 120 |
| cagatgcggc tgacgtatcc acagctcaac gagcgcattg cccgcctggc caacgtgctg | 180 |
| accgaggccg gggtcaaggc cggtgacacc gtggcggtga tggactggga cagccatcgc | 240 |
| tacctggaat gcatgttcgc catcccgatg atcggcgctg tggtgcacac catcaacgtg | 300 |
| cgcctgtcgc ccgagcagat cctctacacc atgaaccatg ccgaagaccg cgtggtgctg | 360 |
| gtcaacagcg acttcgtcgg cctgtaccag gccatcgccg gcagctgac cactgtcgac | 420 |
| aagaccctgc tactgaccga tggcccggac aagactgccg aactgcccgg tctggtcggc | 480 |
| gagtatgagc agctgctggc tgctgccagc ccgcgctacg acttcccgga tttcgacgag | 540 |
| aattcggtgg ccactacctt ctacaccact ggcaccaccg gtaaccccaa gggcgtgtat | 600 |
| ttcagtcacc gccagctggt gctgcacacc ctggccgagg cctcggtcac cggcagtatc | 660 |
| gacagcgtgc gcctgctggg cagcaacgat gtgtacatgc ccatcacccc gatgttccac | 720 |
| gtgcatgcct ggggcatccc ctacgctgcc accatgctcg gcatgaagca ggtgtaccca | 780 |
| gggcgctacg agccggacat gctggtcaag ctttggcgtg aagagaaggt cactttctcc | 840 |
| cactgcgtgc cgaccatcct gcagatgctg ctcaactgcc gaacgccca ggggcaggac | 900 |
| ttcggcggct ggaagatcat catcggcggc agctcgctca accgttcgct gtaccaggcc | 960 |
| gccctgcgc gcggcatcca gctgaccgcc gcgtatggca tgtcggaaac ctgcccgctg | 1020 |
| atctccgcgg cacacctgaa cgatgaactg caggccggca gcgaggatga gcgcgtcact | 1080 |

```
taccgtatca aggccggtgt gccggtgccg ttggtcgaag cggccatcgt cgacggcgaa    1140
ggcaacttcc tgcccgccga tggtgaaacc cagggcgagc tggtactgcg tgcgccgtgg    1200
ctgaccatgg gctacttcaa ggagccggag aagagcgagg agctgtggca gggcggctgg    1260
ctgcacaccg tgacgtcgc cacccctcgac ggcatgggct acatcgacat ccgcgaccgc    1320
```

```
taccgtatca aggccggtgt gccggtgccg ttggtcgaag cggccatcgt cgacggcgaa    1140
ggcaacttcc tgcccgccga tggtgaaacc cagggcgagc tggtactgcg tgcgccgtgg    1200
ctgaccatgg gctacttcaa ggagccggag aagagcgagg agctgtggca gggcggctgg    1260
ctgcacaccg tgacgtcgc cacccctcgac ggcatgggct acatcgacat ccgcgaccgc    1320
atcaaggatg tgatcaagac cggtggcgag tgggtttcct cgctcgacct ggaagacctg    1380
atcagccgcc acccgccgt gcgcgaagtg gcggtggtgg gggtggccga cccgcagtgg    1440
ggtgagcgcc cgtttgccct gctggtggca cgtgacggcc acgatatcga cgccaaggcg    1500
ctgaaggaac acctcaagcc attcgtcgag caaggtcata tcaacaagtg gcgattcca    1560
agccagatcg cccttgttac tgaaattccc aagaccagtg tcggcaagct cgacaagaaa    1620
cgcattcgcc aggacatcgt ccagtggcag gccagcaaca gcgcgttcct ttccacgttg    1680
catcaccatc accatcacta a                                              1701
```

<210> SEQ ID NO 18
<211> LENGTH: 566
<212> TYPE: PRT
<213> ORGANISM: Pseudomonas putida

<400> SEQUENCE: 18

```
Met Leu Gln Thr Arg Ile Ile Lys Pro Ala Glu Gly Ala Tyr Ala Tyr
1               5                   10                  15

Pro Leu Leu Ile Lys Arg Leu Leu Met Ser Gly Ser Arg Tyr Glu Lys
            20                  25                  30

Thr Arg Glu Ile Val Tyr Arg Asp Gln Met Arg Leu Thr Tyr Pro Gln
        35                  40                  45

Leu Asn Glu Arg Ile Ala Arg Leu Ala Asn Val Leu Thr Glu Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val Val His
                85                  90                  95

Thr Ile Asn Val Arg Leu Ser Pro Glu Gln Ile Leu Tyr Thr Met Asn
            100                 105                 110

His Ala Glu Asp Arg Val Val Leu Val Asn Ser Asp Phe Val Gly Leu
        115                 120                 125

Tyr Gln Ala Ile Ala Gly Gln Leu Thr Thr Val Asp Lys Thr Leu Leu
    130                 135                 140

Leu Thr Asp Gly Pro Asp Lys Thr Ala Glu Leu Pro Gly Leu Val Gly
145                 150                 155                 160

Glu Tyr Glu Gln Leu Leu Ala Ala Ala Ser Pro Arg Tyr Asp Phe Pro
                165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Ser His Arg Gln Leu Val Leu
        195                 200                 205

His Thr Leu Ala Glu Ala Ser Val Thr Gly Ser Ile Asp Ser Val Arg
    210                 215                 220

Leu Leu Gly Ser Asn Asp Val Tyr Met Pro Ile Thr Pro Met Phe His
225                 230                 235                 240

Val His Ala Trp Gly Ile Pro Tyr Ala Ala Thr Met Leu Gly Met Lys
                245                 250                 255
```

-continued

```
Gln Val Tyr Pro Gly Arg Tyr Glu Pro Asp Met Leu Val Lys Leu Trp
            260                 265                 270

Arg Glu Glu Lys Val Thr Phe Ser His Cys Val Pro Thr Ile Leu Gln
        275                 280                 285

Met Leu Leu Asn Cys Pro Asn Ala Gln Gly Gln Asp Phe Gly Gly Trp
    290                 295                 300

Lys Ile Ile Ile Gly Gly Ser Ser Leu Asn Arg Ser Leu Tyr Gln Ala
305                 310                 315                 320

Ala Leu Ala Arg Gly Ile Gln Leu Thr Ala Ala Tyr Gly Met Ser Glu
                325                 330                 335

Thr Cys Pro Leu Ile Ser Ala Ala His Leu Asn Asp Glu Leu Gln Ala
                340                 345                 350

Gly Ser Glu Asp Glu Arg Val Thr Tyr Arg Ile Lys Ala Gly Val Pro
            355                 360                 365

Val Pro Leu Val Glu Ala Ala Ile Val Asp Gly Glu Gly Asn Phe Leu
        370                 375                 380

Pro Ala Asp Gly Glu Thr Gln Gly Glu Leu Val Leu Arg Ala Pro Trp
385                 390                 395                 400

Leu Thr Met Gly Tyr Phe Lys Glu Pro Glu Lys Ser Glu Glu Leu Trp
                405                 410                 415

Gln Gly Gly Trp Leu His Thr Gly Asp Val Ala Thr Leu Asp Gly Met
            420                 425                 430

Gly Tyr Ile Asp Ile Arg Asp Arg Ile Lys Asp Val Ile Lys Thr Gly
            435                 440                 445

Gly Glu Trp Val Ser Ser Leu Asp Leu Glu Asp Leu Ile Ser Arg His
450                 455                 460

Pro Ala Val Arg Glu Val Ala Val Val Gly Val Ala Asp Pro Gln Trp
465                 470                 475                 480

Gly Glu Arg Pro Phe Ala Leu Leu Val Ala Arg Asp Gly His Asp Ile
                485                 490                 495

Asp Ala Lys Ala Leu Lys Glu His Leu Lys Pro Phe Val Glu Gln Gly
                500                 505                 510

His Ile Asn Lys Trp Ala Ile Pro Ser Gln Ile Ala Leu Val Thr Glu
            515                 520                 525

Ile Pro Lys Thr Ser Val Gly Lys Leu Asp Lys Lys Arg Ile Arg Gln
        530                 535                 540

Asp Ile Val Gln Trp Gln Ala Ser Asn Ser Ala Phe Leu Ser Thr Leu
545                 550                 555                 560

His His His His His
                565
```

MUTANT THIOESTERASES

FEDERAL FUNDING STATEMENT

This invention was made with government support under CBET1149678 awarded by the National Science Foundation. The government has certain rights in the invention.

FIELD OF THE INVENTION

The invention is directed to mutant thioesterases having enhanced medium chain substrate activity, polynucleotides encoding and configured to express the mutant thioesterases in a transformed host cell, host cells transformed to contain the polynucleotides, and related methods.

BACKGROUND

Free fatty acids (FFAs) are energy-rich molecules capable of serving as precursors for the production of liquid transportation fuels and high-value oleochemicals. Fuel properties are dictated by the aliphatic chain length and degree of saturation of the FFA precursors. Medium-chain (C6-C12) FFA feedstocks can be converted to hydrocarbons with fuel properties comparable to gasoline, diesel, or jet fuel (Choi et al. 2013 and Lee et al. 2008). Fuels derived from microbially produced FFAs would facilitate reduction of the carbon footprint and, unlike bioethanol, avoid expensive and laborious infrastructure and engine remodeling (Howard et al. 2013).

*Escherichia coli* is a popular microbial host for FFA production because of its established type II fatty acid biosynthesis (FAB) pathway, short doubling time, and genetic tractability. The *E. coli* FAB pathway is initiated by the ATP-dependent carboxylation of acetyl-CoA to malonyl-CoA. Subsequently, CoA is exchanged with acyl carrier protein (ACP), the recognition tag of FAB, producing malonyl-ACP. Malonyl-ACP and acetyl-CoA are condensed to yield acetoacetyl-ACP. The alkyl chain of the β-ketoacyl-ACP is successively extended by two carbon atoms that originate from additional malonyl-ACP. This cycle is terminated by the acyl-ACP thioesterase, which hydrolyzes the thioester bond to generate the FFA and ACP. The specificity of the acyl-ACP thioesterase controls the terminal aliphatic chain length and chemical properties of the FFA product composition. Regulation of the FFA chain length produced through the FAB pathway has typically been achieved by the overexpression of the two native *E. coli* thioesterases (TesA and TesB), or heterologous expression of various plant and bacterial thioesterases, which exhibit a wide range of substrate specificities (Choi et al. 2013, Steen et al. 2010, Zhang et al. 2011, Lu et al. 2008, Voelker et al. 1994, Dormann et al. 1995).

Several of these thioesterases have been evolved to further diversify the gamut of attainable FFA compositions. Despite this diversification, very few thioesterases are specific towards a unique aliphatic chain length. Of these studied thioesterases, 'TesA (a cytosolic TesA that lacks the N-terminal signal peptide and whose crystal structure has been elucidated) produces one of the highest FFA titers (Steen et al. 2010, Choi et al. 2013, Cho et al. 1993, Lo et al. 2005). In spite of these clear advantages, 'TesA has broad substrate specificity that necessitates costly downstream separation (Steen et al. 2010, Choi et al. 2013).

The carbon chain length of fatty acids is economically significant because the natural occurrence of certain types of fatty acids, such as medium-chain fatty acids (carbon chain of 6 to 12 carbon atoms) in general and C8 carbon chain length fatty acids in particular, is notably less than long-chain fatty acids (carbon chain longer than 12 carbon atoms). There are currently only two notable sources for C8 fatty acids, coconut and palm kernel, and C8 fatty acids are only a minor fraction of the fatty acids made by these sources. C8 fatty acids and related C8 compounds are important in light of their use in cosmetics, plastics, and other oleochemical products.

Tools and methods for producing high amounts C8 fatty acids and products derived therefrom are needed.

SUMMARY OF THE INVENTION

One aspect of the invention is directed to an unnatural, mutated protein. The protein can comprise an amino acid sequence at least about 80% identical to positions 28-317 of SEQ ID NO:4. The amino acid sequence can comprise one or more of: a residue other than asparagine at a position corresponding to position 28 of SEQ ID NO:4; a residue other than methionine at a position corresponding to position 29 of SEQ ID NO:4; a residue other than alanine at a position corresponding to position 59 of SEQ ID NO:4; a residue other than isoleucine at a position corresponding to position 65 of SEQ ID NO:4; a residue other than leucine at a position corresponding to position 86 of SEQ ID NO:4; a residue other than threonine at a position corresponding to position 117 of SEQ ID NO:4; a residue other than methionine at a position corresponding to position 136 of SEQ ID NO:4; a residue other than asparagine at a position corresponding to position 146 of SEQ ID NO:4; a residue other than glutamine at a position corresponding to position 163 of SEQ ID NO:4; a residue other than threonine at a position corresponding to position 204 of SEQ ID NO:4; a residue other than serine at a position corresponding to position 207 of SEQ ID NO:4; a residue other than glutamate at a position corresponding to position 236 of SEQ ID NO:4; a residue other than leucine at a position corresponding to position 251 of SEQ ID NO:4; a residue other than arginine at a position corresponding to position 261 of SEQ ID NO:4; a residue other than leucine at a position corresponding to position 265 of SEQ ID NO:4; a residue other than valine at a position corresponding to position 268 of SEQ ID NO:4; a residue other than arginine at a position corresponding to position 279 of SEQ ID NO:4; a residue other than aspartate at a position corresponding to position 293 of SEQ ID NO:4; a residue other than lysine at a position corresponding to position 296 of SEQ ID NO:4; and a residue other than asparagine at a position corresponding to position 309 of SEQ ID NO:4; and/or the protein lacks an N-terminal portion having an amino acid sequence identical to positions 1-94 of SEQ ID NO:2. The protein preferably exhibits thioesterase activity.

The protein in some versions can comprise one or more of: a serine or a conservative variant of serine at the position corresponding to position 28 of SEQ ID NO:4; a threonine or a conservative variant of threonine at the position corresponding to position 29 of SEQ ID NO:4; a serine or a conservative variant of serine at the position corresponding to position 59 of SEQ ID NO:4; a methionine or a conservative variant of methionine at the position corresponding to position 65 of SEQ ID NO:4; a glutamine or a conservative variant of glutamine at the position corresponding to position 86 of SEQ ID NO:4; a serine or a conservative variant of serine at the position corresponding to position 117 of SEQ ID NO:4; a valine, an isoleucine, or a conservative variant of valine or isoleucine at the position corresponding to position 136 of SEQ ID NO:4; a lysine or a conservative variant of lysine at the position corresponding to position 146 of SEQ ID NO:4; a leucine or a conservative variant of leucine at the position corresponding to position 163 of SEQ ID NO:4; a serine or a conservative variant of serine at the position corresponding to position 204 of SEQ ID NO:4; a threonine or a conservative variant of threonine at the position corresponding to position 207 of SEQ ID NO:4; an alanine or a conservative variant of alanine at the position corresponding to position 236 of SEQ ID NO:4; a methionine or a conservative variant of methionine at the position corresponding to position 251 of SEQ ID NO:4; a serine or a conservative variant of serine at the position corresponding to position 261 of SEQ ID NO:4; an isoleucine or a conservative variant of isoleucine at the position corresponding to position 265 of SEQ ID NO:4; an isoleucine or a conservative variant of isoleucine at the position corresponding to position 268 of SEQ ID NO:4; a histidine or a conservative variant of histidine at the position corresponding to position 279 of SEQ ID NO:4; a valine or a conservative variant of valine at the position corresponding to position 293 of SEQ ID NO:4; an arginine or a conservative variant of arginine at the position corresponding to position 296 of SEQ ID NO:4; and an aspartate or a conservative variant of aspartate at the position corresponding to position 309 of SEQ ID NO:4.

In some versions, protein further comprises a sequence corresponding to positions 1-27 of SEQ ID NO:4, wherein the amino acid sequence comprises one or more of: a residue other than valine at a position corresponding to position 9 of SEQ ID NO:4; a residue other than lysine at a position corresponding to position 15 of SEQ ID NO:4; a residue other than tryptophan at a position corresponding to position 17 of SEQ ID NO:4; and a residue other than lysine at a position corresponding to position 23 of SEQ ID NO:4. The protein in some versions can comprises one or more of: a methionine or a conservative variant of methionine at the position corresponding to position 9 of SEQ ID NO:4; a glutamate or a conservative variant of glutamate at the position corresponding to position 15 of SEQ ID NO:4; an arginine or a conservative variant of arginine at the position corresponding to position 17 of SEQ ID NO:4; and a glutamate or a conservative variant of glutamate at the position corresponding to position 23 of SEQ ID NO:4.

In some versions, the protein comprises at least one of: a residue other than asparagine at the position corresponding to position 28 of SEQ ID NO:4; and a residue other than isoleucine at the position corresponding to position 65 of SEQ ID NO:4. The protein in some versions can comprise: a residue other than asparagine at the position corresponding to position 28 of SEQ ID NO:4; and a residue other than isoleucine at the position corresponding to position 65 of SEQ ID NO:4. The protein in some versions can comprise at least one of: a serine or a conservative variant of serine at the position corresponding to position 28 of SEQ ID NO:4; and a methionine or a conservative variant of methionine at the position corresponding to position 65 of SEQ ID NO:4. The protein in some versions can comprise: a serine or a conservative variant of serine at the position corresponding to position 28 of SEQ ID NO:4; and a methionine or a conservative variant of methionine at the position corresponding to position 65 of SEQ ID NO:4. The protein in some versions can lack an N-terminal portion having an amino acid sequence identical to positions 1-18 of SEQ ID NO:4.

In some versions, the protein comprises at least one of: a residue other than alanine at the position corresponding to position 59 of SEQ ID NO:4; and a residue other than lysine at the position corresponding to position 296 of SEQ ID NO:4. The protein in some versions can comprise: a residue other than alanine at the position corresponding to position 59 of SEQ ID NO:4; and a residue other than lysine at the position corresponding to position 296 of SEQ ID NO:4. The protein in some versions can comprise at least one of: a serine or a conservative variant of serine at the position corresponding to position 59 of SEQ ID NO:4; and an arginine or a conservative variant of arginine at the position corresponding to position 296 of SEQ ID NO:4. The protein in some versions can comprise: a serine or a conservative variant of serine at the position corresponding to position 59 of SEQ ID NO:4; and an arginine or a conservative variant of arginine at the position corresponding to position 296 of SEQ ID NO:4.

In some versions, the protein comprises a residue other than aspartate at the position corresponding to position 293 of SEQ ID NO:4. The protein in some versions can comprise a valine or a conservative variant of valine at the position corresponding to position 293 of SEQ ID NO:4.

In some versions, the protein comprises a residue other than lysine at the position corresponding to position 296 of SEQ ID NO:4. The protein in some versions can comprise an arginine or a conservative variant of arginine at the position corresponding to position 296 of SEQ ID NO:4.

Another aspect of the invention is directed to polynucleotides encoding the proteins of the invention.

Another aspect of the invention is directed to host cells comprising the polynucleotides of the invention.

Another aspect of the invention is directed to methods of producing a fatty acid derivative. The methods can comprise cultivating the host cell of the invention under conditions that permit production of the fatty acid derivative. In some versions, the fatty acid derivative comprises a C8 fatty acid derivative. In some versions, the C8 fatty acid derivative comprises octanoic acid.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Octanoic acid is a minor component in both of these sources.

Figure 2:
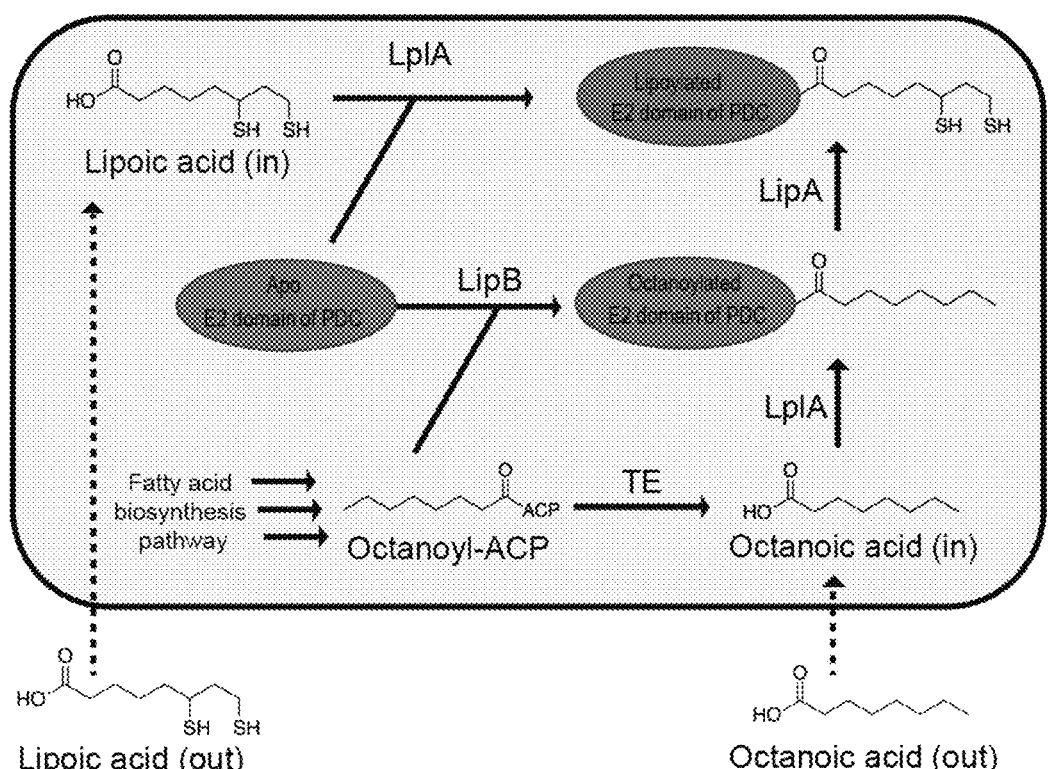

FIG. 2. Synthesis of lipoyl group of pyruvate dehydrogenase. Pyruvate dehydrogenase complex (PDC) requires a lipoylated E2 domain (green) for *E. coli* to grow in aerobic conditions. This can be achieved via direct incorporation of lipoic acid or octanoic acid (C8:0) from the media through LplA and LipA (only for C8:0) or the LipB-mediated octanoylation of Apo-E2 domain (red) followed by insertion of sulfurs via LipA. In the absence of lipoic acid and octanoic acid from the media, a ΔlipB strain can be rescued by the action of an octanyl-ACP thioesterase, which provides with intracellular C8:0 that can be used to lypolyate E2 domain of PDC.

FIG. 3A. CpFatB1 truncation sites with arrows indicating the position M1 for each new truncation.

FIG. 3B. Free fatty acid production from CpFatB1 truncations shown in FIG. 3A. Each truncation was cloned into ptrc99a plasmid. Isolated plasmids were transformed into the RL08ara (ΔfadD) E. coli strain and grown in LB 0.4% glycerol and 1 mM IPTG. CpFatB1.2 was chosen a baseline thioesterase for mutagenesis and selection in ΔlipB strain.

Figure 4:
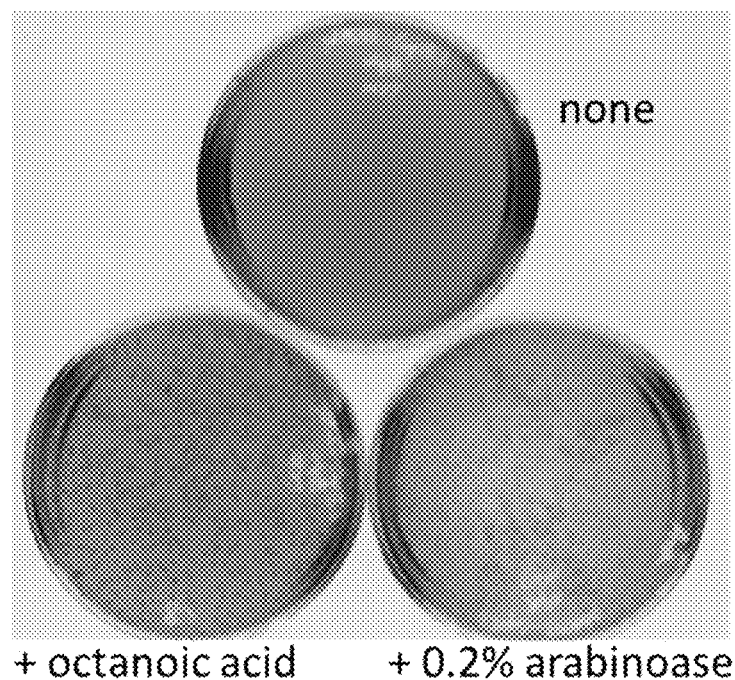

FIG. 4. Rescue of E. coli lipB null mutant expressing CpFatB1.2. E. coli lipB null mutant containing pBAD33-CpFatB1.2 can grow on MOPS minimal media-agarose containing 0.2% arabinose compared without the addition of the pBAD33-CpFatB1.2. The positive control was the plate with the addition of 50 μM octanoic acid. This shows that it is possible to use a thioesterase as an alternative to LipB in minimal media.

Figure 5:
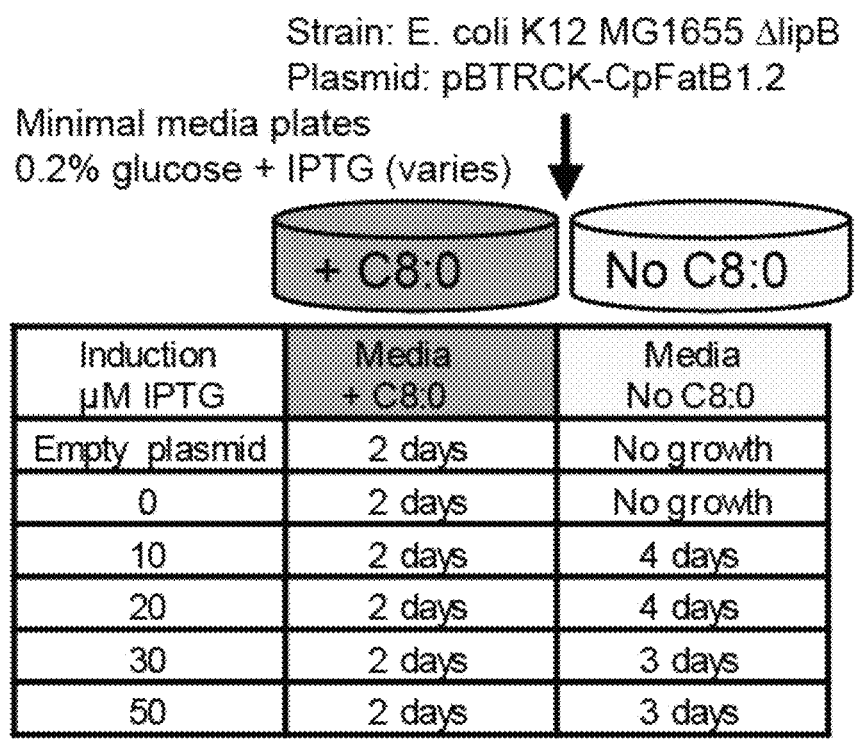

FIG. 5. Selection of optimal conditions for lipB screen with CpFatB1.2. A low copy plasmid (pBTRCK-CpFatB1.2) containing CpFatB1.2 under an IPTG-inducible promoter was transformed into E. coli ΔlipB strain and plated into MOPS minimal media plates containing different concentrations of IPTG. Growth in these plates was monitored for 4 days. Plates with 20 μM IPTG was selected for selection of mutants because E. coli ΔlipB carrying CpFatB1.2 took an extra day to grow (4 days), giving room for improved mutants to be selected the day before (3 days).

Figure 6:
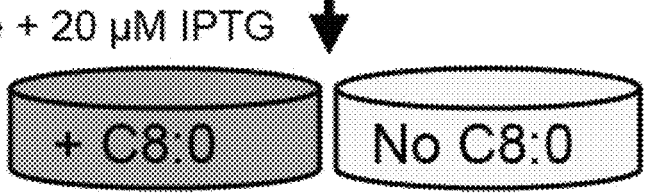

FIG. 6. Screening for improved mutants of CpFatB1.2. A library of pBTRCK-CpFatB1.2 mutants was created by random mutagenesis of the coding sequence CpFatB1.2 at a low mutation rate. This library was transformed into E. coli ΔlipB strain and plated into MOPS minimal media plates containing 20 μM IPTG. 90 putative mutant colonies were selected after 3 days for further characterization.

Figures 7A, 7B:
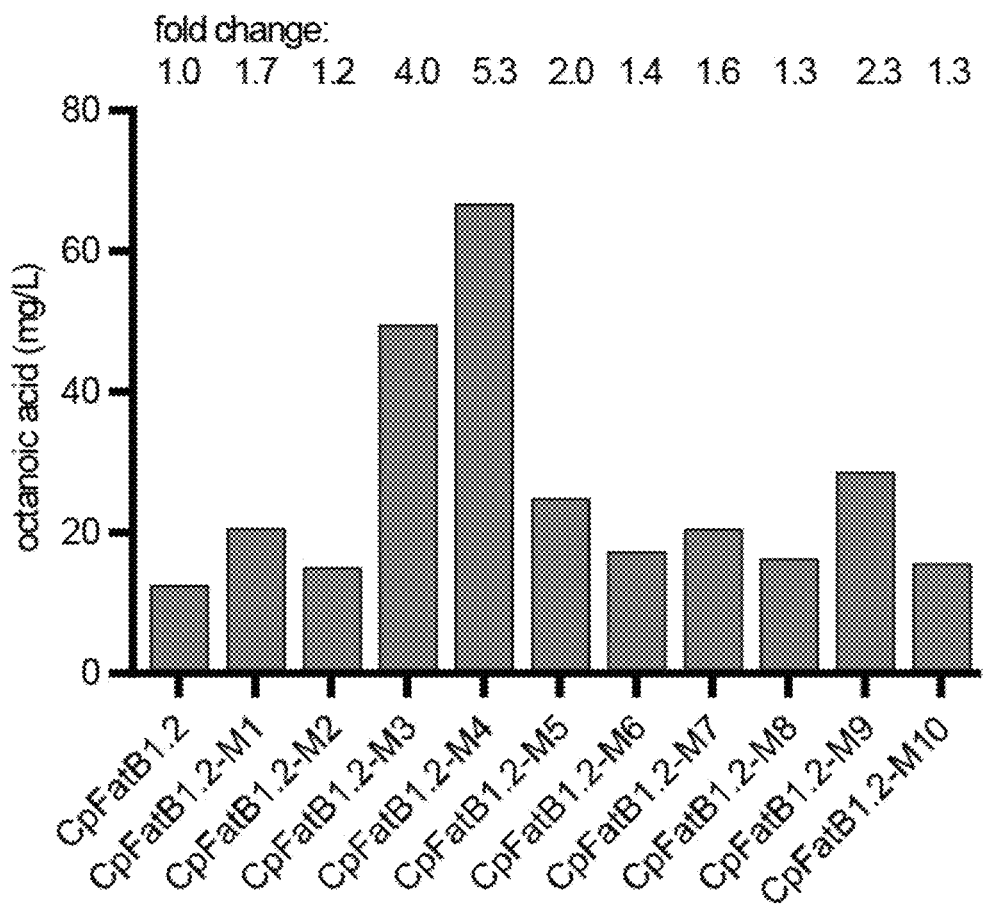

FIG. 7A. Mutations in CpFatB1.2 mutants 1-10. Sequence identity of CpFatB1.2 mutants 1-10 shows a mixture of CpFatB1.2 and CpFatB1.2 variants. The top three improved mutants (M3, M4 and M9) (see FIG. 7B) contained variations from CpFatB1.2. CpFatB1.2-M4 contains an early stop codon.

FIG. 7B. Octanoic acid production from CpFatB1.2 mutants 1-10. Plasmids from 10 of the 90 putative mutants were isolated and transformed into the RL08ara (ΔfadD) strain and grown in LB supplemented with 0.4% glycerol and 20 μM IPTG. Octanoic acid production for first ten mutants relative to baseline CpFatB1.2 identified two mutants with several fold improvement over CpFatB1.2.

Figures 8A, 8B:
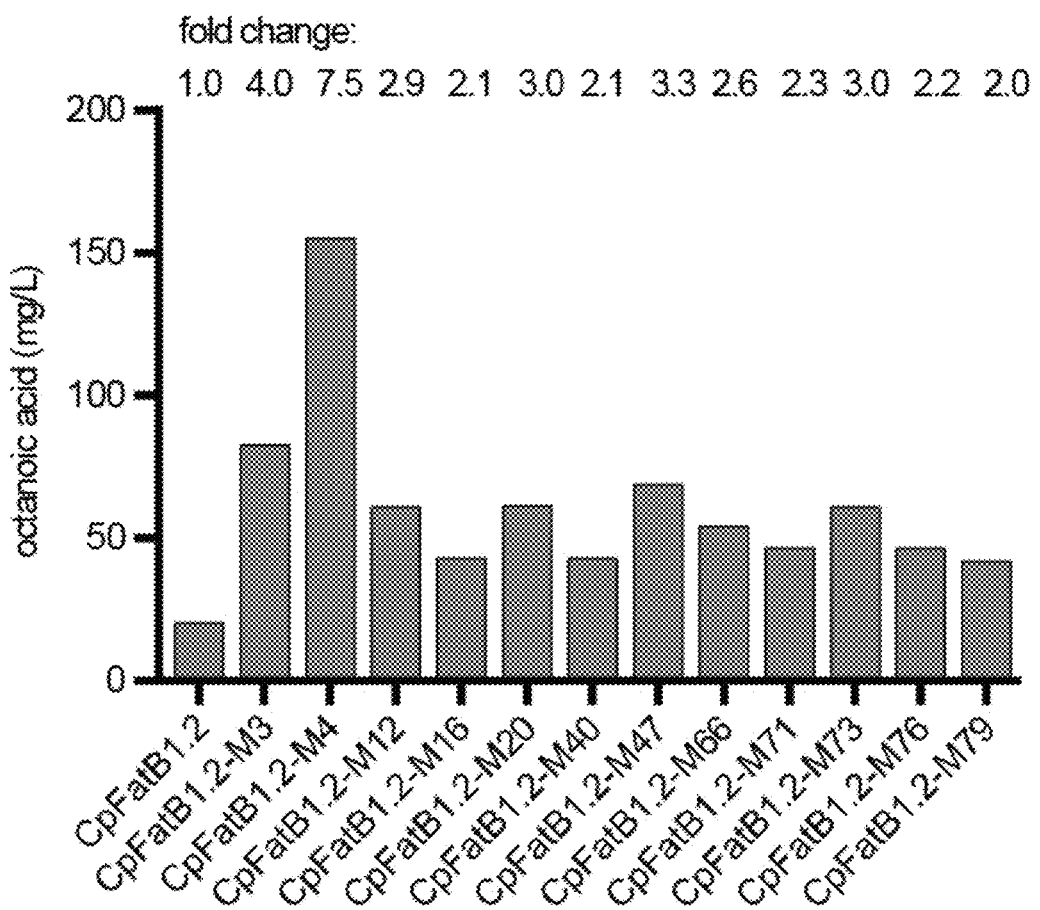

FIG. 8A. Mutations in additional CpFatB1.2.

FIG. 8B. Octanoic acid production from the additional CpFatB1.2 mutants presented in FIG. 8A.

Figure 9:
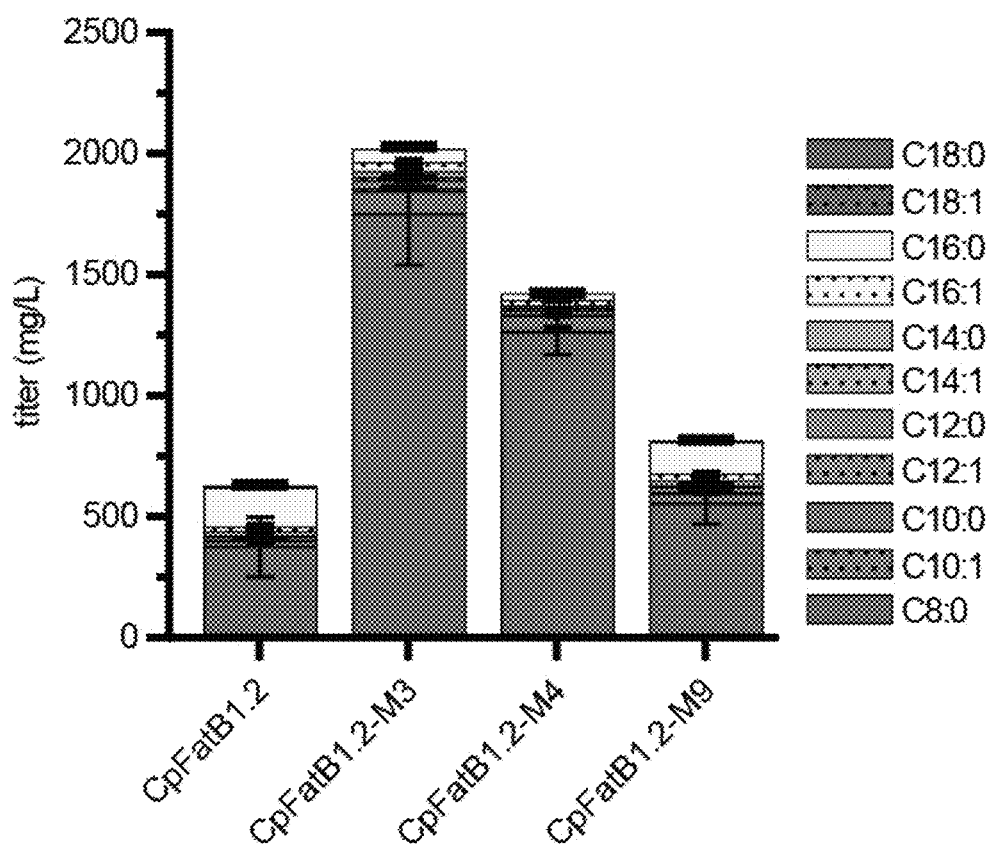

FIG. 9. Free fatty acid production from mutants CpFatB1.2-M3, CpFatB1.2-M4, and CpFatB1.2-M9 under high expression conditions. Mutants CpFatB1.2-M3, CpFatB1.2-M4, and CpFatB1.2-M9 were subcloned into high copy plasmid ptrc99a in order to remove possibilities of backbone mutations as well as increasing the expression levels to high MCFA production conditions. Plasmids were transformed into the RL08ara (ΔfadD) strain and grown in MOPS media (Kim et al. 2015) enriched with tryptone and yeast extract and 1 mM IPTG. Data shows several fold improvements over CpFatB1.2 in high expression conditions, consistent with the data shown in FIG. 7B for low expression conditions.

FIG. 10A. Generation of CpFatB1.2-M4 truncation variants CpFatB1.2-M4-287, CpFatB1.2-M4-288, CpFatB1.2-M4-289, CpFatB1.2-M4-290, and CpFatB1.2-M4-291. Characterization of CpFatB1.2-M4. Alignment of CpFatB1.2 with CpFatB1.2-M4 (ΔA54, N28S, I65M) shows a frame shift which that rose from nucleotide A54 deletion, producing a stop codon. Given that the enzyme is active, we proposed that it was being translated from a different in-frame methionine from a non-specific ribosome binding site (RBS). We identified five methionines (highlighted in green) in frame with CpFatB1.2 and cloned in-frame CpFatB1.2-M4 variants (CpFatB1.2-M4-287, CpFatB1.2-M4-288, CpFatB1.2-M4-289, CpFatB1.2-M4-290, and CpFatB1.2-M4-291) with the methionines as start codons.

Figure 10B:
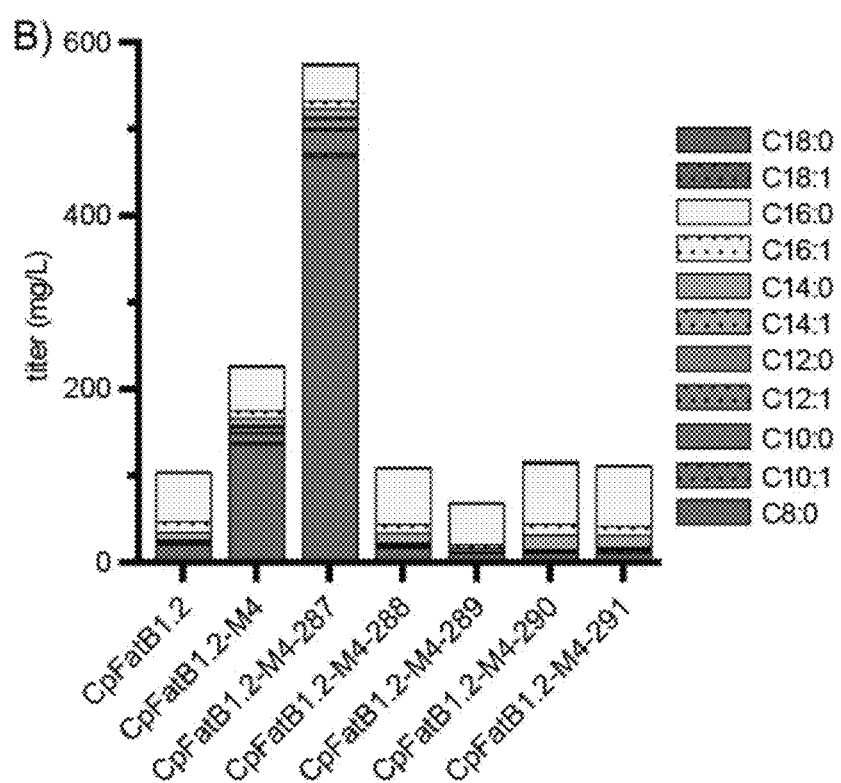

FIG. 10B. Free fatty acid production from the CpFatB1.2-M4 truncation variants. Isolated plasmids of each variant in FIG. 10A were transformed into the RL08ara (ΔfadD) strain and grown in LB 0.4% glycerol and 1 mM IPTG. Only variant CpFatB1.2-M4-287 showed high level of octanoic acid production characteristic of its parent CpFatB1.2-M4 sequence. Moreover, increased production observed in variant CpFatB1.2-M4-287 over CpFatB1.2-M4 suggests that the hypothesis of CpFatB1.2-M4 being translated from a non-specific RBS was correct. This places CpFatB1.2-M4-287 as having a ~20-fold increased production under low expression conditions tested.

Figure 11:
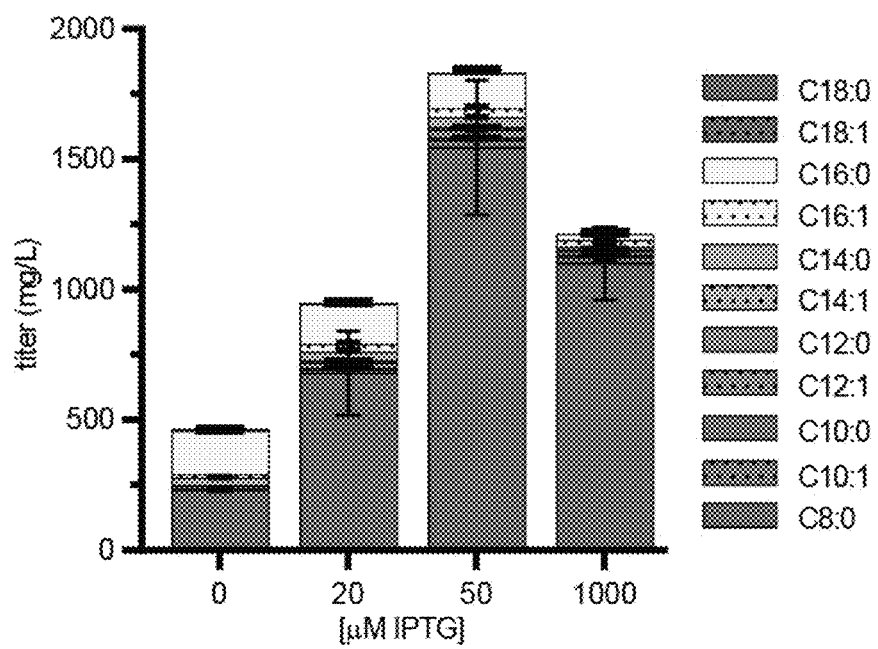

FIG. 11. Free fatty acid production from CpFatB1.2-M4-287 at different expression levels. CpFatB1.2-M4-287 was cloned into high copy plasmid ptrc99a, transformed into the RL08ara (ΔfadD) strain, grown in MOPS media (Kim et al. 2015) enriched with tryptone and yeast extract, and induced under different concentrations of IPTG. Under these conditions, 50 μM IPTG gave maximum octanoic acid production. At 1 mM IPTG, there was a growth defect that can be seen in the drastic decrease in C16 species.

Figure 12:
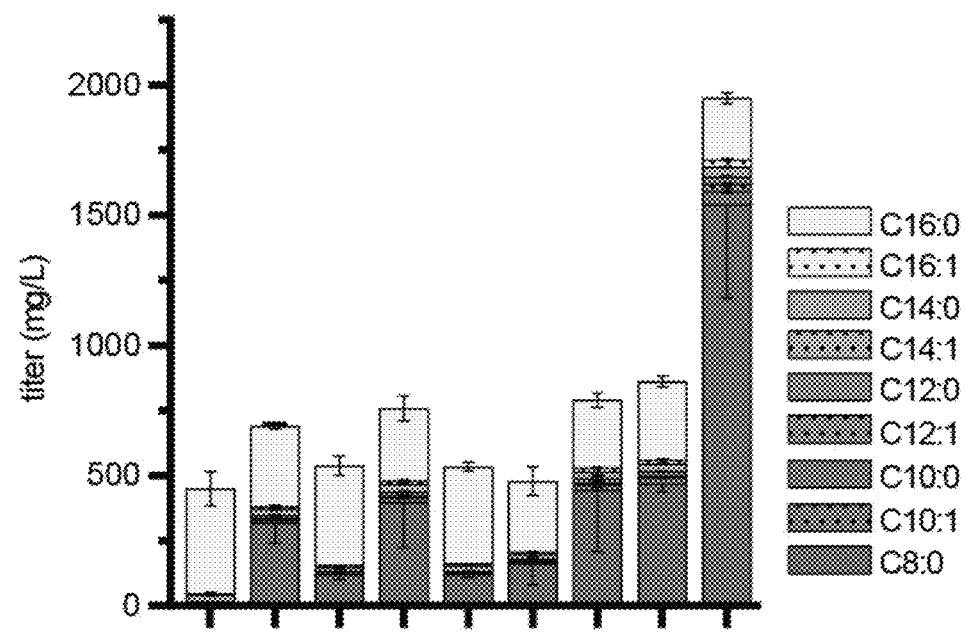

FIG. 12. Analysis of CpFatB1.2-M4-287 mutations. We made every single and double mutant combination contained in CpFatB1.2-M4-287 (N28S, I65M, 287-truncation) in the CpFatB1.2 base thioesterase and studied FFA production under the same conditions described for FIG. 10B. H224A is a catalytically inactive version of CpFatB1.2, which was used as a negative control. I65M was observed to have a minor contribution to activity as a single mutant. No significant additive effects were observed with double mutants. Only the triple mutant was able to outperform CpFatB1.2 drastically.

Figure 13A:
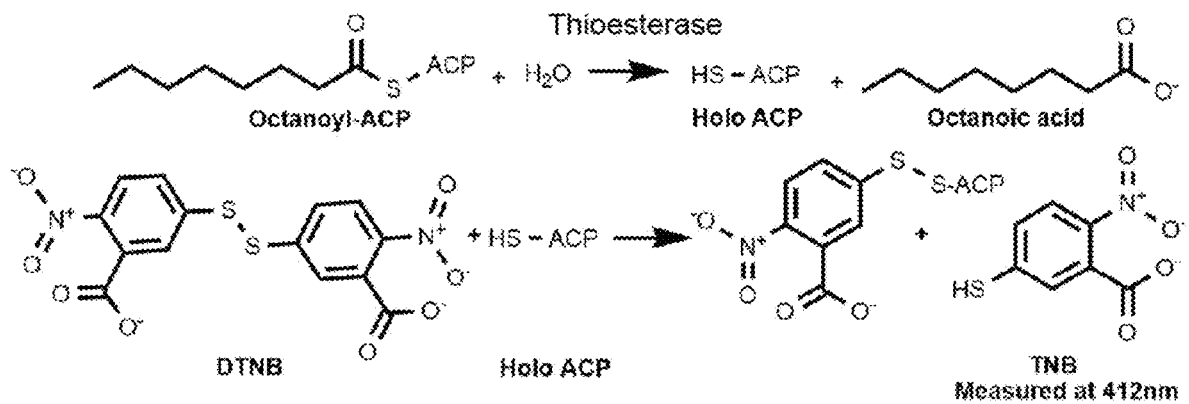

FIG. 13A. Scheme for octanoyl-ACP assay. Holo-ACP generated by thioesterase activity reacts with DTNB forming TNB compound with absorbance at 412 nm.

Figure 13B:
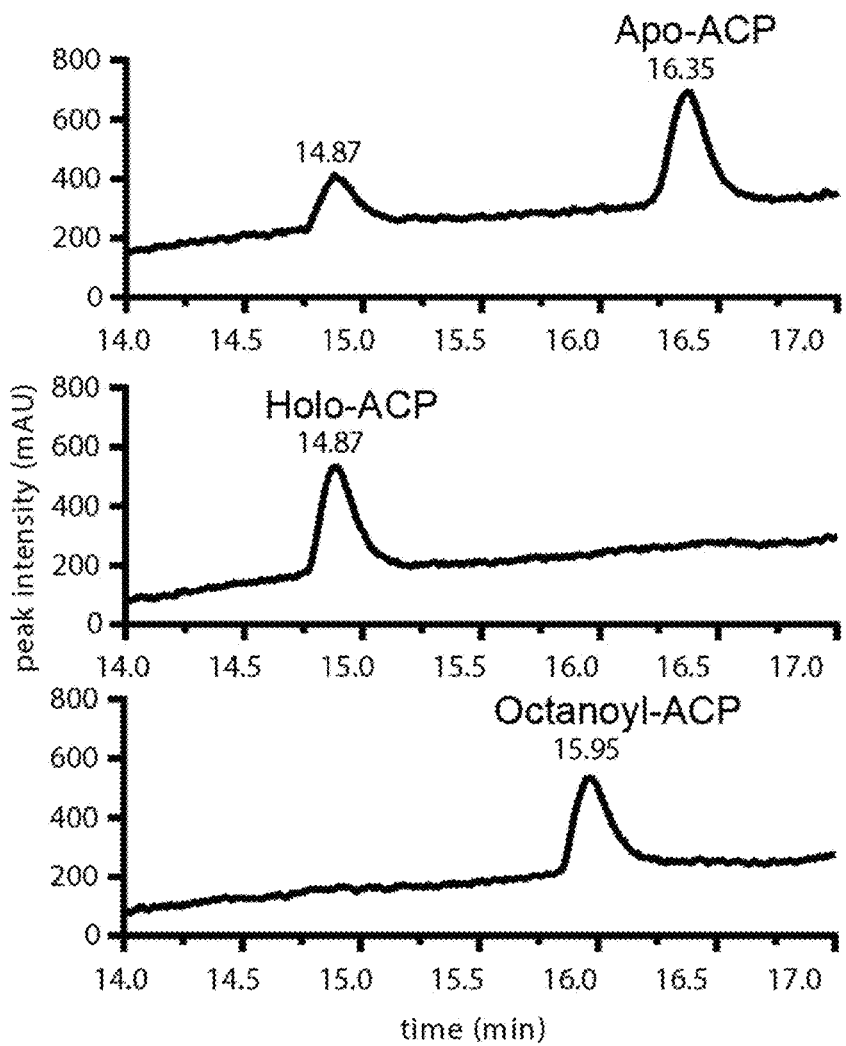

FIG. 13B. Verification of octanoyl-ACP synthesis. Shown are HPLC traces of apo-ACP and holo-ACP mixture as purified from E. coli (top); holo-ACP after incubation of E. coli mixture with Sfp (center); and octanoyl-ACP produced after incubation of holo-ACP with AasS (bottom).

Figures 13C, 13D:
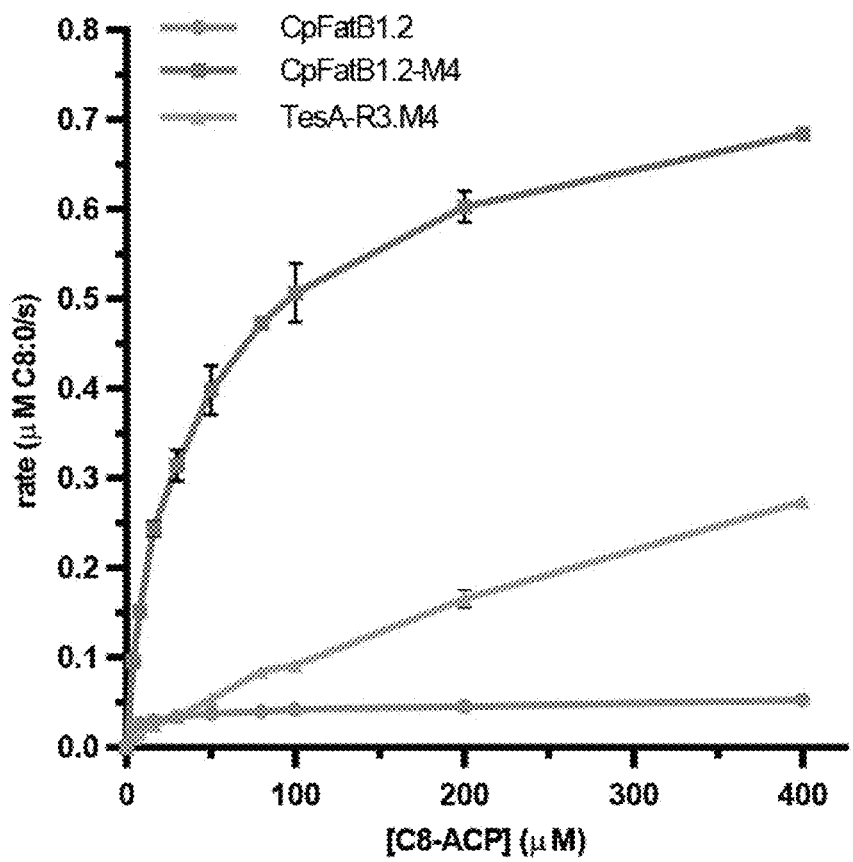

FIG. 13C. Activity of CpFatB1.2, CpFatB1.2-M4 and TesA-R3.M4 as a function of octanoyl-ACP concentration.

FIG. 13D. Kinetic parameters for each enzyme in FIG. 13C based on non-linear least squares fit of the curve.

Figure 14A:
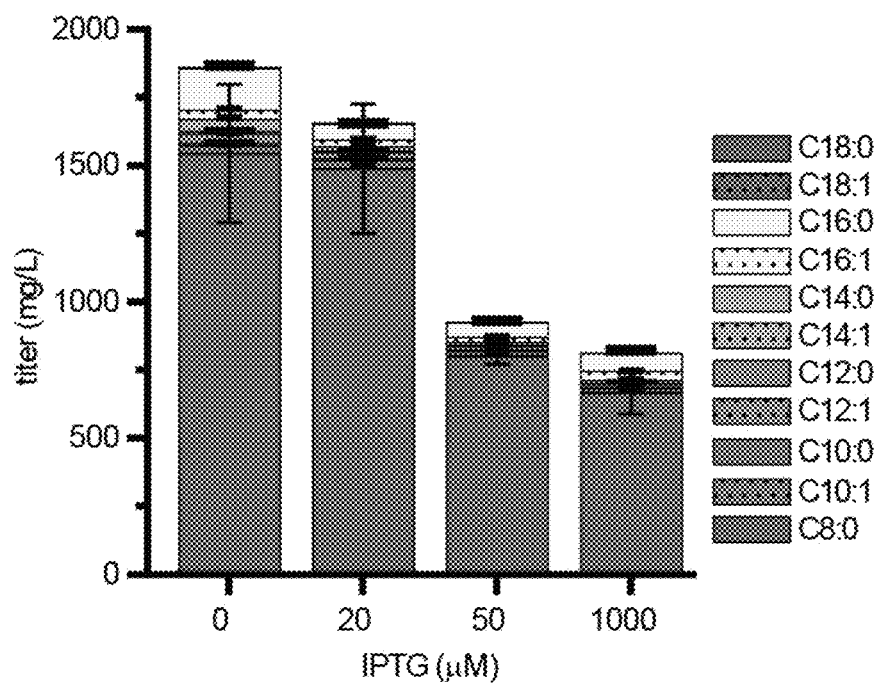

FIG. 14A. Free fatty acid production from CpFatB1.2-M4-287 expressed from a plasmid. CpFatB1.2-M4-287 was cloned into a pBTRCK plasmid with a strong RBS, transformed into the RL08ara (ΔfadD) strain, grown in MOPS media (Kim et al. 2015) enriched with tryptone and yeast extract, and induced with different concentrations of IPTG. Maximum production was achieved without induction with IPTG.

Figure 14B:
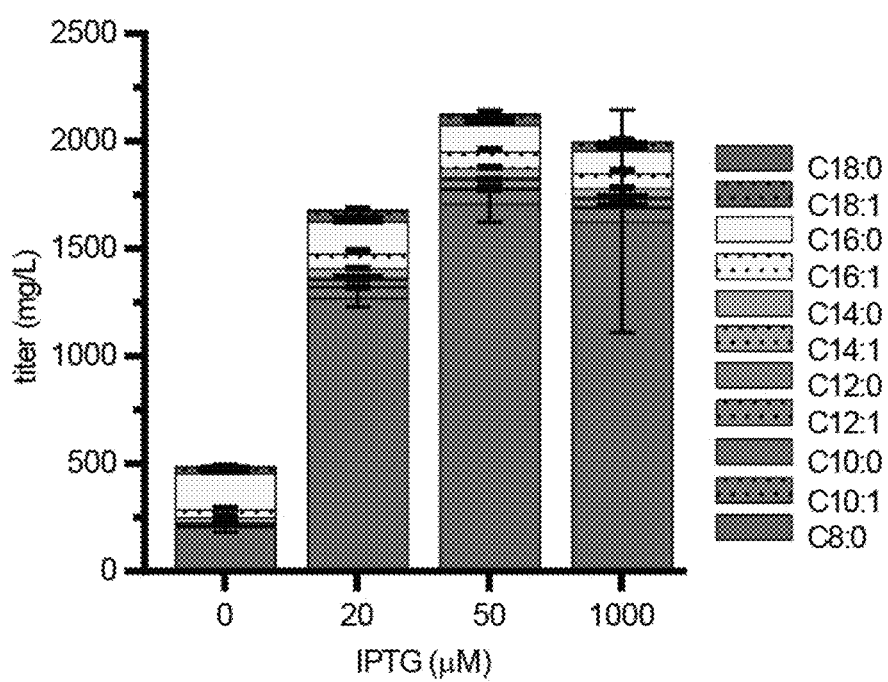

FIG. 14B. Free fatty acid production from CpFatB1.2-M4-287 expressed from the chromosome. Strain NHL17 (Escherichia coli K12 MG1655 ΔaraBAD ΔfadD::trc-CpFatB1.2-M4-287) was created to contain a single copy of a gene expressing CpFatB1.2-M4-287 and was tested for free fatty acid production under the same conditions described for FIG. 14A. NHL17, with a single copy of CpFatB1.2-M4-287 in the chromosome, was capable of making titers higher than that achieved from plasmids.

Figure 15A:
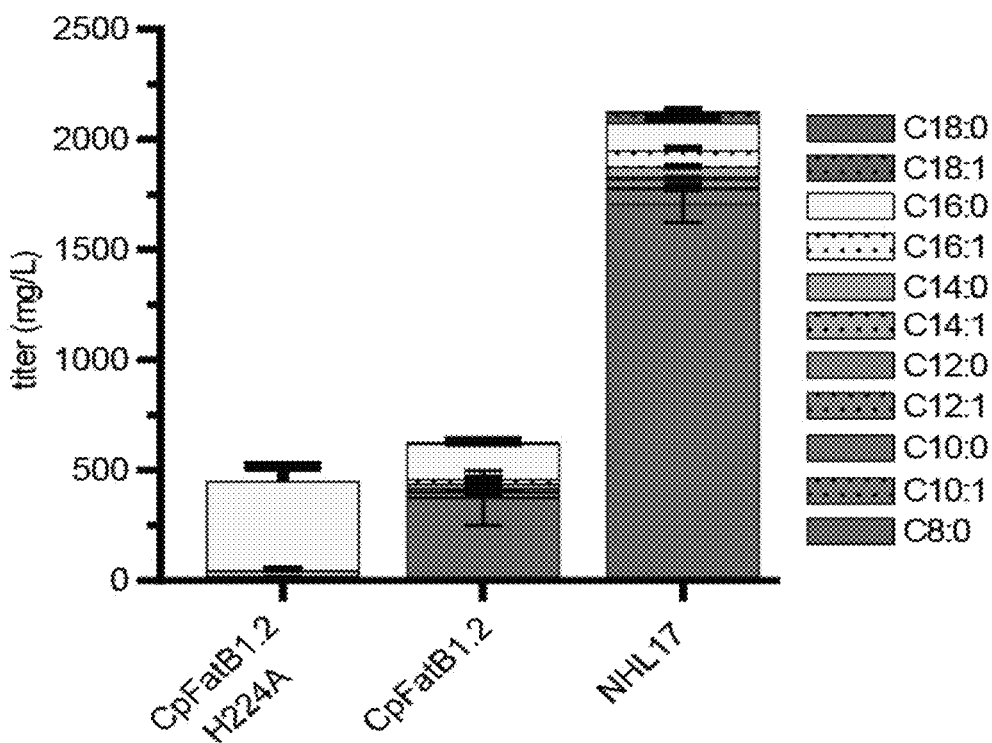
Figure 15B:
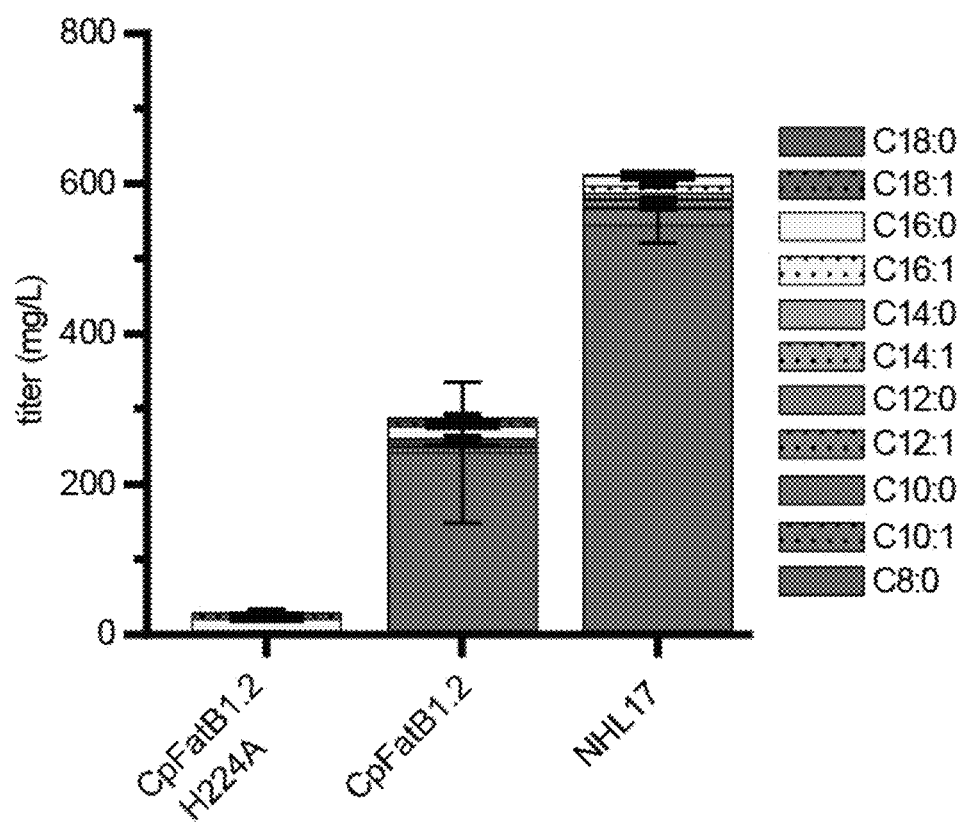

FIGS. 15A and 15B. Summary of highest titer achieved with CpFatB1.2 in high copy plasmid at maximum induction (CpFatB1.2) versus CpFatB1.2-M4-287 from a single copy in the chromosome (NHL17). FIG. 15A shows results from culturing in MOPS media enriched with tryptone and yeast extract. FIG. 15B shows results from culturing in MOPS minimal media with phosphate limitation.

Figure 16:
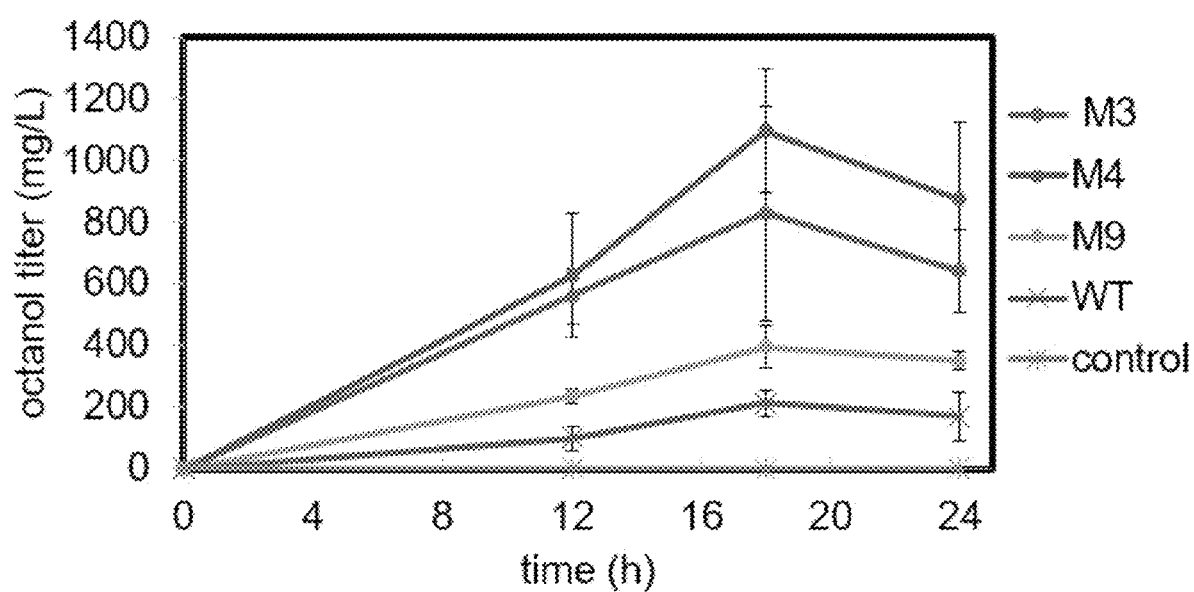

FIG. 16. Octanol production from *E. coli* strains co-expressing CpFatB1.2 variants, an acyl-CoA synthetase, and a hybrid acyl-CoA reductase/aldehyde reductase.

Figure 17A:
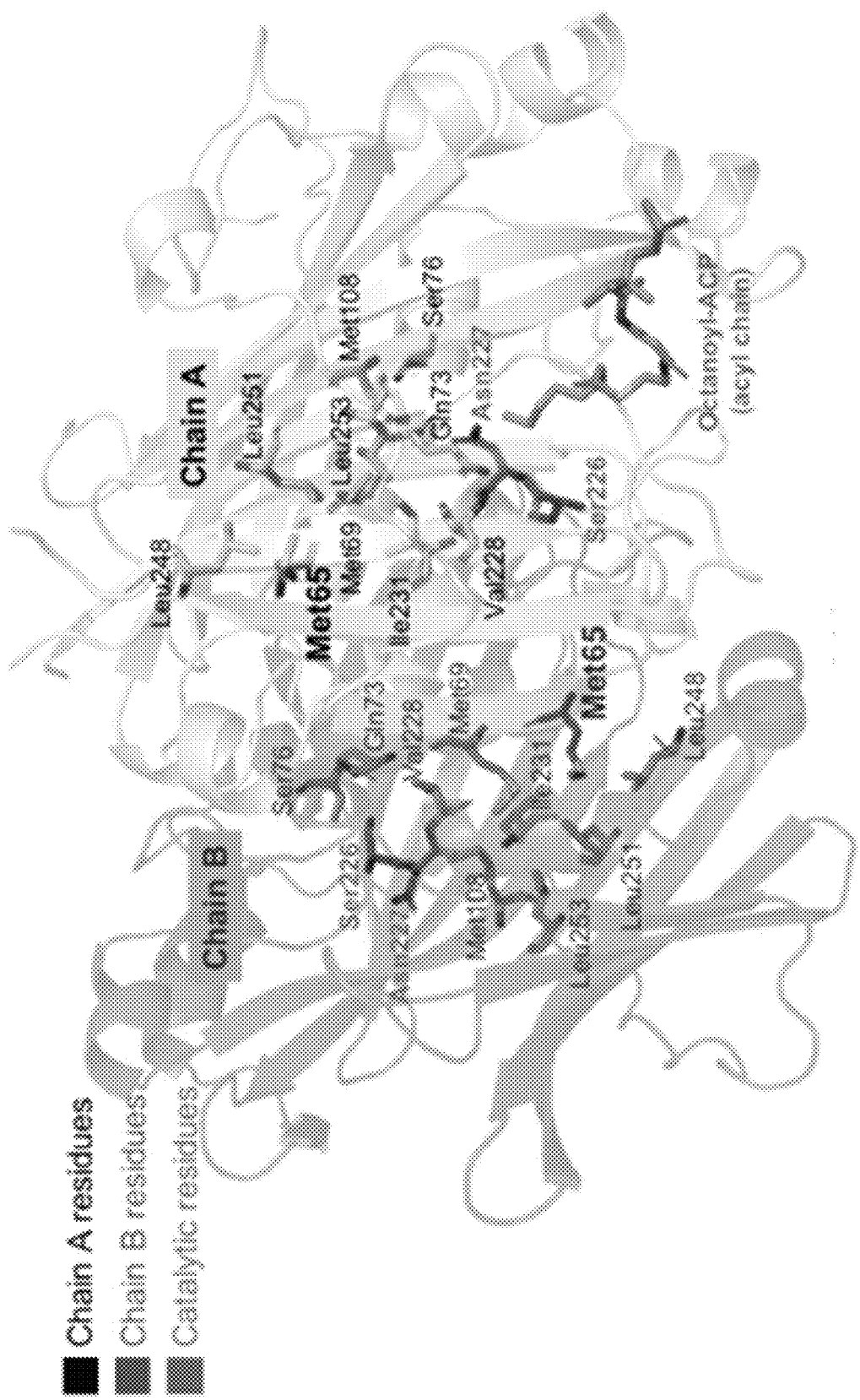
Figure 17B:
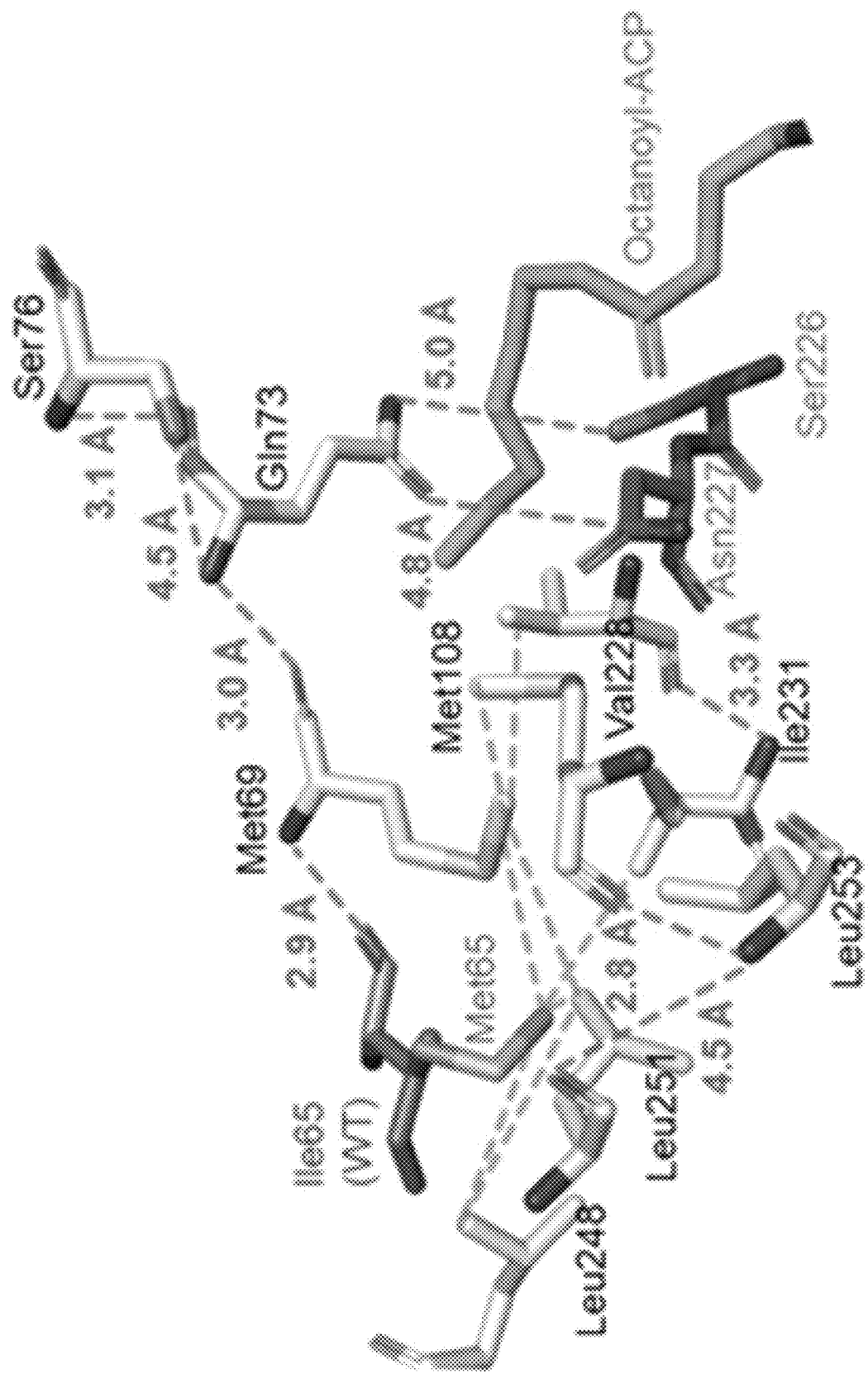
Figure 17C:
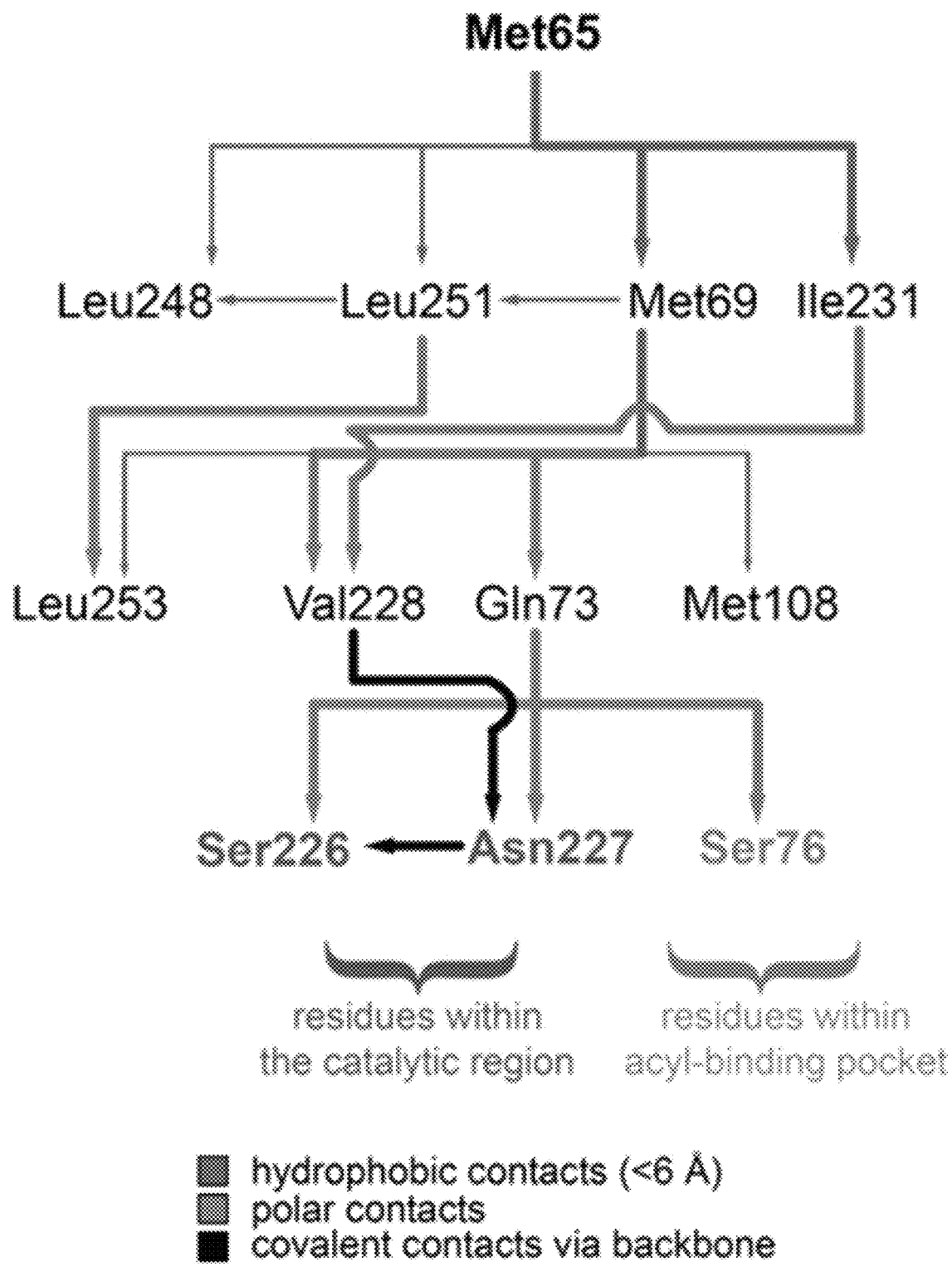

FIGS. 17A-17C. Effect of I65M mutation on CpFatB1.2-M4-287 mutant activity. FIG. 17A shows a structural overview of CpFatB1.2-M4-287 mutant. The mutated residues are shown in bold. The catalytic residues are marked in pink. The docked configuration of the substrate (blue) has been shown in one of the two (chain A) identical binding pockets present in two chains. FIG. 17B shows key residues that connect residue 65 to the acyl binding pocket. All the hydrophobic (pink dashes) and polar contacts (green dashes) have been overlaid on the CpFatB1.2-M4-287 mutant model. The polar distances have been labeled in green. FIG. 17C shows a contact map showing the trace of hydrophobic, polar, or covalent contacts from residue 65 to the catalytic region. The map terminates upon reaching one or more residues from the catalytic region (red) or the acyl binding-pocket (gray). Edge thickness correlates to importance of interactions.

Figure 18A:
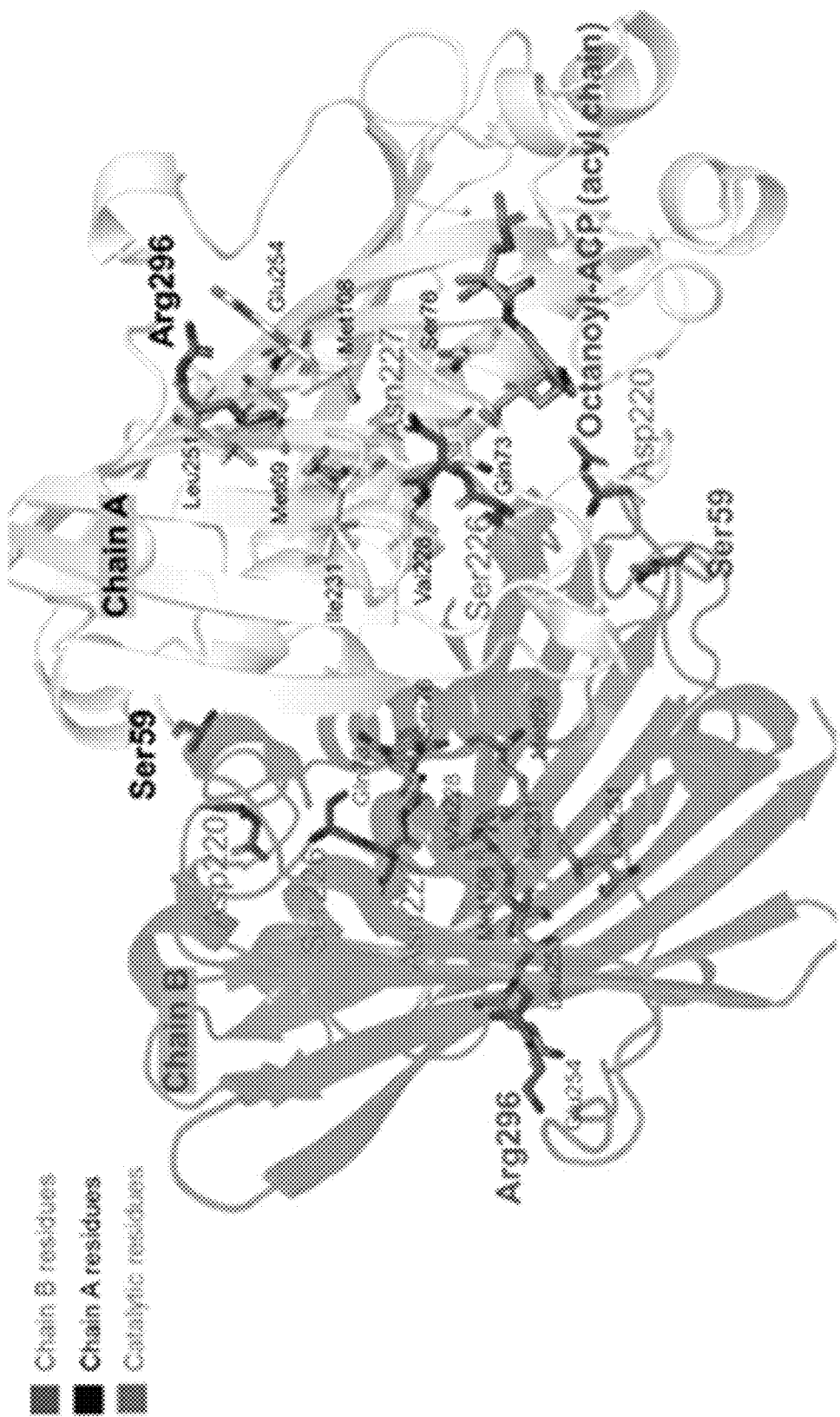
Figure 18B:
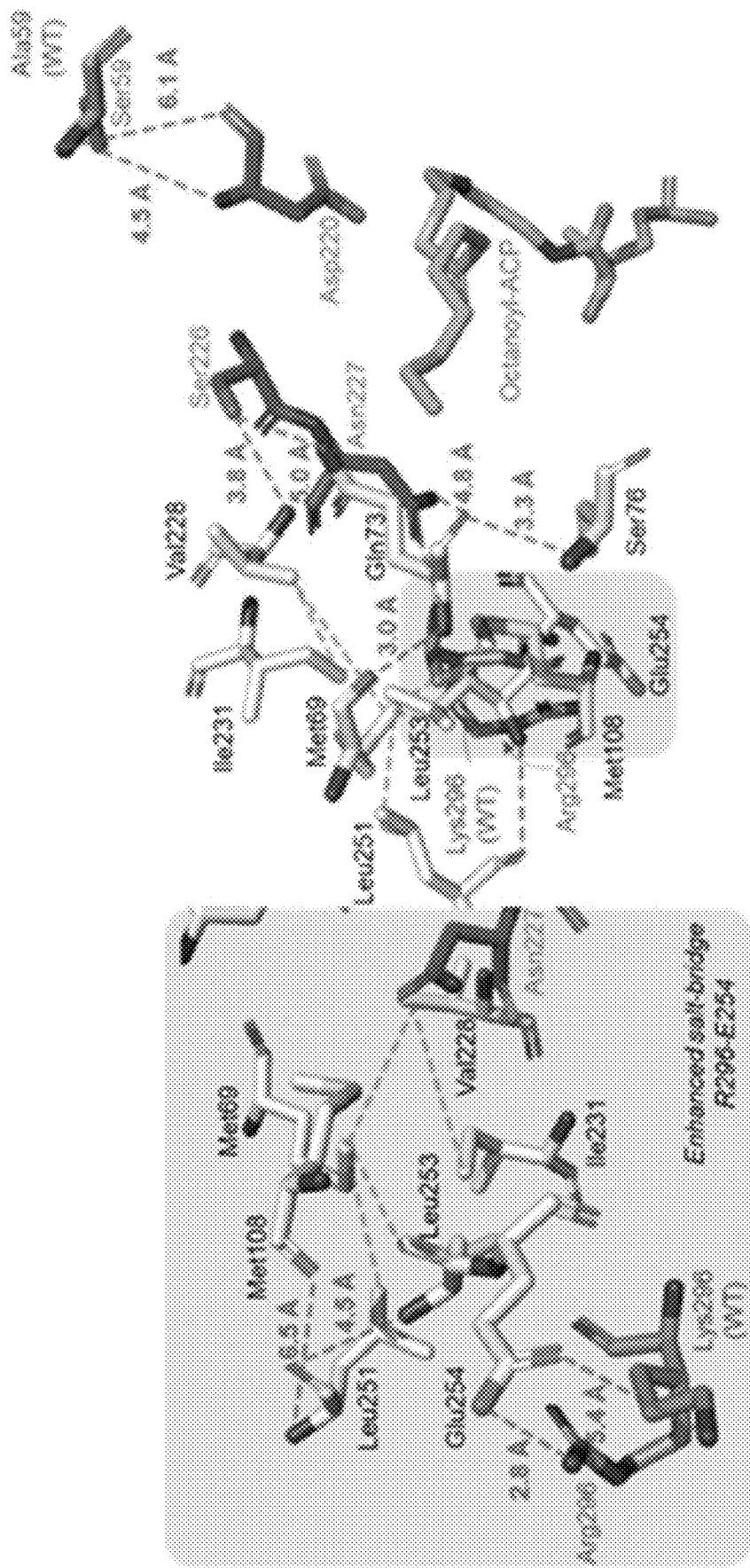
Figure 18C:
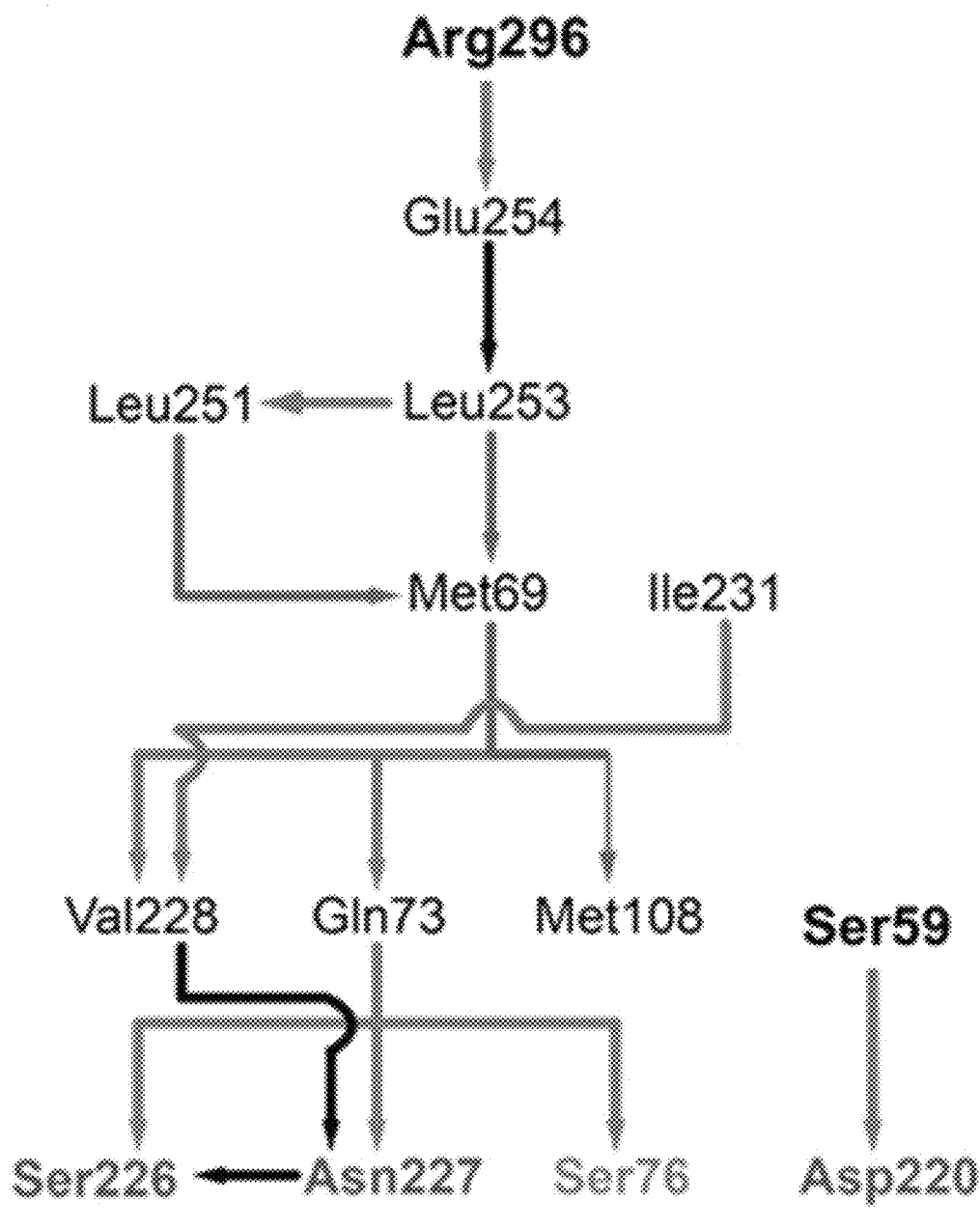

FIGS. 18A-18C. Effect of A59S and K296R mutations on CpFatB1.2-M3 mutant activity. FIG. 18A shows a structural overview of CpFatB1.2-M3 mutant. The mutated residues are shown in bold. The catalytic residues are marked in pink. The docked configuration of the substrate (blue) has been shown in one of the two (chain A) identical binding pockets present in two chains. FIG. 18B shows key residues that connect residues 59 and 296 to the acyl binding pocket. All the hydrophobic (pink dashes) and polar contacts (green dashes) have been overlaid on the CpFatB1.2-M3 mutant model. The polar distances have been labeled in green. The enhanced salt bridge formation between R296 and E254 has been shown inset. FIG. 18C shows a contact map showing the trace of hydrophobic (pink), polar (green), or covalent contacts (black) from residues 59 and 296 to the catalytic region. Edge thickness correlates to importance of interactions.

DETAILED DESCRIPTION OF THE INVENTION

One aspect of the invention is directed to mutant thioesterases. In some versions, the mutant thioesterases have enhanced activity with C8 substrates.

The mutant thioesterases may comprise an amino acid sequence at least about 30%, least about 40%, at least about 50%, at least about 60%, at least about 70%, at least about 70%, at least about 75%, at least about 80%, at least about 85%, at least about 90%, at least about 95%, at least about 97%, or at least about 99%, identical to positions 41-317, positions 40-317, positions 39-317, positions 38-317, positions 37-317, positions 36-317, positions 35-317, positions 34-317, positions 33-317, positions 32-317, positions 31-317, positions 30-317, positions 29-317, positions 28-317, positions 27-317, positions 26-317, positions 25-317, positions 24-317, positions 23-317, positions 22-317, positions 21-317, positions 20-317, positions 19-317, positions 18-317, positions 17-317, positions 16-317, positions 15-317, positions 14-317, positions 13-317, positions 12-317, positions 11-317, positions 10-317, positions 9-317, positions 8-317, positions 7-317, positions 6-317, positions 5-317, positions 4-317, positions 3-317, positions 2-317, or positions 1-317 of SEQ ID NO:4.

The mutant thioesterases may have one or more substitutions at positions corresponding to particular positions of SEQ ID NO:4. For example, the mutant thioesterases may comprise one or more of: a residue other than valine at a position corresponding to position 9 of SEQ ID NO:4; a residue other than lysine at a position corresponding to position 15 of SEQ ID NO:4; a residue other than tryptophan at a position corresponding to position 17 of SEQ ID NO:4; a residue other than lysine at a position corresponding to position 23 of SEQ ID NO:4; a residue other than asparagine at a position corresponding to position 28 of SEQ ID NO:4; a residue other than methionine at a position corresponding to position 29 of SEQ ID NO:4; a residue other than alanine at a position corresponding to position 59 of SEQ ID NO:4; a residue other than isoleucine at a position corresponding to position 65 of SEQ ID NO:4; a residue other than leucine at a position corresponding to position 86 of SEQ ID NO:4; a residue other than threonine at a position corresponding to position 117 of SEQ ID NO:4; a residue other than methionine at a position corresponding to position 136 of SEQ ID NO:4; a residue other than asparagine at a position corresponding to position 146 of SEQ ID NO:4; a residue other than glutamine at a position corresponding to position 163 of SEQ ID NO:4; a residue other than threonine at a position corresponding to position 204 of SEQ ID NO:4; a residue other than serine at a position corresponding to position 207 of SEQ ID NO:4; a residue other than glutamate at a position corresponding to position 236 of SEQ ID NO:4; a residue other than leucine at a position corresponding to position 251 of SEQ ID NO:4; a residue other than arginine at a position corresponding to position 261 of SEQ ID NO:4; a residue other than leucine at a position corresponding to position 265 of SEQ ID NO:4; a residue other than valine at a position corresponding to position 268 of SEQ ID NO:4; a residue other than arginine at a position corresponding to position 279 of SEQ ID NO:4; a residue other than aspartate at a position corresponding to position 293 of SEQ ID NO:4; a residue other than lysine at a position corresponding to position 296 of SEQ ID NO:4; and a residue other than asparagine at a position corresponding to position 309 of SEQ ID NO:4. The mutant thioesterases may have any one or more of the above-referenced substitutions in any combination.

The mutant thioesterases may comprise one or more of: a methionine or a conservative variant of methionine at the position corresponding to position 9 of SEQ ID NO:4; a glutamate or a conservative variant of glutamate at the position corresponding to position 15 of SEQ ID NO:4; an arginine or a conservative variant of arginine at the position corresponding to position 17 of SEQ ID NO:4; a glutamate or a conservative variant of glutamate at the position corresponding to position 23 of SEQ ID NO:4; a serine or a conservative variant of serine at the position corresponding to position 28 of SEQ ID NO:4; a threonine or a conservative variant of threonine at the position corresponding to position 29 of SEQ ID NO:4; a serine or a conservative variant of serine at the position corresponding to position 59 of SEQ ID NO:4; a methionine or a conservative variant of methionine at the position corresponding to position 65 of SEQ ID NO:4; a glutamine or a conservative variant of glutamine at the position corresponding to position 86 of SEQ ID NO:4; a serine or a conservative variant of serine at the position corresponding to position 117 of SEQ ID NO:4; a valine, an isoleucine, or a conservative variant of valine or isoleucine at the position corresponding to position 136 of SEQ ID NO:4; a lysine or a conservative variant of lysine at the position corresponding to position 146 of SEQ ID NO:4; a leucine or a conservative variant of leucine at the position corresponding to position 163 of SEQ ID NO:4; a serine or a conservative variant of serine at the position corresponding to position 204 of SEQ ID NO:4; a threonine or a conservative variant of threonine at the position corresponding to position 207 of SEQ ID NO:4; an alanine or a conservative variant of alanine at the position corresponding to position 236 of SEQ ID NO:4; a methionine or a conservative variant of methionine at the position corresponding to position 251 of SEQ ID NO:4; a serine or a conservative variant of serine at the position corresponding to position 261 of SEQ ID NO:4; an isoleucine or a conservative variant of isoleucine at the position corresponding to position 265 of SEQ ID NO:4; an isoleucine or a conservative variant of isoleucine at the position corresponding to position 268 of SEQ ID NO:4; a histidine or a conservative variant of histidine at the position corresponding to position 279 of SEQ ID NO:4; a valine or a conservative variant of valine at the position corresponding to position 293 of SEQ ID NO:4; an arginine or a conservative variant of arginine at the position corresponding to position 296 of SEQ ID NO:4; and an aspartate or a conservative variant of aspartate at the position corresponding to position 309 of SEQ ID NO:4. The mutant thioesterases may have any one or more of the above-referenced residues in any combination.

Some mutant thioesterases of the invention may comprise a residue other than asparagine at the position corresponding to position 28 of SEQ ID NO:4 and/or a residue other than isoleucine at the position corresponding to position 65 of SEQ ID NO:4. These mutant thioesterases may comprise a serine or a conservative variant of serine at the position corresponding to position 28 of SEQ ID NO:4 and/or a methionine or a conservative variant of methionine at the position corresponding to position 65 of SEQ ID NO:4.

Some mutant thioesterases of the invention may comprise a residue other than alanine at the position corresponding to position 59 of SEQ ID NO:4 and/or a residue other than lysine at the position corresponding to position 296 of SEQ ID NO:4. These mutant thioesterases may comprise a residue other than alanine at the position corresponding to position 59 of SEQ ID NO:4 and/or a residue other than lysine at the position corresponding to position 296 of SEQ ID NO:4.

Some mutant thioesterases of the invention may comprise a residue other than aspartate at the position corresponding to position 293 of SEQ ID NO:4. These mutant thioesterases may comprise a valine or a conservative variant of valine at the position corresponding to position 293 of SEQ ID NO:4.

Some mutant thioesterases of the invention may comprise a residue other than lysine at the position corresponding to position 296 of SEQ ID NO:4. These mutant thioesterases may comprise an arginine or a conservative variant of arginine at the position corresponding to position 296 of SEQ ID NO:4.

Some mutant thioesterases of the invention may comprise a residue other than arginine at the position corresponding to position 261 of SEQ ID NO:4. These mutant thioesterases may comprise a serine or a conservative variant of serine at the position corresponding to position 261 of SEQ ID NO:4.

The mutant thioesterases may lack various N-terminal portions characteristic of various natural thioesterases. The mutant thioesterases, for example, may lack an N-terminal portion having amino acid sequence identical to positions 1-10, positions 1-20, positions 1-30, positions 1-40, positions 1-50, positions 1-60, positions 1-65, positions 1-70, positions 1-75, positions 1-80, positions 1-81, positions 1-82, positions 1-83, positions 1-84, positions 1-85, positions 1-86, positions 1-87, positions 1-88, positions 1-89, positions 1-90, positions 1-91, positions 1-92, positions 1-93, or positions 1-94 of SEQ ID NO:2. The mutant thioesterases may lack an N-terminal portion having an amino acid sequence identical to positions 1-2, positions 1-3, positions 1-4, positions 1-5, positions 1-6, positions 1-7, positions 1-8, positions 1-9, positions 1-10, positions 1-11, positions 1-12, positions 1-13, positions 1-14, positions 1-15, positions 1-16, positions 1-17, or positions 1-18 of SEQ ID NO:4. The N-terminal portions are lacking at positions N-terminal (i.e., closer to the N-terminus) of the amino acid sequence at least about 30%, least about 40%, at least about 50%, at least about 60%, at least about 70%, at least about 70%, at least about 75%, at least about 80%, at least about 85%, at least about 90%, at least about 95%, at least about 97%, or at least about 99%, identical to positions 41-317, positions 40-317, positions 39-317, positions 38-317, positions 37-317, positions 36-317, positions 35-317, positions 34-317, positions 33-317, positions 32-317, positions 31-317, positions 30-317, positions 29-317, positions 28-317, positions 27-317, positions 26-317, positions 25-317, positions 24-317, positions 23-317, positions 22-317, positions 21-317, positions 20-317, positions 19-317, positions 18-317, positions 17-317, positions 16-317, positions 15-317, positions 14-317, positions 13-317, positions 12-317, positions 11-317, positions 10-317, positions 9-317, positions 8-317, positions 7-317, positions 6-317, positions 5-317, positions 4-317, positions 3-317, positions 2-317, or positions 1-317 of SEQ ID NO:4.

The mutant thioesterases of the invention may be derived from a precursor thioesterase, wherein each of the mutants (or the naturally-occurring equivalents) has at least one altered property in vitro and/or in vivo, as compared to the properties of the precursor thioesterase. The altered property preferably comprises an enhancement of an aspect of thioesterase activity. The altered property may include increased thioesterase activity with medium-chain substrates, such as C8 substrates. The altered property may comprise an increase in selectivity or catalytic rate in hydrolyzing a medium-chain acyl-acyl carrier protein (ACP) substrate or a medium-chain acyl-CoA substrate to yield a free fatty acid or a free fatty acid derivative. The altered property may comprise an increase in selectivity or catalytic rate in hydrolyzing a C8-ACP substrate or a C8 acyl-CoA substrate to yield a free fatty acid or a free fatty acid derivative. An exemplary precursor thioesterase is *Cuphea palustris* FatB1 thioesterase (CpFatB1) represented by SEQ ID NO:1 (nucleotide coding sequence) and SEQ ID NO:2 (protein sequence).

Another aspect of the invention is a polynucleotide (or a gene) encoding a mutant thioesterase of the invention. Another aspect of the invention is a vector comprising the polynucleotide (or the gene) according to the invention. Vectors of the invention can be transformed into suitable host cells to produce recombinant host cells.

Another aspect of the invention is a recombinant host cell comprising a polynucleotide encoding a mutant thioesterase or a naturally-occurring equivalent thereof. In some versions, known genomic alteration or modification techniques can be employed to alter or modify the endogenous thioesterases of the host cell, effectuating one or more of the aforementioned mutations, such that at least one of the mutant endogenous thioesterases has at least one altered property. In other versions, the recombinant host cell is engineered to include a plasmid comprising a polynucleotide encoding a mutant thioesterase. In yet other versions, the recombinant host cell is engineered to include the polynucleotide encoding the mutant thioesterase integrated into the chromosome of the host cell.

The recombinant host cell of the invention can be selected from any cell capable of expressing a recombinant gene construct, and can be selected from a microbial, plant or animal cell. In a particular embodiment, the host cell is bacterial, cyanobacterial, fungal, yeast, algal, human or mammalian in origin. In a particular embodiment, the host cell is selected from any of Gram positive bacterial species such as Actinomycetes; Bacillaceae, including *Bacillus alkalophilus, Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, B. thuringiensis; Brevibacteria* sp., including *Brevibacterium flavum, Brevibacterium lactofermentum, Brevibacterium ammoniagenes, Brevibacterium butanicum, Brevibacterium divaricatum, Brevibacterium healii, Brevibacterium ketoglutamicum, Brevibacterium ketosoreductum, Brevibacterium lactofermentum, Brevibacterium linens, Brevibacterium paraffinolyticum; Corynebacterium* spp. such as *C. glutamicum* and *C. melassecola, Corynebacterium herculis, Corynebacterium lilium, Corynebactertium acetoacidophilum, Corynebacterium acetoglutamicum, Corynebacterium acetophilum, Corynebacterium ammoniagenes, Corynebacterium fujiokense, Corynebacterium nitrilophilus*; or lactic acid bacterial species including *Lactococcus* spp. such as *Lactococcus lactis; Lactobacillus* spp. including *Lactobacillus reuteri; Leuconostoc* spp.; *Pediococcus* spp.; *Serratia* spp. such as *Serratia marcescens; Streptomyces* species, such as *Streptomyces lividans, Streptomyces murinus, S. coelicolor* and *Streptococcus* spp. Alternatively, strains of a Gram negative bacterial species belonging to Enterobacteriaceae including *E. coli, Cellulomonas* spp.; or to Pseudomonadaceae including *Pseudomonas aeruginosa, Pseudomonas alcaligenes, Pseudomonas fluorescens, Pseudomonas putida, Pseudomonas syringae* and *Burkholderia cepacia, Salmonella* sp., *Stenotrophomonas* spp., and *Stenotrophomonas maltophilia*. Oleaginous microorganisms such as *Rhodococcus* spp, *Rhodococcus opacus, Ralstonia* spp., and *Acetinobacter* spp. are useful as well. Furthermore, yeasts and filamentous fungal strains can be useful host cells, including *Absidia* spp.; *Acremonium* spp.; *Agaricus* spp.; *Anaeromyces* spp.; *Aspergillus* spp., including *A. aculeatus, A. awamori, A. flavus, A. foetidus, A. fumaricus, A. fumigatus, A. nidulans, A. niger, A. oryzae, A. terreus; A. tubingensis* and *A. versicolor; Aeurobasidium* spp.; *Cephalosporum* spp.; *Chaetomium* spp.; *Coprinus* spp.; *Dactyllum* spp.; *Fusarium* spp., including *F. conglomerans, F. decemcellulare, F. javanicum, F. lini, F. oxysporum* and *F. solani; Gliocladium* spp.; *Kluyveromyces* sp.; *Hansenula* sp.; *Humicola* spp., including *H. insolens* and *H. lanuginosa; Hypocrea* spp.; *Mucor* spp.; *Neurospora* spp., including *N. crassa* and *N. sitophila; Neocallimastix* spp.; *Orpinomyces* spp.; *Penicillium* spp.; *Phanerochaete* spp.; *Phlebia* spp.; *Pichia* sp.; *Piromyces* spp.; *Rhizopus* spp.; *Rhizomucor* species such as *Rhizomucor miehei; Saccaromyces* species such as *S. cerevisiae, S. pastorianus, S. eubayanus*, and *S. fragilis; Schizophyllum* spp.; *Schizosaccharomyces* such as, for example, *S. pombe* species; *chytalidium* sp., *Sulpholobus* sp., *Thermoplasma* sp., *Thermomyces* sp.; *Trametes* spp.; *Trichoderma* spp., including *T. reesei, T. reesei* (*longibrachiatum*) and *T. viride; Yarrowinia* sp.; and *Zygorhynchus* spp and in particular include oleaginous yeast just *Phafia* spp., *Rhorosporidium toruloides* Y4, *Rhodotorula Glutinis* and *Candida* 107.

In some versions of the invention, a recombinant host cell is provided, which expresses or overexpresses a gene encoding the mutant thioesterase, and which also expresses (or overexpresses) one or more genes encoding one or more enzymes that utilize, as substrates, reaction products of the mutant thioesterase (e.g., fatty acids, fatty acyl-CoAs, fatty acyl-phosphate esters, fatty aldehydes, fatty esters, or fatty alcohols) or reaction products of one or more other enzymes that are parts of a metabolic pathway, including reaction products of the mutant thioesterase (e.g., fatty acids) as precursors and/or substrates.

In one embodiment of the invention, a recombinant host cell is provided, which expresses or overexpresses a gene encoding a mutant thioesterase and which also expresses (or overexpresses) one or more genes encoding one or more enzymes that react with a substrate that is necessary as a precursor to a reaction in a fatty acid biosynthetic pathway. In a particular embodiment, the recombinant host cell includes a gene that encodes a thioesterase and a gene that encodes an enzyme that reacts with a substrate that is necessary as a precursor to a reaction in a fatty acid synthetic pathway, which comprises the overexpression or modification of a gene selected from pdh, panK, aceEF, fabH, fabD, fabG, acpP, fadR, accABCD, fabI, fabA, fabB, fabF, and/or any homologs thereof.

In some versions of the invention, the recombinant host cell comprises a gene (or a polynucleotide) that encodes a mutant thioesterase and also comprises the attenuation or deletion of a gene that reduces carbon flux, or a gene that competes for substrates, cofactors, or energy requirements within a fatty acid biosynthetic pathway. In a particular embodiment, the attenuated gene comprises at least one of fadE, gpsA, IdhA, pflB, adhE, pta, poxB, ackA, ackB, plsB, ldh, glta, sfa, and/or any homologs thereof.

In some versions of the invention, a recombinant host cell comprises a gene (or a polynucleotide) encoding a mutant thioesterase and a heterologously-introduced exogenous gene encoding at least one fatty acid derivative enzyme. In certain embodiments, the exogenous gene or polynucleotide encodes, for example, an acyl-CoA synthase, a wax/ester synthase, an alcohol acyltransferase, an alcohol dehydrogenase, an acyl-CoA reductase, an acyl-ACP reductase, a fatty-alcohol-forming acyl-CoA reductase, an alcohol O-acyltransferase, an aldehyde deformylating oxygenase, a fatty-acid O-methyltransferase, a carboxylic acid reductase, a decarboxylase, an aldehyde reductase, a fatty alcohol acetyl transferase, an acyl condensing enzyme, an aminotransferase, and/or a decarbonylase.

In some versions of the invention, a gene encoding the mutant thioesterase and/or a fatty acid derivative enzyme, for example, an acyl-CoA synthase, a wax/ester synthase, an alcohol acyltransferase, an alcohol dehydrogenase, an acyl-CoA reductase, an acyl-ACP reductase, a fatty-alcohol-forming acyl-CoA reductase, an alcohol O-acyltransferase, an aldehyde deformylating oxygenase, a fatty-acid O-methyltransferase, a carboxylic acid reductase, a decarboxylase, an aldehyde reductase, a fatty alcohol acetyl transferase, an acyl condensing enzyme, an aminotransferase, a polyhydroxyalkanoate (PHA) synthase, and/or a decarbonylase, is overexpressed.

In some versions of the invention, genes encoding mutant thioesterases, fatty acid derivative enzymes and/or other recombinantly expressed genes in a recombinant host cell are modified to optimize at least one codon for expression in the recombinant host cell.

In some versions of the invention, the recombinant host cell comprises at least one gene encoding a mutant thioesterase and a gene encoding an acyl-CoA synthase. The acyl-CoA synthase gene can be any of fadD, fadK, BH3103, yhfL, pfl-4354, EAV15023, fadD1, fadD2, RPC_4074, fadDD35, fadDD22, faa3p, or the gene encoding the protein ZP_01644857. Other examples of acyl-CoA synthase genes include fadDD35 from *M. tuberculosis* HR7Rv [NP_217021], yhfL from *B. subtilis* [NP_388908], fadD1 from *P. aeruginosa* PAO1 [NP_251989], the gene encoding the protein ZP_01644857 from *Stenotrophomonas maltophilia* R551-3, or faa3p from *Saccharomyces cerevisiae* [NP_012257]. Other examples are described elsewhere herein.

In some versions of the invention, a recombinant host cell is provided comprising at least one gene or polynucleotide encoding a mutant thioesterase (and a gene or polynucleotide encoding an ester synthase, such as an ester synthase gene obtained from *Acinetobacter* spp., *Alcanivorax borkumensis, Arabidopsis thaliana, Saccharomyces cerevisiae, Homo sapiens, Simmondsia chinensis, Mortierella alpina, Cryptococcus curvatus, Alcanivorax jadensis, Alcanivorax borkumensis, Acinetobacter* sp. HO1-N, or *Rhodococcus opacus*. Examples of ester synthase genes include wax/dgat, encoding a bifunctional ester synthase/acyl-CoA: diacylglycerol acyltransferase from *Simmondsia chinensis, Acinetobacter* sp. strain ADPJ, *Alcanivorax borkumensis, Pseudomonas aeruginosa, Fundibacter jadensis, Arabidopsis thaliana*, or *Alkaligenes eutrophus*. The gene encoding the ester synthase may be overexpressed.

In some versions of the invention, the recombinant host cell comprises at least one gene encoding a fatty aldehyde biosynthetic enzyme. A fatty aldehyde biosynthetic gene can be, for example, a carboxylic acid reductase gene (e.g., a car gene).

In some versions of the invention, the recombinant host cell comprises at least one fatty alcohol production gene. Fatty alcohol production genes include, for example, fatty acyl-CoA reductases such as acrl or the fatty acyl-CoA reductase from *Marinobacter aquaeolei* VT8 (Robert M. Willis, Bradley D. Wahlen, Lance C. Seefeldt, and Brett M. Barney. Characterization of a Fatty Acyl-CoA Reductase from Marinobacter aquaeolei VT8: A Bacterial Enzyme Catalyzing the Reduction of Fatty Acyl-CoA to Fatty Alcohol. *Biochemistry* 2011 50 (48), 10550-10558). Other fatty alcohol production genes are described in, for example, PCT Publication Nos. 2008/119082 and 2007/136762, the disclosures of which are herein incorporated by reference. Other examples are provided elsewhere herein.

In some versions of the invention, the recombinant host cell comprises a gene encoding a mutant thioesterase and a gene encoding at least one olefin producing gene. The gene may be a terminal olefin producing gene or an internal olefin producing gene. As examples of terminal olefin producing genes, those described in PCT Publication No. 2009/085278, including orf880, are appropriate. As examples of internal olefin producing genes, those described in PCT Publication No. 2008/147781 A2 are appropriate. The disclosures of PCT Publication Nos. 2009/085278 and 2008/147781 A2 are herein incorporated by reference.

In some versions of the invention, a recombinant host cell is provided comprising at least one gene or polynucleotide encoding a mutant thioesterase, and at least one of (a) a gene or polynucleotide encoding a fatty acid derivative enzyme and (b) a gene or polynucleotide encoding an acyl-CoA dehydrogenase enzyme that is attenuated. Preferably that gene encoding a fatty acid derivative enzyme that is attenuated or deleted is endogenous to the host cell, encoding, for example, an acyl-CoA synthase, a wax/ester synthase, an alcohol acyltransferase, an alcohol dehydrogenase, an acyl-CoA reductase, an acyl-ACP reductase, a fatty-alcohol-forming acyl-CoA reductase, an alcohol O-acyltransferase, an aldehyde deformylating oxygenase, a fatty-acid O-methyltransferase, a carboxylic acid reductase, a decarboxylase, an aldehyde reductase, a fatty alcohol acetyl transferase, an acyl condensing enzyme, an aminotransferase, and/or a decarbonylase. In one embodiment, the attenuated gene encodes an acyl-CoA synthase or an ester synthase.

In some versions of the invention, the recombinant host cell has an endogenous gene encoding an acyl-CoA dehydrogenase enzyme that is deleted or attenuated.

In some versions of the invention, a method is provided wherein the recombinant host cell according to the invention is cultured under conditions that permit expression or overexpression of a mutant thioesterases of the invention. The mutant thioesterase can be recovered, and more preferably substantially purified, after the host cell is harvested and/or lysed.

In some versions of the invention, a method is provided wherein the recombinant host cell according to the invention is cultivated under conditions that permit production of fatty acid derivatives. In a preferred embodiment, the fatty acid derivative can be recovered, and more preferably the fatty acid derivative is substantially purified. In a particularly preferred embodiment, the fatty acid derivative composition is substantially purified from other components produced during cultivation by centrifugation.

In some versions of the invention, a method is provided for producing a fatty acid derivative, comprising cultivating a recombinant host cell of the invention under conditions suitable to ensure expression or overexpression of a mutant thioesterase, and recovering the fatty acid derivative that is produced.

In some versions of the invention, a method is provided for extracellularly producing a fatty acid derivative in vitro, comprising cultivating a recombinant host cell under conditions suitable for expression or overexpression of a mutant thioesterase of the invention, harvesting the cells, and lysing the cells, such that the thioesterase enzyme that is produced can be recovered and used to produce fatty acid derivatives in vitro. In an exemplary embodiment, the mutant thioesterase is substantially purified. In another exemplary embodiment, the mutant thioesterase is not purified from the cell lysate. The purified mutant thioesterase enzyme or the cell lysate comprising such an enzyme can then be subject to suitable thioesterase substrates under conditions that allow the production of fatty acid derivatives extracellularly. Techniques for introducing substrates to enzymes are well known in the art. A non-limiting example is adding the substrate(s) in a solution form to the enzyme solution or the cell lysate, and allowing the mixture to incubate. Another non-limiting example involves incubating the substrate(s) and enzyme solution or cell lysate by either attaching the substrate(s) or the enzyme to a solid medium (e.g., beads, resins, plates, etc.) and passing the enzyme solution/lysate or the substrate(s), respectively, through the solid medium in a speed that allows for sufficient contact between the substrate(s) and the enzyme.

In some versions of the invention, a method is provided for producing a fatty acid derivative, which comprises cultivating a recombinant host cell under conditions suitable to ensure expression of the mutant thioesterase, and recovering the fatty acid derivative that is secreted or released extracellularly. Accordingly, the fatty acid derivative product is recovered from, for example, the supernatant of a cultivation broth wherein the host cell is cultured.

In some versions of the invention, a method is provided for obtaining a fatty acid derivative composition extracellularly by cultivating a recombinant host cell that has been transformed with a polynucleotide encoding a mutant thioesterase, cultivating under conditions that permit production of a fatty acid derivative, a major or minor portion of which is secreted or released extracellularly, and recovering the fatty acid derivative that is produced. In an exemplary embodiment, the fatty acid derivative is produced within the cell, but a portion of it is released by the host cell. Accordingly, the method further comprises harvesting the cells, lysing the cells, and recovering the fatty acid derivative.

In some versions of the invention, a method of producing fatty acid derivatives is provided comprising: transforming the host cell with a polynucleotide sequence encoding a mutant thioesterase, such that the production of fatty acid derivatives in the host cell is altered relative to a cell that has not been transformed with the mutant thioesterase gene.

In some versions of the invention, a method of producing fatty acid derivatives is provided comprising: providing a polynucleotide sequence comprising a gene encoding a mutant thioesterase; transforming a suitable host cell under conditions wherein said polynucleotide sequence is incorporated into said chromosome of said cell and said gene is expressible within said host cell; cultivating the transformed host cell under conditions suitable for said host cell to express said gene and produce a mutant thioesterase protein; and recovering the fatty acid derivatives.

In any of the embodiments above, derivatives of a certain carbon chain length can be recovered at a greater proportional yield, in comparison with the production of such fatty acid derivatives of the same carbon chain length in the same host cell in the absence of the mutant thioesterase. In a particular embodiment, the fatty acid derivatives that are recovered at an increased or decreased yield comprise a primary chain length of a C8 fatty acyl chain. The fatty acid derivatives that are recovered at an increased or decreased yield in the composition can be selected from all types of fatty acid derivatives, including, for example, hydrocarbons, fatty acids, fatty esters, fatty aldehydes, fatty alcohols terminal olefins, internal olefins, alkanes, diols, fatty amines, dicarboxylic acids, polyhydroxyalkanoates, or ketones, or combinations thereof.

Alternatively, in any of the embodiments above, a particular fatty acid derivative can be produced at an increased or decreased proportional or percentage yield relative to the other fatty acid derivatives, when compared to the proportional or percentage yield of that particular fatty acid derivative in the same host cell in the absence of the mutant thioesterase.

In some versions of the invention, fatty acid derivative compositions are provided that are produced by the host cells of the invention. Such compositions can comprise hydrocarbons, esters, alcohols, ketones, aldehydes, fatty acids, dicarboxylic acids, internal olefins, terminal olefins, polyhydroxyalkanoates, and/or combinations thereof. Such compositions are useful in applications in the chemical industry, for example in the production of surfactants and detergents, or as a biofuel and a substitute for petroleum, heating oil, kerosene, diesel, jet fuel or gasoline.

In a particular version, the fatty acid derivative composition comprises C8 (i.e., a carbon chain length of 8 carbons) fatty esters, C8 fatty acids, C8 fatty aldehydes, C8 fatty alcohols, or polyhydroxyalkanoates with C8 side chains.

In a particular version, the fatty acid derivatives of the invention comprise straight chain fatty acid derivatives, branched chain fatty acid derivatives, and/or cyclic moieties. In a particular embodiment, the fatty acid derivatives are unsaturated (e.g., monounsaturated) or saturated.

In some versions of the invention, the fatty acid derivative composition includes octanoic acid.

Another aspect of the invention is directed to a method of screening thioesterase mutants for C8 thioesterase activity. The method comprises, introducing a gene encoding a mutant thioesterase in a microorganism lacking lipB, incubating the microorganism in a medium devoid of lipoic acid and octanoic acid, and recovering the microorganism after growth in the medium. As shown in the examples, the method can be used to screen for thioesterases having enhanced C8 thioesterase activity from a library of mutant thioesterases by recovering microorganisms capable of faster growth in the medium. The incubating preferably comprises incubating the microorganism under conditions (i.e., temperature, etc.) suitable for growth when lipoic acid and/or octanoic acid is supplied exogenously. The microorganism is preferably $E.\ coli$.

Throughout the specification, a reference may be made using an abbreviation of a gene name or a polypeptide name, but it is understood that such an abbreviated gene or polypeptide name represents the genus of genes or polypeptides, respectively. Such gene names include all genes encoding the same polypeptide and homologous polypeptides having the same physiological function. Polypeptide names include all polypeptides that have the same activity (e.g., that catalyze the same fundamental chemical reaction).

Unless otherwise indicated, the accession numbers referenced herein are derived from the NCBI database (National Center for Biotechnology Information) maintained by the National Institute of Health, U.S.A.

EC numbers are established by the Nomenclature Committee of the International Union of Biochemistry and Molecular Biology (NC-IUBMB) (available at www-.chem.qmul/ac/uk/iubmb/enzyme/). The EC numbers referenced herein are derived from the KEGG Ligand database, maintained by the Kyoto Encyclopedia of Genes and Genomics, sponsored in part by the University of Tokyo.

As used herein, the term "alcohol dehydrogenase" (EC 1.1.1.*) is a polypeptide capable of catalyzing the conversion of a fatty aldehydes to an alcohol (e.g., a fatty alcohol). Additionally, one of ordinary skill in the art will appreciate that some alcohol dehydrogenases will catalyze other reactions as well. For example, some alcohol dehydrogenases will accept other substrates in addition to fatty aldehydes. Such non-specific alcohol dehydrogenases are, therefore, also included in this definition. Polynucleotide sequences encoding alcohol dehydrogenases are known in the art, and such dehydrogenases are publicly available.

The term "altered property" refers to a modification in one or more properties of a mutant polynucleotide or mutant protein with reference to a precursor polynucleotide or precursor protein. In one embodiment, the altered property is a changed preference for particular substrates, as reflected in, for example, a changed preference for particular acyl-CoA or acyl-acyl carrier protein substrates such as C8 acyl-CoA or acyl-acyl carrier protein substrates The term "alignment" refers to a method of comparing two or more polynucleotides or polypeptide sequences for the purpose of determining their relationship to each other. Alignments are typically performed by computer programs that apply various algorithms, however it is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW, (see, Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994); CLUSTALV, (see, Larkin M. A., et al., CLUSTALW2, ClustalW and ClustalX version 2, Bioinformatics 23(21): 2947-2948, 2007); Jotun-Hein, Muscle et al., MUSCLE: a multiple sequence alignment method with reduced time and space complexity, BMC Bioinformatics 5: 113, 2004); Mafft, Kalign, ProbCons, and T-Coffee (see Notredame et al., T-Coffee: A novel method for multiple sequence alignments, Journal of Molecular Biology 302: 205-217, 2000). Exemplary programs that implement one or more of the above algorithms include, but are not limited to MegAlign from DNAStar (DNAStar, Inc. 3801 Regent St. Madison, Wis. 53705), MUSCLE, T-Coffee, CLUSTALX, CLUSTALV, JalView, Phylip, and Discovery Studio from Accelrys (Accelrys, Inc., 10188 Telesis Ct, Suite 100, San Diego, Calif. 92121). In a non-limiting example, MegAlign is used to implement the CLUSTALW alignment algorithm with the following parameters: Gap Penalty 10, Gap Length Penalty 0.20, Delay Divergent Seqs (30%) DNA Transition Weight 0.50, Protein Weight matrix Gonnet Series, DNA Weight Matrix IUB.

The term "carbon chain length" is defined herein as the number of carbon atoms in a carbon chain of a thioesterase substrate or a fatty acid derivative. The carbon chain length of a particular molecule is marked as CX, wherein the "X" refers to the number of carbons in the carbon chain. "Long-chain" (e.g., long-chain fatty acid, fatty acyl-ACP, or fatty acyl-CoA) refers to molecules having a carbon chain longer than 12 carbons. "Medium-chain" (e.g., medium-chain fatty acid, fatty acyl-ACP, or fatty acyl-CoA) refers to molecules having a carbon chain of 6 to 12 carbons. "Short-chain" (e.g., short chain fatty acid, fatty acyl-ACP, or fatty acyl-CoA) refers to molecules having a carbon chain fewer than 6 carbons.

The term "carbon source" means a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, gases (e.g., CO and $CO_2$), and the like. These include, for example, various monosaccharides such as glucose, fructose, mannose and galactose; oligosaccharides such as fructo-oligosaccharide and galacto-oligosaccharide; polysaccharides such as xylose, and arabinose; disaccharides such as sucrose, maltose and turanose; cellulosic material such as methyl cellulose and sodium carboxymethyl cellulose; saturated or unsaturated fatty acid esters such as succinate, lactate and acetate; alcohols such as ethanol, etc., or mixtures thereof. The carbon source can additionally be a product of photosynthesis, including, but not limited to glucose. Glycerol can be an effective carbon source as well. Suitable carbon sources can be generated from any number of natural and renewable sources, including particularly biomass from agricultural, municipal and industrial waste, so long as the material can be used as a component of a cultivation to provide a carbon source. Biomass sources include corn stover, sugarcane, switchgrass, animal matter, or waste materials.

The term "chromosomal integration" means the process whereby an incoming sequence is introduced into the chromosome of a host cell. The homologous regions of the transforming DNA align with homologous regions of the chromosome. Then, the sequence between the homology boxes can be replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the microbial chromosome. Subsequently, the indigenous chromosomal region is deleted by the DNA construct in a double crossover.

The term "conditions that permit product production" refers to any cultivation conditions that allow a production host to produce a desired product, such as acyl-CoA or fatty acid derivatives including, for example, fatty acids, hydrocarbons, fatty alcohols, waxes, polyhydroxyalkanoates, or fatty esters. Cultivation conditions usually comprise many parameters. Exemplary conditions include, but are not limited to, temperature ranges, levels of aeration, pH ranges, and media composition (e.g., solvents and solutes). Each of these conditions, individually and in combination, allows the production host to grow. Exemplary media include broths or gels. Generally, a suitable medium includes a carbon source, such as glucose, fructose, cellulose, or the like, which can be metabolized by the microorganism directly. In addition, enzymes can be used in the medium to facilitate the mobilization (e.g., the depolymerization of starch or cellulose to fermentable sugars) and subsequent metabolism of the carbon source. To determine if the culture conditions are suitable for product production, the production host can be cultured for about 4, 8, 12, 24, 36, 48, or 72 hours. During culturing or after culturing, samples can be obtained and analyzed to determine if the culture conditions permit product production. For example, the production hosts in the sample or the medium in which the production hosts were grown can be tested for the presence of the desired product. When testing for the presence of a product, assays, such as, but not limited to, TLC, HPLC, GC/FID, GC/MS, LC/MS, MS, as well as those provided in the examples herein, can be used.

The term "consensus sequence" or "canonical sequence" refers to an archetypical amino acid sequence against which all variants of a particular protein or sequence of interest are compared. Either term also refers to a sequence that sets forth the nucleotides that are most often present in a polynucleotide sequence of interest. For each position of a protein, the consensus sequence gives the amino acid that is most abundant in that position in the sequence alignment.

The term "conservative substitutions" or "conserved substitutions" refers to, for example, a substitution of an amino acid with a conservative variant.

"Conservative variant" refers to residues that are functionally similar to a given residue. Amino acids within the following groups are conservative variants of one another: glycine, alanine, serine, and proline (very small); alanine, isoleucine, leucine, methionine, phenylalanine, valine, proline, and glycine (hydrophobic); alanine, valine, leucine, isoleucine, methionine (aliphatic-like); cysteine, serine, threonine, asparagine, tyrosine, and glutamine (polar); phenylalanine, tryptophan, tyrosine (aromatic); lysine, arginine, and histidine (basic); aspartate and glutamate (acidic); alanine and glycine; asparagine and glutamine; arginine and lysine; isoleucine, leucine, methionine, and valine; and serine and threonine.

The terms "corresponds to" or "corresponding to" refer to an amino acid residue or position in a first protein sequence being positionally equivalent to an amino acid residue or position in a second reference protein sequence by virtue of the fact that the residue or position in the first protein sequence aligns to the residue or position in the reference sequence using bioinformatic techniques, for example, using the methods described herein for preparing a sequence alignment. The corresponding residue in the first protein sequence is then assigned the position number in the second reference protein sequence.

The term "deletion," when used in the context of an amino acid sequence, means a deletion in or a removal of one or more residues from the amino acid sequence of a precursor protein, resulting in a mutant protein having at least one less amino acid residue as compared to the precursor protein. The term can also be used in the context of a nucleotide sequence, which means a deletion in or removal of a nucleotide from the polynucleotide sequence of a precursor polynucleotide.

The term "DNA construct" and "transforming DNA" (wherein "transforming" is used as an adjective) are used interchangeably herein to refer to a DNA used to introduce sequences into a host cell or organism. Typically a DNA construct is generated in vitro by PCR or other suitable technique(s) known to those in the art. In certain embodiments, the DNA construct comprises a sequence of interest (e.g., an incoming sequence). In some embodiments, the sequence is operably linked to additional elements such as control elements (e.g., promoters, etc.). A DNA construct can further comprise a selectable marker. It can also comprise an incoming sequence flanked by homology targeting sequences. In a further embodiment, the DNA construct comprises other non-homologous sequences, added to the ends (e.g., stuffer sequences or flanks). In some embodiments, the ends of the incoming sequence are closed such that the DNA construct forms a closed circle. The transforming sequences may be wildtype, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell; 2) mutagenize a region of the host cell chromosome (i.e., replace an endogenous sequence with a heterologous sequence); 3) delete target genes; and/or (4) introduce a replicating plasmid into the host. A polynucleotide is said to "encode" an RNA or a polypeptide if, in its native state or when manipulated by methods known to those of skill in the art, it can be transcribed and/or translated to produce the RNA, the polypeptide, or a fragment thereof. The antisense strand of such a polynucleotide is also said to encode the RNA or polypeptide sequences. As is known in the art, a DNA can be transcribed by an RNA polymerase to produce an RNA, and an RNA can be reverse transcribed by reverse transcriptase to produce a DNA. Thus a DNA can encode an RNA, and vice versa.

An "ester synthase" is a peptide capable of catalyzing a biochemical reaction to producing esters. For example, an ester synthase is a peptide that is capable of participating in converting a thioester to a fatty ester. In certain embodiments, an ester synthase converts a thioester, acyl-CoA, to a fatty ester. In an alternate embodiment, an ester synthase uses a thioester and an alcohol as substrates to produce a fatty ester. Ester synthases are capable of using short and long chain acyl-CoAs as substrates. In addition, ester synthases are capable of using short and long chain alcohols as substrates. Non-limiting examples of ester synthases include wax synthases, wax-ester synthases, acyl-CoA: alcohol transacylases, acyltransferases, fatty acyl-coenzyme A:fatty alcohol acyltransferases, fatty acyl-ACP transacylases, fatty-acid O-methyltransferases (EC 2.1.1.15), alcohol O-acyltransferases such as ATF (Rodriguez G M, Tashiro Y, Atsumi S. Expanding ester biosynthesis in *Escherichia coli*. Nat Chem Biol. 2014 April; 10(4):259-65), and alcohol acetyltransferases. An ester synthase that converts an acyl-CoA thioester to a wax is called a wax synthase. Exemplary ester synthases include those classified under the enzyme classification number EC 2.3.1.75. The term "ester synthase" does not comprise enzymes that also have thioesterase activity. The ones that have both ester synthase activity and thioesterase activity are categorized as thioesterases herein.

The term "expressed genes" refers to genes that are transcribed into messenger RNA (mRNA) and then translated into protein, as well as genes that are transcribed into types of RNA, such as transfer RNA (tRNA), ribosomal RNA (rRNA), and regulatory RNA, which are not translated into protein.

The terms "expression cassette" or "expression vector" refer to a polynucleotide construct generated recombinantly or synthetically, with a series of specified elements that permit transcription of a particular polynucleotide in a target cell. A recombinant expression cassette can be incorporated into a plasmid, chromosome, mitochondrial DNA, plasmid DNA, virus, or polynucleotide fragment. Typically, the recombinant expression cassette portion of an expression vector includes, among other sequences, a polynucleotide sequence to be transcribed and a promoter. In particular embodiments, expression vectors have the ability to incorporate and express heterologous polynucleotide fragments in a host cell. Many prokaryotic and eukaryotic expression vectors are commercially available. Selection of appropriate expression vectors is within the knowledge of those of skill in the art. The term "expression cassette" is also used interchangeably herein with "DNA construct," and their grammatical equivalents.

The term "fatty acid derivative," as used herein, refers to a composition that is derived from a metabolic pathway, which pathway includes a thioesterase reaction. Thus, fatty acid derivative products can be products that are, or are derived from, fatty acid fatty thioester, or fatty esters that are directly or indirectly products of a thioesterase reaction. Fatty acid derivatives thus include, for example, products that are, or that are derived from, fatty acids that are the direct or indirect reaction product of a thioesterase, and/or a fatty ester that is a direct or indirect reaction product of a thioesterase. Exemplary fatty acid derivatives include, for example, short and long chain alcohols, hydrocarbons, and fatty alcohols and esters, including waxes, fatty acid esters, and/or fatty esters. Specific non-limiting examples of fatty acid derivatives include fatty acids, fatty acid methyl esters, fatty acid ethyl esters, fatty alcohols, fatty alkyl-acetates, fatty aldehydes, fatty amines, fatty amides, fatty sulfates, fatty ethers, ketones, alkanes, internal olefins, terminal olefins, dicarboxylic acids, polyhydroxyalkanoates, diols and terminal and/or internal fatty acids.

The term "fatty acid derivative enzymes" refers to, collectively and individually, enzymes that may be expressed or overexpressed in the production of fatty acid derivatives. These enzymes may be parts of a fatty acid biosynthetic pathway. Non-limiting examples of fatty acid derivative synthases include fatty acid synthases, thioesterases, acyl-CoA synthases, acyl-CoA reductases, wax/ester synthases, alcohol dehydrogenases, alcohol acyltransferases, fatty alcohol acetyl transferases, fatty alcohol-forming acyl-CoA reductase, fatty-alcohol-forming acyl-CoA reductases, fatty acid decarbonylases, alcohol O-acyltransferases, carboxylic acid reductases, fatty alcohol acetyl transferases, aldehyde deformylating oxygenases, aldehyde reductases, decarboxylases, acyl condensing enzymes, aminotransferases, decarbonylases, fatty-acid O-methyltransferases, carboxylic acid reductases, decarboxylases, and ester synthases.

Fatty acid derivative enzymes convert substrates into fatty acid derivatives. In certain circumstances, a suitable substrate may be a first fatty acid derivative, which is converted by a fatty acid derivative enzyme into a different, second fatty acid derivative.

The term "fatty alcohol" refers to an alcohol having the formula ROH. In certain embodiments, a fatty alcohol is an alcohol made from a fatty acid or fatty acid derivative. In one embodiment, the R group is at least about 5, 6, 7, 8, 9, 10, 11, 12, 13, 14, 15, 16, 17, 18, 19, or 20 carbons in length. R can be straight or branched chain. The branched chains may have one or more points of branching. In addition, the branched chains may include cyclic branches, such as cyclopropane or epoxide moieties. Furthermore, R can be saturated or unsaturated. If unsaturated, R can have one or more points of unsaturation. In one embodiment, the fatty alcohol is produced biosynthetically. Fatty alcohols have many uses. For example, fatty alcohols can be used to produce specialty chemicals. Specifically, fatty alcohols can be used as biofuels; as solvents for fats, waxes, gums, and resins; in pharmaceutical salves, emollients and lotions; as lubricating-oil additives; in detergents and emulsifiers; as textile antistatic and finishing agents; as plasticizers; as nonionic surfactants; and in cosmetics, for example as thickeners.

The term "fatty alcohol forming peptides" refers to peptides capable of catalyzing the conversion of acyl-CoA to fatty alcohol, including fatty alcohol forming acyl-CoA reductase (FAR, EC 1.1.1.*), acyl-CoA reductase (EC 1.2.1.50), long-chain acyl-(acyl-carrier-protein) reductase (EC1.2.1.80), or alcohol dehydrogenase (EC 1.1.1.1). Additionally, one of ordinary skill in the art will appreciate that some fatty alcohol forming peptides will catalyze other reactions as well. For example, some acyl-CoA reductase peptides will accept substrates other than acyl-CoA such as acyl-ACP. Such non-specific peptides are, therefore, also included. Polynucleotide sequences encoding fatty alcohol forming peptides are known in the art and such peptides are publicly available.

The term "fatty aldehyde" refers to an aldehyde having the formula RCHO characterized by an unsaturated carbonyl group (C=O). In certain embodiments, a fatty aldehyde is an aldehyde made from a fatty acid or fatty acid derivative. In one embodiment, the R group is at least about 1, 2, 3, 4, 5, 6, 7, 8, 9, 10, 11, 12, 13, 14, 15, 16, 17, 18, 19, or 20 carbons in length. R can be straight or branched chain. The branched chains may have one or more points of branching. In addition, the branched chains can be cyclic branches. Furthermore, R can be saturated or unsaturated. If unsaturated, R can have one or more points of unsaturation. In one embodiment, the fatty aldehyde is produced biosynthetically. Fatty aldehydes have many uses. For example, fatty aldehydes can be used to produce specialty chemicals. Specifically, fatty aldehydes can be used to produce polymers, resins, dyes, flavorings, plasticizers, perfumes, pharmaceuticals, and other chemicals. Some are used as solvents, preservatives, or disinfectants. Some natural and synthetic compounds, such as vitamins and hormones, are also aldehydes.

The terms "fatty aldehyde biosynthetic polypeptide," "carboxylic acid reductase," and "CAR" are used interchangeably herein.

The term "fatty ester" refers to an ester having greater than 5 carbon atoms. In certain embodiments, a fatty ester is an ester made from a fatty acid, for example a fatty acid ester. In one embodiment, a fatty ester contains an A side (i.e., the carbon chain attached to the carboxylate oxygen) and a B side (i.e., the carbon chain comprising the parent carboxylate). In a particular embodiment, when a fatty ester is derived from the fatty acid biosynthetic pathway, the A side is contributed by an alcohol, and the B side is contributed by a fatty acid. Any alcohol can be used to form the A side of the fatty esters. For example, the alcohol can be derived from the fatty acid biosynthetic pathway. Alternatively, the alcohol can be produced through non-fatty acid biosynthetic pathways. Moreover, the alcohol can be provided exogenously. For example, the alcohol can be supplied to the cultivation broth in instances where the fatty ester is produced by an organism. Alternatively, a carboxylic acid, such as a fatty acid or acetic acid, can be supplied exogenously in instances where the fatty ester is produced by an organism that can also produce alcohol. The carbon chains comprising the A side or B side can be of any length. In one embodiment, the A side of the ester is at least about 1, 2, 3, 4, 5, 6, 7, 8, 10, 12, 14, 16, 18, or 20 carbons in length. The B side of the ester is at least about 4, 6, 8, 10, 12, 14, 16, 18, 20, 22, 24, or 26 carbons in length. The A side and/or the B side can be straight or branched chain. The branched chains may have one or more points of branching. In addition, the branched chains may include cyclic branches, such as cyclopropane or epoxide moieties. Furthermore, the A side and/or B side can be saturated or unsaturated. If unsaturated, the A side and/or B side can have one or more points of unsaturation. In one embodiment, the fatty ester is produced biosynthetically. In this embodiment, first the fatty acid is "activated." Non-limiting examples of activated fatty acids are acyl-CoA, acyl ACP, acyl-AMP, and acyl phosphate. Acyl-CoA can be a direct product of fatty acid biosynthesis or degradation. In addition, acyl-CoA can be synthesized from a free fatty acid, a CoA, and an adenosine nucleotide triphosphate (ATP). An example of an enzyme that produces acyl-CoA is an acyl-CoA synthase. After the fatty acid is activated, it can be readily transferred to a recipient nucleophile. Exemplary nucleophiles are alcohols, thiols, amines, or phosphates. In another embodiment, the fatty ester can be derived from a fatty acyl-thioester and an alcohol. In one embodiment, the fatty ester is a wax. The wax can be derived from a long chain fatty alcohol and a long chain fatty acid. In another embodiment, the fatty ester is a fatty acid thioester, for example fatty acyl coenzyme A (acyl-CoA). In other embodiments, the fatty ester is a fatty acyl pantothenate, an acyl acyl carrier protein (acyl-ACP), a fatty acyl enzyme ester, or a fatty phosphate ester. An ester can be formed from an acyl enzyme ester intermediate through the alcoholysis of the ester bond to form a new ester and the free enzyme. Fatty esters have many uses. For example, fatty esters can be used as, or as a component of, a biofuel or a surfactant.

"Gene" refers to a polynucleotide (e.g., a DNA segment), which encodes a polypeptide, and may include regions preceding and following the coding regions as well as intervening sequences (introns) between individual coding segments (exons).

The term "homologous genes" refers to a pair of genes from different but related species, which correspond to each other and which are identical or similar to each other. The term encompasses genes that are separated by the speciation process during the development of new species) (e.g., orthologous genes), as well as genes that have been separated by genetic duplication (e.g., paralogous genes).

The term "endogenous protein" refers to a protein that is native to or naturally occurring in a cell. "Endogenous polynucleotide" refers to a polynucleotide that is in the cell and was not introduced into the cell using recombinant engineering techniques. For example, a gene that was present in the cell when the cell was originally isolated from nature. A gene is still considered endogenous if the control sequences, such as a promoter or enhancer sequences that activate transcription or translation, have been altered through recombinant techniques. Conversely, the term "heterologous" is also used herein, and refers to a protein or a polynucleotide that does not naturally occur in a host cell.

The term "homologous recombination" refers to the exchange of DNA fragments between two DNA molecules or paired chromosomes at sites of identical or nearly identical nucleotide sequences. In certain embodiments, chromosomal integration is homologous recombination.

The term "homologous sequences" as used herein refers to a polynucleotide or polypeptide sequence having, for example, about 100%, about 99% or more, about 98% or more, about 97% or more, about 96% or more, about 95% or more, about 94% or more, about 93% or more, about 92% or more, about 91% or more, about 90% or more, about 88% or more, about 85% or more, about 80% or more, about 75% or more, about 70% or more, about 65% or more, about 60% or more, about 55% or more, about 50% or more, about 45% or more, or about 40% or more sequence identity to another polynucleotide or polypeptide sequence when optimally aligned for comparison. In particular embodiments, homologous sequences can retain the same type and/or level of a particular activity of interest. In some embodiments, homologous sequences have between 85% and 100% sequence identity, whereas in other embodiments there is between 90% and 100% sequence identity. In particular embodiments, there is 95% and 100% sequence identity.

"Homology" refers to sequence similarity or sequence identity. Homology is determined using standard techniques known in the art (see, e.g., Smith and Waterman, Adv. Appl. Math., 2:482, 1981; Needleman and Wunsch, J. Mol. Biol., 48:443, 1970; Pearson and Lipman, Proc. Natl. Acad. Sci. USA 85:2444, 1988; programs such as GAP, BESTFIT, FASTA, and TFASTA in the Wisconsin Genetics Software Package (Genetics Computer Group, Madison, Wis.); and Devereux et al., Nucl. Acid Res., 12:387-395, 1984). A non-limiting example includes the use of the BLAST program (Altschul et al., Gapped BLAST and PSI-BLAST: a new generation of protein database search programs, Nucleic Acids Res. 25:3389-3402, 1997) to identify sequences that can be said to be "homologous." A recent version such as version 2.2.16, 2.2.17, 2.2.18, 2.2.19, or the latest version, including sub-programs such as blastp for protein-protein comparisons, blastn for nucleotide-nucleotide comparisons, tblastn for protein-nucleotide comparisons, or blastx for nucleotide-protein comparisons, and with parameters as follows: Maximum number of sequences returned 10,000 or 100,000; E-value (expectation value) of 1e-2 or 1e-5, word size 3, scoring matrix BLOSUM62, gap cost existence 11, gap cost extension 1, may be suitable. An E-value of 1e-5, for example, indicates that the chance of a homologous match occurring at random is about 1 in 10,000, thereby marking a high confidence of true homology.

The term "host strain" or "host cell" refers to a suitable host for an expression vector comprising a DNA of the present invention. The host may comprise any organism, without limitation, capable of containing and expressing the nucleic acids or genes disclosed herein. The host may be prokaryotic or eukaryotic, single-celled or multicellular, including mammalian cells, plant cells, fungi, etc. Examples of single-celled hosts include cells of *Escherichia, Salmonella, Bacillus, Clostridium, Streptomyces, Staphyloccus, Neisseria, Lactobacillus, Shigella,* and *Mycoplasma.* Suitable *E. coli* strains (among a great many others) include BL21(DE3), C600, DH5αF', HB101, JM83, JM101, JM103, JM105, JM107, JM109, JM110, MC1061, MC4100, MM294, NM522, NM554, TGI, $\chi$1776, XL1-Blue, and Y1089+, all of which are commercially available.

The term "hydrocarbon" refers to chemical compounds that contain the elements carbon (C) and hydrogen (H). All hydrocarbons consist of a carbon backbone and atoms of hydrogen attached to that backbone. Sometimes, the term is used as a shortened form of the term "aliphatic hydrocarbon." There are essentially three types of hydrocarbons: (1) aromatic hydrocarbons, which have at least about one aromatic ring; (2) saturated hydrocarbons, also known as alkanes, which lack double, triple or aromatic bonds; and (3) unsaturated hydrocarbons, which have one or more double or triple bonds between carbon atoms and include, for example, alkenes (e.g., dienes), and alkynes.

The term "identical" (or "identity"), in the context of two polynucleotide or polypeptide sequences, means that the residues in the two sequences are the same when aligned for maximum correspondence, as measured using a sequence comparison or analysis algorithm such as those described herein. For example, if when properly aligned, the corresponding segments of two sequences have identical residues at 5 positions out of 10, it is said that the two sequences have a 50% identity. Most bioinformatic programs report percent identity over aligned sequence regions, which are typically not the entire molecules. If an alignment is long enough and contains enough identical residues, an expectation value can be calculated, which indicates that the level of identity in the alignment is unlikely to occur by random chance.

The term "insertion," when used in the context of a polypeptide sequence, refers to an insertion in the amino acid sequence of a precursor polypeptide, resulting in a mutant polypeptide having an amino acid that is inserted between two existing contiguous amino acids, i.e., adjacent amino acids residues, which are present in the precursor polypeptide. The term "insertion," when used in the context of a polynucleotide sequence, refers to an insertion of one or more nucleotides in the precursor polynucleotide between two existing contiguous nucleotides, i.e., adjacent nucleotides, which are present in the precursor polynucleotides.

The term "introduced" refers to, in the context of introducing a polynucleotide sequence into a cell, any method suitable for transferring the polynucleotide sequence into the cell. Such methods for introduction include but are not limited to protoplast fusion, transfection, transformation, conjugation, and transduction (see, e.g., Ferrari et al., Genetics, in Hardwood et al, (eds.), *Bacillus,* Plenum Publishing Corp., pp. 57-72, 1989).

The term "isolated" or "purified" means a material that is removed from its original environment, for example, the natural environment if it is naturally occurring, or a cultivation broth if it is produced in a recombinant host cell cultivation medium. A material is said to be "purified" when it is present in a particular composition in a higher concentration than the concentration that exists prior to the purification step(s). For example, with respect to a composition normally found in a naturally-occurring or wild type organism, such a composition is "purified" when the final composition does not include some material from the original matrix. As another example, where a composition is found in combination with other components in a recombinant host cell cultivation medium, that composition is purified when the cultivation medium is treated in a way to remove some component of the cultivation, for example, cell debris or other cultivation products, through, for example, centrifugation or distillation. As another example, a naturally-occurring polynucleotide or polypeptide present in a living animal is not isolated, but the same polynucleotide or polypeptide, separated from some or all of the coexisting materials in the natural system, is isolated, whether such process is through genetic engineering or mechanical separation. Such polynucleotides can be parts of vectors. Alternatively, such polynucleotides or polypeptides can be parts of compositions. Such polynucleotides or polypeptides can be considered "isolated" because the vectors or compositions comprising thereof are not part of their natural environments. In another example, a polynucleotide or protein is said to be purified if it gives rise to essentially one band in an electrophoretic gel or a blot.

The term "mutant thioesterase" or "variant thioesterase" refers to a thioesterase that comprises a mutation with reference to a precursor thioesterase.

The term "mutation" refers to, in the context of a polynucleotide, a modification to the polynucleotide sequence resulting in a change in the sequence of a polynucleotide with reference to a precursor polynucleotide sequence. A mutant polynucleotide sequence can refer to an alteration that does not change the encoded amino acid sequence, for example, with regard to codon optimization for expression purposes, or that modifies a codon in such a way as to result in a modification of the encoded amino acid sequence. Mutations can be introduced into a polynucleotide through any number of methods known to those of ordinary skill in the art, including random mutagenesis, site-specific mutagenesis, oligonucleotide directed mutagenesis, gene shuffling, directed evolution techniques, combinatorial mutagenesis, site saturation mutagenesis among others.

"Mutation" or "mutated" means, in the context of a protein, a modification to the amino acid sequence resulting in a change in the sequence of a protein with reference to a precursor protein sequence. A mutation can refer to a substitution of one amino acid with another amino acid, an insertion or a deletion of one or more amino acid residues. Specifically, a mutation can also be the replacement of an amino acid with a non-natural amino acid, or with a chemically-modified amino acid or like residues. A mutation can also be a truncation (e.g., a deletion or interruption) in a sequence or a subsequence from the precursor sequence. A mutation may also be an addition of a subsequence (e.g., two or more amino acids in a stretch, which are inserted between two contiguous amino acids in a precursor protein sequence) within a protein, or at either terminal end of a protein, thereby increasing the length of (or elongating) the protein. A mutation can be made by modifying the DNA sequence corresponding to the precursor protein. Mutations can be introduced into a protein sequence by known methods in the art, for example, by creating synthetic DNA sequences that encode the mutation with reference to precursor proteins, or chemically altering the protein itself. A "mutant" as used herein is a protein comprising a mutation. For example, it is also possible to make a mutant by replacing a portion of a thioesterase with a wild type sequence that corresponds to such portion but includes a desired variation at a specific position that is naturally-occurring in the wild type sequence.

A "naturally-occurring equivalent," in the context of the present invention, refers to a naturally-occurring thioesterase, or a portion thereof that comprises a naturally-occurring residue.

The term "operably linked," in the context of a polynucleotide sequence, refers to the placement of one polynucleotide sequence into a functional relationship with another polynucleotide sequence. For example, a DNA encoding a secretory leader (e.g., a signal peptide) is operably linked to a DNA encoding a polypeptide if it is expressed as a preprotein that participates in the secretion of the polypeptide. A promoter or an enhancer is operably linked to a coding sequence if it affects the transcription of the sequence. A ribosome binding site is operably linked to a coding sequence if it is positioned so as to facilitate translation. Generally, "operably linked" means that the DNA sequences being linked are contiguous, and, in the case of a secretory leader, contiguous and in the same reading frame.

The term "optimal alignment" refers to the alignment giving the highest overall alignment score.

"Overexpressed" or "overexpression" in a host cell occurs if the enzyme is expressed in the cell at a higher level than the level at which it is expressed in a corresponding wild-type cell.

The terms "percent sequence identity," "percent amino acid sequence identity," "percent gene sequence identity," and/or "percent polynucleotide sequence identity," with respect to two polypeptides, polynucleotides and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical. The percent identities expressed herein with respect to a given named reference sequence are determined over the entire reference sequence, rather than only a portion thereof. Thus, an amino acid sequence at least about 80% identical to positions 28-317 of SEQ ID NO:4, for example, is at least about 80% identical to the entire sequence of positions 28-317 of SEQ ID NO:4, as opposed merely to subsequences thereof.

The term "plasmid" refers to a circular double-stranded (ds) DNA construct used as a cloning vector, and which forms an extrachromosomal self-replicating genetic element in some eukaryotes or prokaryotes, or integrates into the host chromosome.

The term "precursor thioesterase" refers a thioesterase protein from which the mutant thioesterase of the invention can be derived, through, for example, recombinant or chemical means. Examples of precursor thioesterases are naturally-occurring or wildtype thioesterases from plant, animal or microbial sources. A precursor thioesterase can also be a thioesterase that is non-naturally-occurring. An example of a non-naturally-occurring thioesterase is a thioesterase made through, for example, random mutation, chemical synthesis, molecular evolution, or site directed mutagenesis, which can serve as a useful starting point from which to design and/or make the mutant thioesterases of the invention.

A "production host" is a cell used to produce products. As disclosed herein, a production host is modified to express or overexpress selected genes, or to have attenuated expression of selected genes. Non-limiting examples of production hosts include plant, animal, human, bacteria, yeast, cyanobacteria, algae, and/or filamentous fungi cells.

A "promoter" is a polynucleotide sequence that functions to direct transcription of a downstream gene. In preferred embodiments, the promoter is appropriate to the host cell in which the target gene is being expressed. The promoter, together with other transcriptional and translational regulatory polynucleotide sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

The terms "protein" and "polypeptide" are used interchangeably herein. The 3-letter code as well as the 1-letter code for amino acid residues as defined in conformity with the IUPAC-IUB Joint Commission on Biochemical Nomenclature (JCBN) is used throughout this disclosure. It is also understood that a polypeptide may be coded for by more than one polynucleotide sequence due to the degeneracy of the genetic code. An enzyme is a protein.

The term "recombinant," when used to modify the term "cell" or "vector" herein, refers to a cell or a vector that has been modified by the introduction of a heterologous polynucleotide sequence, or that the cell is derived from a cell so modified. Thus, for example, recombinant cells express genes that are not found in identical form within the native (non-recombinant) form of the cells or express, as a result of deliberate human intervention, native genes that are otherwise abnormally expressed, underexpressed or not expressed at all. The terms "recombination," "recombining," and generating a "recombined" polynucleotide refer generally to the assembly of two or more polynucleotide fragments wherein the assembly gives rise to a chimeric polynucleotide made from the assembled parts.

The terms "regulatory segment," "regulatory sequence," or "expression control sequence" refer to a polynucleotide sequence that is operatively linked with another polynucleotide sequence that encodes the amino acid sequence of a polypeptide chain to effect the expression of that encoded amino acid sequence. The regulatory sequence can inhibit, repress, promote, or even drive the expression of the operably-linked polynucleotide sequence encoding the amino acid sequence.

The term "selectable marker" or "selective marker" refers to a polynucleotide (e.g., a gene) capable of expression in a host cell, which allows for ease of selection of those hosts containing the vector. Examples of selectable markers include but are not limited to antimicrobial markers. Thus, the term "selectable marker" refers to a gene that provides an indication when a host cell has taken up an incoming sequence of interest or when some other reaction has taken place. Typically, selectable markers are genes that confer antimicrobial resistance or a metabolic advantage on the host cells to allow the cells containing the exogenous sequences to be distinguished from the cells that have not received the exogenous sequences. A "residing selectable marker" is one that is located on the chromosome of the microorganism to be transformed. A residing selectable marker encodes a gene that is different from the selectable marker on the transforming construct. Selective markers are known to those of skill in the art. As indicated above, suitably the marker is an antimicrobial resistant marker, including, for example, $amp^R$; $phleo^R$; $spec^R$; $kan^R$; $ery^R$; $tet^R$; $cmp^R$; and $neo^R$. See, e.g., Guerot-Fleury, Gene, 167: 335-337, 1995; Palmeros et al., Gene, 247:255-264, 2000; and Trieu-Cuot et al., Gene, 23:331-341, 1983. Other markers useful in accordance with the invention include, but are not limited to, auxotrophic markers, such as tryptophan; and detection markers, such as β-galactosidase.

The term "selectable marker-encoding nucleotide sequence" refers to a polynucleotide sequence that is capable of expression in the host cells and where the expression of the selectable marker confers to the cells containing the expressed gene the ability to grow in the presence of a corresponding selective agent or in the absence of one or more essential nutrients.

The term "substantially identical," in the context of two polynucleotides or two polypeptides refers to a polynucleotide or polypeptide that comprises at least 70% sequence identity, for example, at least 75%, at least 80%, at least 85%, at least 90%, at least 91%, at least 92%, at least 93%, at least 94%, at least 95%, at least 96%, at least 97%, at least 98%, or at least 99% sequence identity as compared to a reference sequence using the programs or algorithms (e.g., BLAST, ALIGN, CLUSTAL) using standard parameters.

"Substantially purified" means molecules that are at least about 60% free, preferably at least about 75% free, about 80% free, about 85% free, and more preferably at least about 90% free from other components with which they are naturally associated. As used herein, the term "purified" or "to purify" also refers to the removal of contaminants from a sample.

"Substitution" means replacing an amino acid in the sequence of a precursor protein with another amino acid at a particular position, resulting in a mutant of the precursor protein. The amino acid used as a substitute can be a naturally-occurring amino acid, or can be a synthetic or non-naturally-occurring amino acid.

The term "thioesterase" refers to an enzyme that has thioesterase activity. Thioesterases include thioester hydrolases, which are identified as members of Enzyme Classification E.C. 3.1.2.x and are obtainable from a variety of sources.

The term "thioesterase activity" refers to the capacity to catalyze a thioester cleavage reaction, which usually involves the hydrolysis of a thioester at a thiol group into an acid and a thiol, but can also include transesterification, wherein a thioester bond is cleaved and a new ester bond is formed. In general, an acyl-ACP thioesterase is capable of catalyzing the hydrolytic cleavage of fatty acyl-acyl carrier protein thioesters and/or fatty acyl-coenzyme A thioesters. Examples of enzymes having thioesterase activity include acetyl-CoA hydrolase, palmitoyl-CoA hydrolase, succinyl-CoA hydrolase, formyl-CoA hydrolase, acyl-CoA hydrolase, palmitoyl-protein thioesterase, and ubiquitin thioesterase. Thioesterase activity can be established by any of a number of assays described in U.S. Pat. No. 9,587,231, which is incorporated herein by reference.

The term "transformed" or "stably transformed" cell refers to a cell that has a non-native (heterologous) polynucleotide sequence integrated into its genome or as an episomal plasmid that is maintained for at least two generations.

"Vector" refers to a polynucleotide construct designed to introduce polynucleotides into one or more cell types. Vectors include cloning vectors, expression vectors, shuttle vectors, plasmids, cassettes and the like. In some embodiments, the polynucleotide construct comprises a polynucleotide sequence encoding a thioesterase (e.g., a precursor or a mature thioesterase) that is operably linked to a suitable prosequence (e.g., a secretory pro-sequence) capable of effecting the expression of the polynucleotide or gene in a suitable host.

"Wild-type" means, in the context of gene or protein, a polynucleotide or protein sequence that occurs in nature. In some embodiments, the wild-type sequence refers to a sequence of interest that is a starting point for protein engineering.

The mutant thioesterases of the present invention herein can be used in place of the mutant thioesterases described in U.S. Pat. No. 9,587,231 for any embodiments described in U.S. Pat. No. 9,587,231.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Summary

Medium-chain fatty acids (MCFA) are currently obtained from plants oils such as coconut and palm kernel oil or poorly selective chemical synthesis from fossil fuels. Consequently, strong demand for these molecules has contributed to the growth of oil-seed plantations and the deforestation of tropical habitats. Microbial conversion of renewable feedstocks to MCFA is one potential alternative to current practices. However, one of the challenges of microbial production of MCFA is the lack of enzymes that are both highly active and selective towards medium chain-length substrates. As a result, most microbial biocatalysts are either able to produce high titers of MCFA with mixed chain-lengths or low titers of products with a narrow chain-length distribution. One of the few enzymes involved in oleochemical metabolism possessing strong selectivity is the acyl-ACP thioesterase. This enzyme catalyzes the last step in microbial MCFA production strategies by hydrolyzing the thioester bond linking an acyl-chain to the acyl-carrier protein (ACP). In search of highly active and selective enzymes capable of producing octanoic acid, we developed a selection platform that relies on the lipoic acid requirement of E. coli. This selection was used to find improved mutants in a library of randomly mutagenized gene variants derived from the C8 specific Cuphea palustris FatB1 thioesterase. Using this selection, we isolated a thioesterase that produced 1.7 g/L of octanoic acid with >90% specificity. In addition, we were able to show that a single chromosomal copy of this thioesterase was sufficient to achieve the titers mentioned above, a feat that is crucial when building industrially relevant strains. In vitro studies confirmed the mutant thioesterase possessed a large increase in kcat compared to its native counterpart.

Introduction

Figure 1:
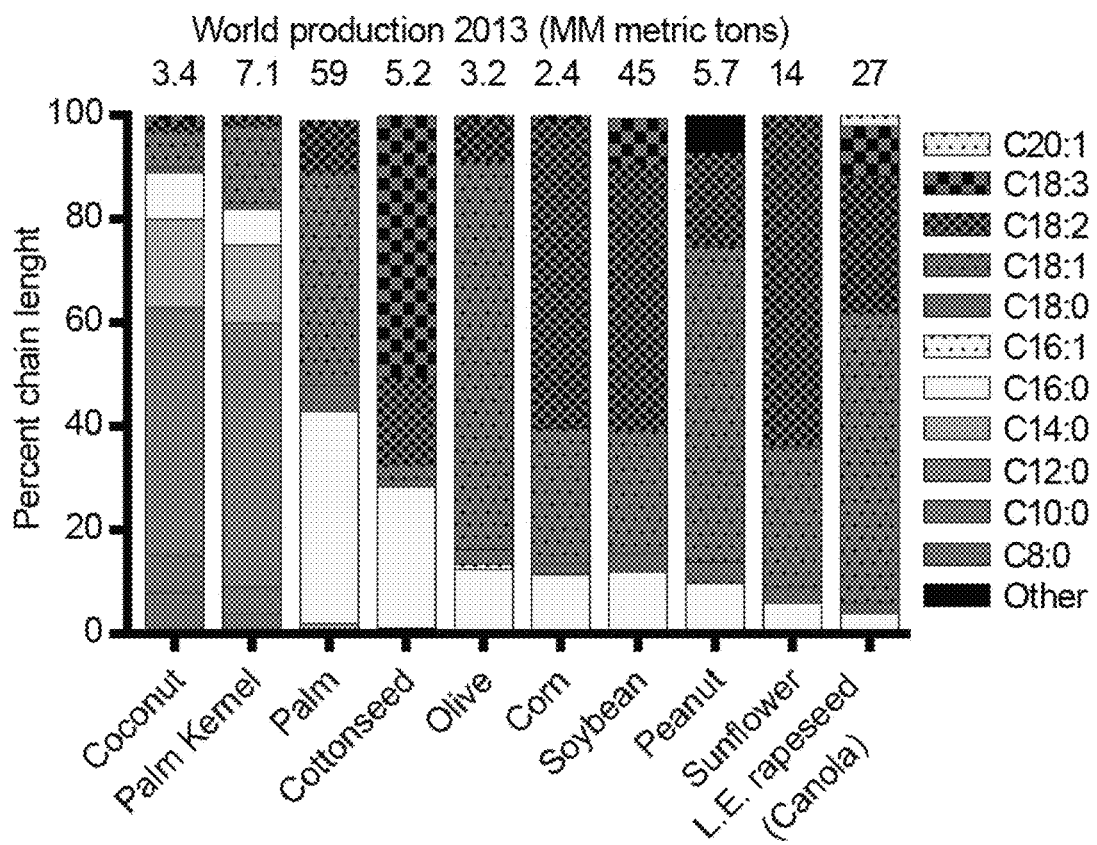
FIG. 1. Plant oils and fats as a percentage of their chain-length composition. Coconut plant oil and palm kernel oil are main sources of medium-chain fatty acids (MCFA) (C8-C12).

Oleochemicals are a large class of industrial chemicals used for making products in the bioenergy, plastics, surfactants, and personal care sectors. Oleochemicals include molecules such as free fatty acids (FFA), fatty acid methyl esters (FAME), fatty alcohols, and organosulfates (e.g. sodium dodecyl sulfate)[1,2]. While the most desirable oleochemicals contain medium chains ($C_6$-$C_{12}$), most natural oleochemical sources are dominated by long acyl chains (>$C_{16}$). Of the major oil seed crops, only coconut and palm have large fractions of medium chain fatty acids (MCFA), with $C_{12}$ being the most abundant chain length (FIG. 1). Some plant oils contain high proportions of medium-chain acids, e.g. Umbellularia californica (California Bay laurel) contains high proportion of $C_{12}$ fatty acids[3] and Cuphea species often contain high percentages of $C_8$ fatty acids[4], but most are not cultivated in volumes capable of meeting oleochemical demand. The low availability of MCFA has motivated the development of microbial conversion strategies where renewable sugars are converted to specific oleochemicals in the medium chain category[5]. In this approach, metabolic engineering principles are used to redirect carbon flux through fatty acid biosynthesis to specific products[6,7] leveraging heterologous enzymes capable of catalyzing desired biochemical transformations.

While many oleochemicals have been produced in microbes, there remains a dearth of enzymes capable of directing flux to products containing a specific chain length. The notable exception is the thioesterase[8] which cleaves acyl-thioesters (CoA or acyl-carrier protein, ACP) to release FFA from biosynthetic pathways. Thioesterases are expressed in many organisms for various purposes. Microbial thioesterases often have proofreading roles in the cell and therefore act on a broad substrate range. In some cases, thioesterase selectivity can be tailored via protein engineering[9], but complete selectivity remains an unmet challenge. In contrast, many plant thioesterases act on a narrow set of substrates. Plants synthesize fatty acids in the chloroplast and lipids in the cytsol[12]. In order to transport acyl-chains across the chloroplast membrane, plants express thioesterases to release FFA in the chloroplast and reactivate them as acyl-CoA thioesters in the cytosol. Therefore, the substrate specificity of thioesterases often dictates the composition of plant oils. For this reason, plants have become a preferred source for isolating thioesterases with desired substrate preference. These enzymes can then be used in either transgenic crops or microbes to produce oleochemicals with desired chain lengths[7]. This approach is often made difficult in Escherichia coli by a loss of activity when plant thioesterases are heterologously expressed. Therefore, researchers remain motivated to isolate, evolve, and/or engineer improved thioesterases with desired selectivity and activity.

One challenge to thioesterase engineering is the lack of good screening methods to differentiate products with different chain lengths. The analysis of fatty acid chain length typically uses gas chromatography to separate fatty acid methyl esters (FAME) derived from biological samples. While accurate, this method requires considerable sample preparation time and instrument time that limits the number of samples that can be processed to less than a 200 per day per instrument. In protein engineering projects, a library size typically ranges from $10^3$ to $10^8$ samples. Therefore, gas chromatography is not an applicable method for screening large libraries for increased activity. Without high throughput screens, mutagenesis is limited to rational design. Although rational design of thioesterases has given some degree of sucess[9,17], there is still considerable room for improving these enzymes. One alternative to achieving this goal is the development of biosensors that use screening (change in observable phenotype) or selection (live/dead) as a way to differentiate improved enzymes from the rest. Biosensors for detecting fatty acids and other aliphatic molecules have been developed by others using transcriptional regulators linked to fluorescent proteins[18] and G-protein coupled receptors[19]. However, these approaches have limited ability to tailor chain-length specificity. Here, we developed a genetic selection for acyl-chains containing exactly eight carbons using the lipoic acid requirement of *E. coli* under aerobic conditions.

Lipoic acid is an essential vitamin in most of organisms. It is an important cofactor for function of several key enzymes involved in aerobic metabolism, such as pyruvate dehydrogenase, 2-oxoglutarate dehydrogenase, the glycine cleavage system, and the branched-chain 2-oxoacid dehydrogenase[20]. Pyruvate dehydrogenase contains a lipoyl group in its E2 domain that translocates an activated acetyl moiety to the thiol of coenzyme A to form acetyl-CoA. This lipoyl group synthesis proceeds via one of two pathways in *E. coli*. The endogenous biosynthesis pathway branches from a central intermediate in fatty acid biosynthesis octanoyl-ACP (FIG. 2) which donates its octanoyl group to the E2-domain of pyruvate dehydrogenase via the enzyme LipB (octanoyl-ACP N-lipoyltransferase). Next, LipA, an iron-sulfur cluster enzyme, catalyzes a radical reaction to install two sulfur atoms at $C_6$ and $C_8$ positions of the octanoyl group to complete this biosynthesis. *E. coli* ΔlipB mutants are unable to grow on minimal media. However, *E. coli* has a salvage pathway to obtain and assimilate free lipoic acid from the environment. LplA, a lipoate-protein ligase, is an ATP-dependent enzyme that activates lipoic acid as well as octanoic acid and transfers it to the E2-domain of pyruvate dehydrogenase. As seen in FIG. 2, growth of *E. coli* ΔlipB mutants can be rescued by supplying lipoic acid as well as octanoic acid in the media[21]. The authors proposed that LplA could transfer octanoic acid to the E2 domain of pyruvate dehydrogenase and rejoin the native lipoic acid biosynthesis pathway where a LipA-catalyzed reaction completes the pathway. Conversely, other chain-length carboxylic acids were not able to rescue growth of the mutant (not shown). Based on these intriguing results, we hypothesized that an *E. coli* ΔlipB strain could be leveraged as a growth-based biosensor for octanoic acid presence.

In these examples, we describe how we used this novel screening approach to select for improved variants from a randomly mutagenized library of *Cuphea palustris* FatB1 thioesterase (CpFatB1) genes[22]. The best variants led to 5-7 fold improvements in octanoic acid titer while sustaining the enzyme's high selectivity towards 8-carbon chains. The best variant CpFatB1-M4 demonstrated a 15-fold increased $k_{cat}$.

The increased specific activity enabled us to place the gene on the chromosome in a single copy and achieve the same octanoic acid titer achieved by plasmid containing strains.

MATERIALS AND METHODS

Chemicals, Reagents, and Media

Chemicals were purchased from either Sigma Aldrich (St. Louis, Mo.) or Fisher Scientific (Waltham, Mass.). Oligonucleotides and gene fragments were purchased from Integrated DNA Technologies (Coralville, Iowa) or Thermo Fisher Scientific (Waltham, Mass.). Enzymes were purchased form New England Biolabs (Ipswich, Mass.). DNA purification kits were purchased from Qiagen (Venlo, Netherlands). All cultures were started from single colonies grown on LB agar isolated from freezer stocks stored in 15% glycerol. Overnight cultures of strains were grown in LB media at 30° C. in a rotary shaker at 250 r.p.m. When a selective pressure was necessary to for plasmid retention, media was supplemented with the appropriate antibiotics (carbenicillin, 100 μg/mL; kanamycin, 50 μg/mL; chloramphenicol, 34 μg/mL).

DNA Synthesis and Cloning

*Escherichia coli* K12 MG1655 was used to create the ΔlipB selection strain. Here we used a CRISPR-Cas9 assisted homologous recombination protocol, modified from Li et al.,[32] to delete the lipB coding sequence. Standard lambda red recombination[33] was used to introduce the deletion and Cas9 guided to lipB was used to destroy unmodified chromosomes. The repair template contained 30 bases upstream and downstream of the lagging strand of lipB.

NHL17 (*E. coli* K12 MG1655 ΔaraBAD ΔfadD::trc-CpFatB1.2-M4-287) strain was created from *E. coli* K12 MG1655 ΔaraBAD in the same manner by using a linear piece of dsDNA containing lacI-trc-CpFatB1.2-M4-287 between 500 base pairs of homology upstream and downstream of fadD coding sequence.

All plasmids made were constructed using Gibson Assembly of PCR products[34].

Random Mutagenesis of CpFatB1.2

The CpFatB1.2 library was constructed by error-prone PCR following the manufacturer's instruction (GeneMorph II, Agilent). The mutation frequency chosen was low (0 to 4.5 mutations/kb). The plasmid backbone was amplified by PCR using high fidelity polymerase Phusion. CpFatB1.2 library was assembled with designated backbones by Gibson assembly method. Primers used in for the creation of the library contained the start and stop codons in order to prevent mutations on them.

Lipoic Acid Selection

In order to find suitable conditions for the ΔlipB-based selection method, purified plasmid pBTRCK-CpFatB1.2 was transformed into *E. coli* ΔlipB strain and plated in MOPS minimal media agarose plates containing 0.2% glucose. In addition, the plates contained kanamycin to maintain the plasmid and different IPTG concentrations (0 μM, 10 μM, 20 μM, 30 μM and 50 μM IPTG) to titrate the amount of CpFatB1.2 present in the cells. The 20 μM induction condition was chosen because at this level of CpFatB1.2 expression, the cells needed an extra day (4 days) for rescuing growth compared to higher induction levels (3 days).

Gibson assembly reaction mixtures (2 µL) containing a CpFatB1.2 library was transformed into 100 µL of electrocompetent *E. coli* ΔlipB. Following electroporation (1 mm cuvette, 2500 mV), 900 µL of fresh LB was added and cells were allowed to recover for 1.5 hours. In order to remove any remaining lipoic acid from the rich media the cells were washed 3 times by spinning down at 10,000 rpm for 1 min followed by the 1 mL of M9 minimal media was added and the cells were resuspended. Finally, the washed cells were plated on MOPS minimal media-agarose plates containing 0.2% glucose and Kanamycin. The plates were incubated at 30° C. and after 3 days, the chosen 90 putative mutants growing colonies were streaked on LB plates with Kanamycin. The plates were incubated at 37° C. overnight to confirm the colony growth. Finally, the plasmids were purified and sequenced.

Fatty Acid Production

Plasmid based expression of thioesterases was performed in *E. coli* RL08ara[35] transformed with the appropriate plasmid. NHL17 strain contains a chromosomal copy of CpFatB1.2-M4-287 and therefore no plasmid was added.

For validating the 90 CpFatB1.2 variants (FIG. 7B, FIG. 8B, Table 2) as well as the truncations of CpFatB1 (FIG. 3B) and truncations in CpFatB1.2-M4 (FIG. 10B), isolated plasmids were transformed into *E. coli* RL08ara and single colonies were used to inoculate overnight cultures in LB media with kanamycin. Overnight cultures were used to inoculate 50 mL LB media with 0.4% glycerol and kanamycin at an initial optical density ($OD_{600}$) of 0.05. Cultures were incubated at 37° C. with shaking in 250 mL shake flasks. When cultures reached an $OD_{600}$ of 0.2-0.3 cells were induced with IPTG and moved to 30° C. for 24 hr. Mutants M1-M10 were tested using 20 µM IPTG (FIG. 7B). Mutants M3, M4, and M11-M90 (FIG. 8B), truncations of CpFatB1 (FIG. 3B) and truncations in CpFatB1.2-M4 (FIG. 10B) where induced with 1 mM IPTG.

For experiments designed to test for high octanoic acid production (FIGS. 9, 11, 14A, and 14B) overnight cultures as described above were used to inoculate 50 mL of medium described in Kim, et al.[25] with the following changes: 1.39 mM Na2HPO4, no biotin, thiamine or sodium selenite added.

Minimal media experiments were carried out in MOPS minimal media[24] containing 1% glucose and 0.240 mM $K_2HPO_4$ in order to create phosphate limiting conditions[36].

Fatty Acid Extraction and Quantification

After 24 h post-induction, 2.5 mL of culture was transferred to 10 mL glass centrifuge tubes. 50 µL of 12.5 mg/mL nonanoic acid, and 1.25 mg/ml pentadecanoic acid in ethanol solution was added as an internal standard. The nonanoic acid internal standard was used to quantify octanoic acid and the pentadecanoic acid internal standard was used to quantify $C_{10}$-$C_{18}$ chain lengths. Extraction and methylation process followed protocols described previously[9].

Protein Expression and Purification of Apo-Acyl Carrier Protein (ACP)

*E. coli* K12 MG1655 acyl carrier protein (ACP) was cloned into the pET28t vector system fused to a N-terminal polyhistidine tag coding the following peptide: MGSSHHHHHHSSENLYFQGGGG. The plasmid was transformed into BL21 (DE3) competent cells and grown LB media at 37° C. until $OD_{600}$ was 0.6-0.8. Cells were cooled to 18° C. in ice water, induced with 1 mM IPTG and incubated overnight at 18° C. with shaking. Cells were harvested by centrifugation at 8,000×g and pellets were stored at −80° C. for later use. Frozen pellets were resuspended in lysis buffer (50 mM $Na_2HPO_4$ pH8, 20 mM imidazole, 300 mM NaCl and 10% glycerol), sonicated, centrifuged at 12,000 RPM and filtered to clear the lysate. ACP was purified by Ni-NTA column following the manufacture's instruction (GE Healthcare Life Sciences). To the ACP protein solution, Tev protease was added at a molar ratio of 1:20 and dialysed against 50 mM Tris, pH 7.5 overnight. Cleaved ACP was then passed through the Ni-NTA column to remove Tev protease and the His tag peptide. The flow through was dialyzed against 50 mM $Na_2HPO_4$ pH8, 10% Glycerol for subsequent functionalization. The concentration of ACP was quantified via BCA assay (Thermo Fisher) using manufacturer's instructions.

Protein Expression and Purification of *Vibrio Harveyi* AasS and *Basillus sustilis* SfP, CpFatB1.2 and CpFatB1.2-M4

*Vibrio Harveyi* AasS, *Basillus sustilis* SfP, CpFatB1.2 and CpFatB1.2-M4 were cloned into pET28t vector system with an N-terminal poly-histidine tag as described for ACP. Proteins were purified as described for ACP with the exception that no Tev protease reaction was performed. Following purification in Ni-NTA column, proteins were concentrated and buffer-exchanged into 50 mM $Na_2HPO_4$ pH8, 30% Glycerol. Concentration of these proteins was quantified using the following extinction coefficients (280 nm): 67520 $M^{-1}cm^{-1}$ for AasS, 30620 $M^{-1}cm^{-1}$ SfP, 56295 $M^{-1}cm^{-1}$ for CpFatB1.2, and 50795 $M^{-1}cm^{-1}$ for CpFatB1.2-M4.

Synthesis of Octanoyl-ACP

Octanoyl ACP synthesis was carried out by first functionalizing a 500 µM mixture of apo-ACP and holo-ACP from *E. coli* into holo-ACP by incubating at 37° C. for 1 hr with 5 µM purified SfP, 10 mM $MgCl_2$, 5 mM Coenzyme A in 100 mM $Na_2HPO_4$ pH8 as has been described elsewhere[26]. Next, 5 µM of purified AssS, 10 mM ATP and 5 mM sodium octanoate are added to the reaction mixture and incubated overnight at 37° C. Samples were taken in between steps for characterization by HPLC. After incubation, octanoyl-ACP was passed through a Ni-NTA column to remove both AasS and SfP followed by addition of an equimolar amount of 5,5′-dithiobis(2-nitrobenzoic acid) (DTNB) in order to react all the CoA remaining prior to the assays. DTNB and yellow TNB produced in this step were subsequently dialyzed out against 100 mM $Na_2HPO_4$, pH8, 10% glycerol before carrying out the enzymatic assays. Octanoyl-ACP concentration was quantified using BCA assay.

Liquid Chromatography of Octanoyl-ACP

To verify the functionalization and purity of Acyl carrier protein species, samples were separated via HPLC using a Harmony C4 column 2.1×150 mM, 3.5 µm (ES Industries). Mobile phases consisted of (1) aqueous solution of 0.05% (w/v) Trifluoroacetic acid and 0.05% (w/v) formic acid, and (2) 0.05% (w/v) Trifluoroacetic acid and 0.05% (w/v) formic acid in acetonitrile. The samples were separated over 20 min by imposing a gradient of 20% aqueous mobile phase to 98% acetonitrile mobile phase. The oven temperature was kept at 30° C. and the flow rate was 0.2 ml/min with an injection volume of 10 μL. Prior to injection, the samples were buffer exchanged into 50 mM ammonium acetate and treated with 0.1% (w/v) formic acid In-vitro Analysis of CpFatB1.2-M4

Octanoyl-ACP thioesterase activity of CpFatB1.2, CpFatB1.2-M4 and TesA-R3.M4[9] was analyzed in vitro by tracking the formation of holo-ACP using the thiol-dependant reduction of 5,5'-dithiobis(2-nitrobenzoic acid) (DTNB).TNB formation was monitored every 10 s for 2 min at Absorbance at 412 nm with a NanoDrop 2000c (Thermo Scientific) at a path length of 10 mm. Octanoyl-ACP was added to the assay in concentrations ranging 0-400 μM (quantified via BCA assay). The conditions for the assay were as follows: 40 nM thioesterase, 8 μg/mL BSA, 250 μM DTNB, 100 mM phosphate buffer pH7.4, in 1 mL reaction volume. Assay was started with the addition of the thioesterase. All concentrations except 400 μM were tested in triplicate.

Structural Modeling of CpFatB1.2-M3 and CpFatB1.2-M4-287

The CpFatB1.2 model was created using homology modeling of the CpFatB1.2 sequence and BTE (PDB: 5×04structure) as the template structure. Subsequently, the amino acid changes to create energy-minimized structures of the CpFatB1.2 mutants were made using Mutator.[37] The catalytic residues Asp220, Asn222, His224, Glu258, and Cys259 were identified using the *Umbellularia californica* thioesterase UaFatB1 (BTE) structure (PDB: 5×04) as a guide where the analogous residues have been reported to be Asp281, Asn283, His285, Glu319, and Cys320.11 Cys320 mutants were seen to retain non-negligible catalytic activities, hence Cys259 was excluded from the list of catalytic residues in CpFatB1.2 model. The octanoyl-ACP (substrate) was docked such that the carbonyl carbon (C=O) of the thioester bond of the acyl-ACP molecule was close to the side-chain O atoms of Asp220 and Glu258. The catalytic distances corresponding to Asp220 and Glu258 were measured to be 3.5 and 3.7 Å, respectively. Subsequently, the BTE structure was used to identify the acyl-binding pocket residues which are important for controlling substrate specificity.[29] In order to understand the biophysical mechanism that underpins the catalytic activity in each of the enzyme variants, noncovalent contact maps were constructed similar to Mendonça et al.[30] These contact networks (see FIGS. 17A and 18A) have been used to explain the possible path by which mutations away from the binding crevice or active site could affect enzyme activity. Python 2.7 scripts were written to identify heteroatoms of residues within 6 Å of an altered residue of the CpFatB1.2 mutant. Each of these residues form nodes of the contact map and edges are drawn to show that a noncovalent contact exists. The same procedure is repeated for the nodes identified in the previous step and a cascade of interactions is mapped. The process is terminated when one or more catalytic and acyl-binding pocket residues are identified within 6 Å of a residue identified in previous step. Subsequently, we parse the obtained information to classify the noncovalent contacts (edges) as hydrophobic or polar, depending on the nature of atoms involved in the interaction. Finally, we visualize the contacts using PyMOL visualizing software.

RESULTS

Establishment of a Baseline Thioesterase

*Cupheapalustris* FatB1 thioesterase (CpFatB1) is highly selective for C8:0-ACP when expressed in *E. coli*[23] albeit with lower activity relative to *E. coli* 'TesA and other commonly used thioesterases[6,8]. The lower activity likely comes from a combination of poor expression and/or poor specific activity. Plant thioesterases are often associated with the chloroplast membrane and native genes contain membrane localization sequences. When heterologously expressed, these sequences can lead to insoluble or aggregated proteins. Therefore, one must construct an N-terminal truncation of a plant thioesterase to obtain high levels of soluble protein. We constructed three N-terminal truncations of CpFatB1 (SEQ ID NO:1 (nucleotide sequence) and SEQ ID NO:2 (protein sequence)) based on prior work[15] and sequence alignment—CpFatB1.2 (SEQ ID NO:3 (nucleotide sequence) and SEQ ID NO:4 (protein sequence)), CpFatB1.3 (SEQ ID NO:5 (nucleotide sequence) and SEQ ID NO:6 (protein sequence)), and CpFatB1.4 (SEQ ID NO:7 (nucleotide sequence) and SEQ ID NO:8 (protein sequence)). Each was cloned into a high copy plasmid, pTRC99a (FIGS. 3A and 3B, Table 1) and transformed into *E. coli* RL08ara (ΔfadD) for testing. Each strain was grown in LB supplemented with 0.4% glycerol and 1 mM IPTG. Expression of CpFatB1.2 generated the highest titer of octanoic acid under these conditions. Therefore, we used this gene sequence as a starting point in our mutagenesis studies.

TABLE 1

Strains and plasmids used in the present examples.

| Strain/plasmid | Genotype | Source |
| --- | --- | --- |
| *E. coli* K12 MG1655 | F− λ− ilvG− rfb-50 rph-1 | CGSG |
| ΔlipB | K12 MG1655 ΔlipB | This work |
| RL08ara | K-12 MG1655 ΔaraBAD ΔfadD | 13 |
| araBAD | K-12 MG1655 ΔaraBAD | 38 |
| NHL17 | K-12 MG1655 ΔaraBAD ΔfadD::trcCpFatB1.2-M4-287 | This work |
| pBTRCK | ptrc promoter, pBBR1 origin, Kan$^R$ | 39 |
| ptrc99a | ptrc promoter, pBR322 origin, Amp$^R$ | 40 |
| pBad33 | pBAD promoter, pACYC origin, Cm$^R$ | 41 |
| pBad33-CpFatB1.2 | pBad33 with *Cuphea palustris* CpFatB1 gene truncated at MLLTAIT | This work |
| ptrc99a-CpFatB1 | ptrc99a with *Cuphea palustris* CpFatB1 full gene sequence | This work |

TABLE 1-continued

Strains and plasmids used in the present examples.

| Strain/plasmid | Genotype | Source |
| --- | --- | --- |
| ptrc99a-CpFatB1.2 | ptrc99a with *Cuphea palustris* CpFatB1 gene truncated at MLLTAIT | This work |
| ptrc99a-CpFatB1.3 | ptrc99a with *Cuphea palustris* CpFatB1 gene truncated at MKSKRPN | This work |
| ptrc99a-CpFatB1.4 | ptrc99a with *Cuphea palustris* CpFatB1 gene truncated at MGLVFRQ | This work |
| pBTRCK-CpFatB1.2 | pBTRCK with *Cuphea palustris* CpFatB1.2 under trc promoter | This work |
| pBTRCK-CpFatB1.2-M4 | pBTRCK with CpFatB1.2-M4 sequence | |
| pBTRCK-CpFatB1.2-M4-287 | pBTRCK with CpFatB1.2-M4 sequence truncated | |
| pBTRCK-CpFatB1.2-M4-288 | pBTRCK | |
| pBTRCK-CpFatB1.2-M4-289 | pBTRCK | |
| pBTRCK-CpFatB1.2-M4-290 | pBTRCK | |
| pBTRCK-CpFatB1.2-M4-291 | pBTRCK | |
| ptrc99a-CpFatB1.2-M3 | | |
| ptrc99a-CpFatB1.2-M4 | | |
| ptrc99a-CpFatB1.2-M9 | | |
| ptrc99a-CpFatB1.2-M4-287 | | |

Development of a Lipoic Acid-Based Selection

As discussed above, *E. coli* requires small amounts of lipoic acid to enable pyruvate decarboxylase activity under aerobic conditions. As little as 50 μM (7.2 mg/L) octanoic acid can restore growth of an *E. coli* ΔlipB strain[21]. This amount is less than the ~200 mg/L of octanoic acid produced from the plasmid-based CpFatB1.2 described above. Therefore, to use the lipoic acid requirement as a selection, the overall activity of the thioesterase must be reduced, such that the baseline enzyme cannot complement a ΔlipB mutation. To do this we reduced the expression of CpFatB1.2 by swapping the promoter for a weaker $P_{araBAD}$ and moved the expression cassette to a plasmid maintained at a lower copy number (pACYC origin). Unfortunately, *E. coli* ΔlipB pBAD33-CpFatB1.2 grew on MOPS-minimal media-agar[24] containing 0.2% arabinose to induce expression (FIG. 4). In a second attempt to reduce activity, we cloned the original $P_{TRC}$-CpFatB1.2 expression cassette onto a low-copy plasmid, pBTRCK (pBBR1 origin), and used a series of low IPTG concentrations to vary expression (FIG. 5). Interestingly, cells grown on plates with 20 μM IPTG took an extra day to grow (4 days), compared to cells grown (3 days) on the same media with 30 μM IPTG (FIG. 5). Given this difference in growth rates, we hypothesized that we had found a window in which cells expressing thioesterase variants with improved specific activity or mutations that increased protein production would be identified before the cells carrying the parent gene became visible colonies. Therefore, we used the low-copy pBTRCK plasmid and 20 μM IPTG in our mutagenesis study.

Library of CpFatB1.2 Mutants

To introduce mutations, we generated a library of CpFatB1.2 variants by error-prone PCR covering the full coding sequence. PCR products were cloned into pBTRCK, plasmids were transformed into *E. coli* ΔlipB, and cells were plated on MOPS minimal media containing 20 μM IPTG. Ninety colonies appeared after three days (FIG. 6). To validate each hit, plasmids were isolated from each colony, retransformed into fresh *E. coli* ΔlipB cells, and cells were grown under selecting conditions. All of the variants rescued growth within three days (not shown), indicating that growth-conferring mutations were plasmid-based. When cultured in liquid media, cells harboring the variant thioesterases produced more octanoic acid than cultures expressing the original CpFatB1.2 (FIG. 7B). In particular, variants CpFatB1.2-M3 (SEQ ID NO:9 (nucleotide sequence) and SEQ ID NO:10 (protein sequence)), CpFatB1.2-M4 (SEQ ID NO:11 (nucleotide sequence) and SEQ ID NO:12 (protein sequence)), and CpFatB1.2-M9 exhibited 4-fold, 5.3-fold and 2.3-fold improvements, respectively, when expressed from the low-copy plasmid. After analyzing the first 10 mutants, we repeated the protocol on the remainder of the 90 putative mutants, finding several additional improved variants, but none superior to M3 or M4 (FIG. 8B).

Plasmids isolated from each of the hits that generated more than a 2-fold increase in octanoic acid were sequenced. A small family of mutations was observed in these hits. Interestingly, one mutation, D293V appeared independently in five of the sequenced mutants, CpFatB1.2-M20, CpFatB1.2-M40, CpFatB1.2-M47, CpFatB1.2-M66, and CpFatB1.2-M73. Mutant CpFatB1.2-M40 and CpFatB1.2-M66 contained only the D293V mutation, indicating that it provided on average a 2.3-fold increase in activity over CpFatB1.2. In addition to two point mutations (N28S, I65M), CpFatB1.2-M4, the best variant, contained a frame-shifting deletion which introduced a premature stop codon. CpFatB1.2-M3 contained two mutations (A59S and K296R) that were also found in other mutants. Given the superior performance of CpFatB1.2-M3, CpFatB1.2-M4, and CpFatB1.2-M9, we focused the remainder of the study on these variants.

Mutants CpFatB1.2-M3, CpFatB1.2-M4, and CpFatB1.2-M9 were subcloned into high copy plasmid pTRC99a to determine if the improvements found under screening conditions would be maintained under optimal production conditions. Plasmids were transformed into *E. coli* RL08ara (ΔfadD) and cells were grown in MOPS media enriched[25] with tryptone, yeast extract, and 1 mM IPTG to maximize induction. Cells expressing the M3 and M4 variants produced 1751 mg/L and 1263 mg/L of octanoic acid respectively. These titers represent a 3-4 fold-increase relative to cells expressing CpFatB1.2 which produced 375 mg/L (FIG. 9). Cells expressing the M9 variant produced approximately 500 mg/L, a smaller relative value to CpFatB1.2 than seen under screening conditions. Conveniently, the increased activity did not come at the expense of octanoic acid selectivity. Variants M3 (92 mol %) and M4 (94 mol %) generated equivalent if not larger percentages of octanoic acid compared to CpFatB1.2 (89% mol). These data show that the lipoic acid selection was capable of identifying useful mutations.

Characterization of M4 Variant In Vivo

The CpFatB1.2-M4 ($\Delta A_{54}$, N28S, I65M) variant contained two point mutations and an early nucleotide deletion ($\Delta A_{54}$) that led the original open reading frame to an early stop codon (FIG. 10A). Since CpFatB1.2-M4 is active, we suspected that translation was restarting at a different in-frame methionine using a suboptimal ribosome binding site (RBS). If true, we hypothesized that the M4 variant could generate more activity, if expressed with an optimal RBS. To determine which protein was being made, we cloned five in-frame CpFatB1.2-M4 variants based on the next five in frame methionines as start codons, creating CpFatB1.2-M4-287 (SEQ ID NO:13 (nucleotide sequence) and SEQ ID NO:14 (protein sequence)), -288, -289, -290 and -291. These genes were cloned into a pBTRCk vector to position the new start adjacent to the original, strong RBS. Plasmids harboring each variant were individually transformed into RL08ara ($\Delta fadD$) strain and cells were grown in LB supplemented with 0.4% glycerol and 1 mM IPTG. Only variant CpFatB1.2-M4-287 showed a significant level of octanoic acid production (FIG. 10B). Moreover, variant CpFatB1.2-M4-287 generated more octanoic acid than the isolated variant CpFatB1.2-M4. This suggests that the hypothesis of CpFatB1.2-M4 being translated from a non-specific RBS was correct.

Further, the pFatB1.2-M4-287 demonstrated a ~20-fold increase in octanoic acid production under the low expression conditions tested (FIG. 10B), suggesting that more activity could be obtained if overexpressed. Therefore, we cloned CpFatB1.2-M4-287 onto a high copy plasmid, pTRC99a, transformed the plasmid into E. coli RL08ara ($\Delta fadD$), and cultured cells in MOPS media enriched[25] with tryptone and yeast extract (see methods) and different concentrations of IPTG to optimize expression (FIG. 11). The resulting fatty acid profiles extracted from these cultures showed that a subsaturating concentration of 50 µM IPTG gave maximum activity. At saturating concentrations of 1 mM IPTG, we observed a growth defect and a drastic decrease in $C_{16}$ fatty acid species (FIG. 11). This data strongly suggested that we had dramatically increased the specific activity of CpFatB1, because it could no longer be maximally expressed.

Finally, we made combinations of the constitutive mutations found in CpFatB1.2-M4-287 (N28S, I65M, 287-truncation) to determine which contributed to enhanced activity. CpFatB1.2 variants containing 1, 2 or all three mutations were cloned into pTRC99A and cultured in E. coli RL08ara as described for FIG. 11. As a negative control, we cloned a variant with a H224A mutation that renders the enzyme catalytically inactive. Interestingly, only I65M was observed to increase activity above the baseline variant, CpFatB1.2 (FIG. 12). Only the triple mutant was able to drastically outperform the CpFatB1.2. This also suggests a possible explanation for the CpFatB1.2-M4-288 truncation (which excludes the N28S mutation) being less active than the CpFatB1.2-M4 (FIG. 10B).

Characterization of M4 Variant In Vitro

Our in vivo data suggested that the M4 variant had increased specific activity towards $C_8$-acyl ACPs. To prove this hypothesis, we measured the reaction rate in vitro using Ellman's reagent (DTNB) to monitor release of free thiols in holo-ACP (FIG. 13A). As hydrolysis of octanoyl-ACP occurs, holo-ACP formed reacts with DTNB forming the colored compound TNB that absorbs light at 412 nm. For substrate, we synthesized octanoyl-ACP in vitro from apo-ACP (purified from E. coli), coenzyme A (which donated the 4'-phosphopantetheine prosthetic group to convert apo-ACP to holo-ACP), and octanoate, using methods described elsewhere[26]. Complete synthesis of octanoyl-ACP was confirmed by HPLC (FIG. 13B). Using the DTNB assay, we measured the initial rate of the thioesterase reaction for a range of substrate concentrations. We found that mutant CpFatB1.2-M4 has dramatically improved activity towards octanoyl-ACP compared to both CpFatB1.2 as well as a TesA variant (TesA-R3.M4) that we designed computationally in previous work[9] to produce octanoic acid. The major contribution to CpFatB1.2-M4 improvement observed was due to a 15.7 fold increase in $V_{max}$ over CpFatB1.2 while the $K_m$ remained relatively low (FIGS. 13C and 13D). Interestingly, we found that our TesA-R3.M4 mutant had a high $V_{max}$ as well but very low affinity for octanoyl-ACP with $K_m$ 17-fold higher than CpFatB1.2-M4. These data confirm that our lipoic acid selection isolated a variant with improved specific activity.

Optimizing Expression in E. Coli

When building stable, industrially-relevant strains, it is beneficial to remove any requirement for antibiotics for maintaining plasmids and to reduce the cellular burden associated with protein overexpression. In other words, it is preferable to achieve a desired activity by increasing specific activity of essential enzymes such that each enzyme can be expressed at a modest level. Here, we wanted to test the ability of CpFatB1.2M4 to provide thioesterase activity when expressed from low copy plasmids or the chromosome. Therefore, we created the low copy plasmid, pBTRCK-CpFatB1.2-M4, with a n optimized RBS and tested FFA production under various induction levels (FIG. 14A). CpFatB1.2-M4 was optimally expressed from this construct when no IPTG was added, suggesting that the copy number could be decreased further. Moreover, at high induction we observed a growth defect, which reduced the final octanoic acid titers, a phenomenon that has been seen before[13]. Next, we took the same construct and inserted it into the E. coli chromosome in the fadD locus using CRISPR-Cas9 mediated homologous recombination. This yielded E. coli strain NHL17 (FIG. 14B, Table 1). As can be seen from FIG. 14B, a single copy CpFatB1.2-M4 in the chromosome when fully induced was sufficient to yield the levels of production obtained from the plasmid.

TABLE 2

Fatty acid profile of 90 putative mutants. Each of the colonies selected was grown to isolate its plasmid. Isolate plasmids were transformed into the RL08ara (ΔfadD) strain and grown in LB 0.4% glycerol and 20 µM IPTG (mutants M1-M10) and 1 mM IPTG (mutants M3, M4, and M11-M90).

| Mutant | # Residue Changes | Mutations | C8:0 (mg/L) | C10:0 (mg/L) | C10:1 (mg/L) | C12:0 (mg/L) | C12:1 (mg/L) | C14:0 (mg/L) | C14:1 (mg/L) | C16:0 (mg/L) | C16:1 (mg/L) | C18:0 (mg/L) | C18:1 (mg/L) | Total FFA (mg/L) | Induction Lev Tested (µM) | C8:0 Fold Increase Relative to CpFatB1.2 at Same Induction Level |
|---|---|---|---|---|---|---|---|---|---|---|---|---|---|---|---|---|
| CpFatB1.2 | 0 | n/a | 12.4<br>20.7 ± 1.75 | 5.6<br>1.7 ± 0.48 | 0.9<br>1.5 ± 0.07 | 0.0<br>0.0 | 1.5<br>1.7 ± 0.12 | 0.6<br>0.7 ± 0.1 | 9.4<br>8.4 ± 1.1 | 10.1<br>13.2 ± 1.2 | 52.6<br>56.0 ± 2.9 | 0.0<br>0.0 | 0.0<br>1.3 ± 0.04 | 93.2<br>107.1 | 20<br>1000 | 1.0<br>1.0 |
| CpFatB1.2-M1 | 0 | n/a | 20.7 | 4.7 | 1.6 | 0.0 | 1.8 | 0.8 | 9.8 | 12.8 | 58.2 | 0.0 | 0.0 | 110.2 | 20 | 1.7 |
| CpFatB1.2-M2 | 3 | M29T, T117S, Q163L | 15.0 | 2.8 | 1.3 | 0.0 | 1.6 | 0.8 | 10.5 | 17.5 | 69.7 | 0.0 | 1.5 | 120.7 | 20 | 1.2 |
| CpFatB1.2-M3 | 2 | A59S, K296R | 49.5<br>82.9 ± 5.86 | 2.7<br>1.8 ± 0.34 | 4.8<br>7.0 ± 0.26 | 0.6<br>1.0 ± 0.04 | 3.6<br>4.9 ± 0.09 | 1.1<br>1.4 ± 0.04 | 9.4<br>8.6 ± 0.4 | 11.7<br>10.1 ± 0.3 | 51.8<br>51.1 ± 0.8 | 0.0<br>0 | 1.4<br>1.1 ± 0.9 | 136.7<br>169.9 | 20<br>1000 | 4.0<br>4.0 |
| CpFatB1.2-M4 | 2 | ΔA54 (new start codon at M19), N28S, I65M | 66.8<br>155.3 ± 16.2 | 2.9<br>2.1 ± 0.18 | 4.8<br>10.8 ± 0.96 | 0.6<br>1.3 ± 0.12 | 3.8<br>6.1 ± 0.26 | 0.9<br>1.6 ± 0.1 | 8.3<br>8.8 ± 0.4 | 12.6<br>9.1 ± 0.8 | 46.9<br>47.8 ± 1.6 | 0.0<br>0 | 1.4<br>1.2 ± 1.0 | 149.0<br>243.9 | 20<br>1000 | 5.4<br>7.5 |
| CpFatB1.2-M5 | 2 | W17R, T204S | 24.9 | 4.3 | 1.9 | 0.0 | 2.0 | 0.7 | 8.4 | 12.1 | 52.8 | 0.0 | 0.0 | 107.0 | 20 | 2.01 |
| CpFatB1.2-M6 | 2 | L251M, L265I, | 17.4 | 4.2 | 1.5 | 0.0 | 1.6 | 0.7 | 8.5 | 12.8 | 58.4 | 0.0 | 0.0 | 105.0 | 20 | 1.40 |
| CpFatB1.2-M7 | 0 | n/a | 20.5 | 5.9 | 1.3 | 0.0 | 1.8 | 0.6 | 7.7 | 12.6 | 56.4 | 0.0 | 1.3 | 108.0 | 20 | 1.65 |
| CpFatB1.2-M8 | 2 | K15E, S207T | 16.4 | 5.5 | 1.1 | 0.0 | 1.6 | 0.7 | 8.6 | 10.8 | 54.3 | 0.0 | 0.0 | 99.0 | 20 | 1.32 |
| CpFatB1.2-M9 | 1 | R261S | 28.6 | 4.4 | 2.4 | 0.0 | 2.5 | 0.8 | 8.4 | 11.4 | 53.3 | 0.0 | 0.0 | 111.8 | 20 | 2.31 |
| CpFatB1.2-M10 | 0 | n/a | 12.4 | 5.6 | 0.9 | 0.0 | 1.5 | 0.6 | 9.4 | 10.1 | 52.6 | 0.0 | 0.0 | 93.2 | 20 | 1.27 |
| CpFatB1.2-M11 | ND | ND | 26.4 | 0.0 | 1.0 | 0.0 | 1.7 | 0.0 | 7.6 | 12.1 | 69.0 | 0.0 | 14.5 | 132.2 | 1000 | 1.3 |
| CpFatB1.2-M12 | 1 | M136V | 61.0 | 1.3 | 2.8 | 0.0 | 3.8 | 0.0 | 7.9 | 11.8 | 60.2 | 0.0 | 21.4 | 170.2 | 1000 | 2.9 |
| CpFatB1.2-M13 | ND | ND | 13.9 | 0.0 | 0.0 | 0.0 | 0.8 | 0.0 | 3.3 | 3.7 | 47.1 | 0.0 | 11.9 | 80.7 | 1000 | 0.7 |
| CpFatB1.2-M14 | ND | ND | 16.5 | 0.0 | 0.9 | 0.0 | 1.4 | 0.0 | 5.3 | 8.9 | 68.5 | 0.0 | 15.3 | 116.8 | 1000 | 0.8 |
| CpFatB1.2-M15 | ND | ND | 15.7 | 0.0 | 0.7 | 0.0 | 1.1 | 0.0 | 3.1 | 3.7 | 45.5 | 0.0 | 12.2 | 81.9 | 1000 | 0.8 |
| CpFatB1.2-M16 | 1 | K296R | 43.2 | 0.8 | 2.3 | 0.0 | 3.0 | 0.0 | 6.9 | 10.7 | 61.8 | 0.0 | 19.2 | 147.8 | 1000 | 2.1 |
| CpFatB1.2-M17 | ND | ND | 26.9 | 0.6 | 1.5 | 0.0 | 1.8 | 0.0 | 9.4 | 14.2 | 68.0 | 0.0 | 18.0 | 140.3 | 1000 | 1.3 |

TABLE 2-continued

Fatty acid profile of 90 putative mutants. Each of the colonies selected was grown to isolate its plasmid. Isolate plasmids were transformed into the RL08ara (ΔfadD) strain and grown in LB 0.4% glycerol and 20 μM IPTG (mutants M1-M10) and 1 mM IPTG (mutants M3, M4, and M11-M90).

| Mutant | # Residue Changes | Mutations | C8:0 (mg/L) | C10:0 (mg/L) | C10:1 (mg/L) | C12:0 (mg/L) | C12:1 (mg/L) | C14:0 (mg/L) | C14:1 (mg/L) | C16:0 (mg/L) | C16:1 (mg/L) | C18:0 (mg/L) | C18:1 (mg/L) | Total FFA (mg/L) | Induction Lev Tested (μM) | C8:0 Fold Increase Relative to CpFatB1.2 at Same Induction Level |
|---|---|---|---|---|---|---|---|---|---|---|---|---|---|---|---|---|
| CpFatB1.2-M18 | ND | ND | 27.2 | 1.1 | 1.5 | 0.0 | 2.2 | 0.0 | 10.0 | 17.4 | 86.7 | 0.0 | 24.2 | 170.2 | 1000 | 1.3 |
| CpFatB1.2-M19 | ND | ND | 18.5 | 1.1 | 0.9 | 0.0 | 1.5 | 0.0 | 6.9 | 12.2 | 65.5 | 0.0 | 16.6 | 123.1 | 1000 | 0.9 |
| CpFatB1.2-M20 | 2 | W17ST OP D293V | 61.5 | 0.7 | 3.4 | 0.0 | 3.6 | 0.0 | 7.0 | 8.7 | 57.2 | 0.0 | 18.3 | 160.3 | 1000 | 3.0 |
| CpFatB1.2-M21 | ND | ND | 17.4 | 0.0 | 0.9 | 0.0 | 1.9 | 0.0 | 10.1 | 13.2 | 63.5 | 1.1 | 14.5 | 122.7 | 1000 | 0.8 |
| CpFatB1.2-M22 | ND | ND | 38.9 | 0.0 | 2.0 | 0.0 | 3.2 | 0.0 | 9.1 | 13.3 | 60.0 | 1.0 | 19.1 | 146.6 | 1000 | 1.9 |
| CpFatB1.2-M23 | ND | ND | 21.5 | 0.0 | 1.2 | 0.0 | 2.3 | 0.0 | 9.2 | 12.7 | 60.4 | 0.9 | 15.5 | 123.7 | 1000 | 1.0 |
| CpFatB1.2-M24 | ND | ND | 17.4 | 0.0 | 1.0 | 0.0 | 2.0 | 0.0 | 10.6 | 13.8 | 69.2 | 1.5 | 13.6 | 129.1 | 1000 | 0.8 |
| CpFatB1.2-M25 | ND | ND | 17.5 | 0.0 | 1.0 | 0.0 | 2.0 | 0.0 | 11.9 | 14.3 | 63.3 | 1.0 | 14.9 | 125.8 | 1000 | 0.8 |
| CpFatB1.2-M26 | ND | ND | 20.3 | 0.0 | 1.1 | 0.0 | 1.9 | 0.0 | 7.6 | 12.6 | 68.1 | 1.2 | 14.4 | 127.3 | 1000 | 1.0 |
| CpFatB1.2-M27 | ND | ND | 15.8 | 0.0 | 0.9 | 0.0 | 2.2 | 0.0 | 11.7 | 13.4 | 64.4 | 1.2 | 13.2 | 122.9 | 1000 | 0.8 |
| CpFatB1.2-M28 | ND | ND | 16.9 | 0.0 | 0.9 | 0.0 | 2.0 | 0.0 | 10.8 | 14.1 | 68.4 | 1.4 | 13.5 | 128.1 | 1000 | 0.8 |
| CpFatB1.2-M29 | ND | ND | 21.9 | 0.0 | 1.2 | 0.0 | 2.0 | 0.0 | 5.7 | 9.4 | 65.5 | 1.4 | 13.1 | 120.1 | 1000 | 1.1 |
| CpFatB1.2-M30 | 5 | M19T, G35D, T117S, T121A, M138I | 28.4 | 0.0 | 1.8 | 0.0 | 4.0 | 0.0 | 9.7 | 12.7 | 66.2 | 1.1 | 18.8 | 142.7 | 1000 | 1.4 |
| CpFatB1.2-M31 | ND | ND | 15.2 | 0.0 | 1.0 | 0.0 | 2.0 | 0.0 | 10.1 | 13.5 | 64.0 | 3.5 | 11.7 | 121.0 | 1000 | 0.7 |
| CpFatB1.2-M32 | 1 | R22H | 31.4 | 0.0 | 1.8 | 0.0 | 2.7 | 0.0 | 9.2 | 13.8 | 64.3 | 3.1 | 19.1 | 145.3 | 1000 | 1.5 |
| CpFatB1.2-M33 | ND | ND | 12.8 | 0.0 | 0.8 | 0.0 | 1.6 | 0.0 | 6.1 | 10.8 | 63.5 | 3.5 | 8.7 | 107.9 | 1000 | 0.6 |
| CpFatB1.2-M34 | ND | ND | 8.0 | 0.0 | 0.5 | 0.0 | 0.9 | 0.0 | 3.1 | 1.1 | 36.9 | 2.5 | 3.1 | 56.2 | 1000 | 0.4 |
| CpFatB1.2-M35 | ND | ND | 14.2 | 0.0 | 0.9 | 0.0 | 1.7 | 0.0 | 7.9 | 12.8 | 65.6 | 3.8 | 10.6 | 117.6 | 1000 | 0.7 |
| CpFatB1.2-M36 | ND | ND | 11.8 | 0.0 | 0.8 | 0.0 | 2.2 | 0.0 | 8.7 | 11.5 | 64.0 | 3.4 | 10.2 | 112.7 | 1000 | 0.6 |
| CpFatB1.2-M37 | ND | ND | 11.4 | 0.0 | 0.7 | 0.0 | 1.3 | 0.0 | 5.4 | 6.9 | 63.9 | 3.6 | 6.8 | 100.0 | 1000 | 0.6 |

TABLE 2-continued

Fatty acid profile of 90 putative mutants. Each of the colonies selected was grown to isolate its plasmid. Isolate plasmids were transformed into the RL08ara (ΔfadD) strain and grown in LB 0.4% glycerol and 20 μM IPTG (mutants M1-M10) and 1 mM IPTG (mutants M3, M4, and M11-M90).

| Mutant | # Residue Changes | Mutations | C8:0 (mg/L) | C10:0 (mg/L) | C10:1 (mg/L) | C12:0 (mg/L) | C12:1 (mg/L) | C14:0 (mg/L) | C14:1 (mg/L) | C16:0 (mg/L) | C16:1 (mg/L) | C18:0 (mg/L) | C18:1 (mg/L) | Total FFA (mg/L) | Induction Lev Tested (μM) | C8:0 Fold Increase Relative to CpFatB1.2 at Same Induction Level |
|---|---|---|---|---|---|---|---|---|---|---|---|---|---|---|---|---|
| CpFatB1.2-M38 | ND | ND | 12.1 | 0.0 | 0.7 | 0.0 | 1.2 | 0.0 | 4.6 | 6.1 | 61.1 | 3.3 | 9.2 | 98.5 | 1000 | 0.6 |
| CpFatB1.2-M39 | ND | ND | 17.3 | 0.0 | 1.1 | 0.0 | 1.9 | 0.0 | 6.5 | 12.3 | 76.2 | 4.6 | 11.2 | 131.0 | 1000 | 0.8 |
| CpFatB1.2-M40 | 1 | D293V | 43.1 | 0.0 | 2.9 | 0.0 | 3.7 | 0.0 | 7.4 | 10.0 | 56.0 | 2.8 | 17.1 | 143.1 | 1000 | 2.1 |
| CpFatB1.2-M41 | ND | ND | 8.6 | 0.0 | 0.0 | 0.0 | 1.0 | 0.0 | 3.3 | 2.4 | 39.8 | 0.7 | 6.8 | 62.6 | 1000 | 0.4 |
| CpFatB1.2-M42 | ND | ND | 8.3 | 0.0 | 0.5 | 0.0 | 1.0 | 0.0 | 3.6 | 3.8 | 48.0 | 0.8 | 9.6 | 75.7 | 1000 | 0.4 |
| CpFatB1.2-M43 | ND | ND | 13.8 | 0.0 | 0.8 | 0.0 | 1.6 | 0.0 | 5.5 | 8.9 | 71.5 | 1.2 | 15.5 | 118.8 | 1000 | 0.7 |
| CpFatB1.2-M44 | ND | ND | 16.0 | 0.0 | 0.9 | 0.0 | 2.0 | 0.0 | 6.6 | 12.8 | 62.2 | 1.2 | 13.3 | 115.0 | 1000 | 0.8 |
| CpFatB1.2-M45 | ND | ND | 8.4 | 0.0 | 0.5 | 0.0 | 1.0 | 0.0 | 3.2 | 3.5 | 42.6 | 0.7 | 9.0 | 69.0 | 1000 | 0.4 |
| CpFatB1.2-M46 | ND | ND | 14.2 | 0.0 | 0.8 | 0.0 | 1.6 | 0.0 | 5.1 | 9.2 | 63.5 | 1.2 | 11.2 | 106.7 | 1000 | 0.7 |
| CpFatB1.2-M47 | 3 | N146K, D293V, N309D | 69.2 | 0.0 | 4.3 | 0.0 | 4.6 | 0.0 | 6.1 | 8.9 | 62.7 | 1.2 | 21.0 | 178.0 | 1000 | 3.3 |
| CpFatB1.2-M48 | ND | ND | 24.7 | 0.0 | 1.3 | 0.0 | 2.2 | 0.0 | 7.4 | 11.1 | 58.8 | 1.0 | 12.7 | 119.3 | 1000 | 1.2 |
| CpFatB1.2-M49 | ND | ND | 8.3 | 0.0 | 0.5 | 0.0 | 1.0 | 0.0 | 3.4 | 3.6 | 45.0 | 0.8 | 9.9 | 72.5 | 1000 | 0.4 |
| CpFatB1.2-M50 | ND | ND | 18.1 | 0.0 | 1.0 | 0.0 | 1.3 | 0.0 | 4.7 | 7.6 | 62.7 | 1.2 | 9.1 | 105.7 | 1000 | 0.9 |
| CpFatB1.2-M51 | ND | ND | 13.2 | 0.0 | 0.0 | 0.0 | 1.5 | 0.0 | 6.1 | 0.0 | 61.9 | 0.0 | 11.8 | 94.5 | 1000 | 0.6 |
| CpFatB1.2-M52 | ND | ND | 7.9 | 0.0 | 0.0 | 0.0 | 0.9 | 0.0 | 3.0 | 0.0 | 39.5 | 0.0 | 5.8 | 57.2 | 1000 | 0.4 |
| CpFatB1.2-M53 | ND | ND | 14.7 | 0.0 | 0.0 | 0.0 | 1.5 | 0.0 | 4.7 | 0.0 | 60.0 | 0.0 | 9.3 | 90.2 | 1000 | 0.7 |
| CpFatB1.2-M54 | ND | ND | 9.9 | 0.0 | 0.0 | 0.0 | 1.2 | 0.0 | 4.6 | 0.0 | 60.5 | 0.0 | 12.6 | 88.8 | 1000 | 0.5 |
| CpFatB1.2-M55 | ND | ND | 23.5 | 0.0 | 0.0 | 0.0 | 2.0 | 0.0 | 5.9 | 0.0 | 55.3 | 0.0 | 13.1 | 99.9 | 1000 | 1.1 |
| CpFatB1.2-M56 | ND | ND | 16.0 | 0.0 | 0.0 | 0.0 | 2.0 | 0.0 | 7.7 | 0.0 | 56.9 | 0.0 | 12.6 | 95.2 | 1000 | 0.8 |
| CpFatB1.2-M57 | ND | ND | 19.8 | 0.0 | 0.0 | 0.0 | 2.0 | 0.0 | 7.1 | 0.0 | 60.5 | 0.0 | 14.4 | 103.8 | 1000 | 1.0 |
| CpFatB1.2-M58 | ND | ND | 20.2 | 0.0 | 0.0 | 0.0 | 2.3 | 0.0 | 9.3 | 0.0 | 57.5 | 0.0 | 15.1 | 104.3 | 1000 | 1.0 |
| CpFatB1.2-M59 | ND | ND | 18.6 | 0.0 | 0.0 | 0.0 | 1.7 | 0.0 | 6.0 | 0.0 | 64.6 | 0.0 | 13.4 | 104.4 | 1000 | 0.9 |

TABLE 2-continued

Fatty acid profile of 90 putative mutants. Each of the colonies selected was grown to isolate its plasmid. Isolate plasmids were transformed into the RL08ara (ΔfadD) strain and grown in LB 0.4% glycerol and 20 μM IPTG (mutants M1-M10) and 1 mM IPTG (mutants M3, M4, and M11-M90).

| Mutant | # Residue Changes | Mutations | C8:0 (mg/L) | C10:0 (mg/L) | C10:1 (mg/L) | C12:0 (mg/L) | C12:1 (mg/L) | C14:0 (mg/L) | C14:1 (mg/L) | C16:0 (mg/L) | C16:1 (mg/L) | C18:0 (mg/L) | C18:1 (mg/L) | Total FFA (mg/L) | Induction Lev Tested (μM) | C8:0 Fold Increase Relative to CpFatB1.2 at Same Induction Level |
|---|---|---|---|---|---|---|---|---|---|---|---|---|---|---|---|---|
| CpFatB1.2-M60 | ND | ND | 19.1 | 0.0 | 0.0 | 0.0 | 1.8 | 0.0 | 6.4 | 0.0 | 55.8 | 0.0 | 12.7 | 95.7 | 1000 | 0.9 |
| CpFatB1.2-M61 | ND | ND | 13.6 | 0.0 | 0.0 | 0.0 | 1.0 | 0.0 | 3.2 | 1.4 | 39.6 | 0.7 | 4.3 | 63.8 | 1000 | 0.7 |
| CpFatB1.2-M62 | ND | ND | 12.6 | 0.0 | 0.0 | 0.0 | 1.0 | 0.0 | 3.2 | 1.7 | 40.4 | 0.8 | 4.9 | 64.6 | 1000 | 0.6 |
| CpFatB1.2-M63 | ND | ND | 19.7 | 0.0 | 0.0 | 0.0 | 1.6 | 0.0 | 6.7 | 12.7 | 66.2 | 1.3 | 10.4 | 118.6 | 1000 | 1.0 |
| CpFatB1.2-M64 | ND | ND | 22.1 | 0.0 | 0.0 | 0.0 | 2.1 | 0.0 | 12.3 | 16.5 | 69.2 | 1.5 | 13.9 | 137.5 | 1000 | 1.1 |
| CpFatB1.2-M65 | ND | ND | 20.5 | 0.0 | 0.0 | 0.0 | 1.7 | 0.0 | 6.6 | 10.3 | 73.9 | 1.3 | 10.0 | 124.3 | 1000 | 1.0 |
| CpFatB1.2-M66 | 1 | D293V | 54.3 | 0.0 | 1.3 | 0.0 | 3.7 | 0.0 | 7.8 | 10.9 | 58.6 | 1.1 | 15.2 | 152.9 | 1000 | 2.6 |
| CpFatB1.2-M67 | ND | ND | 12.7 | 0.0 | 0.0 | 0.0 | 0.9 | 0.0 | 3.2 | 1.0 | 39.4 | 0.8 | 3.6 | 61.6 | 1000 | 0.6 |
| CpFatB1.2-M68 | 1 | T245N | 28.4 | 0.0 | 0.0 | 0.0 | 2.0 | 0.0 | 8.1 | 15.4 | 64.8 | 1.2 | 14.3 | 134.3 | 1000 | 1.4 |
| CpFatB1.2-M69 | ND | ND | 21.2 | 0.0 | 0.0 | 0.0 | 1.7 | 0.0 | 7.9 | 14.8 | 65.2 | 1.1 | 12.0 | 123.7 | 1000 | 1.0 |
| CpFatB1.2-M70 | ND | ND | 21.8 | 0.0 | 0.0 | 0.0 | 1.6 | 0.0 | 7.3 | 14.2 | 67.9 | 1.2 | 12.3 | 126.4 | 1000 | 1.1 |
| CpFatB1.2-M71 | 1 | M136I | 46.7 | 0.0 | 1.0 | 0.0 | 2.8 | 0.0 | 5.2 | 3.9 | 85.2 | 1.8 | 18.0 | 164.6 | 1000 | 2.3 |
| CpFatB1.2-M72 | ND | ND | 22.9 | 0.0 | 0.0 | 0.0 | 1.8 | 0.0 | 5.2 | 8.5 | 61.5 | 1.3 | 11.1 | 112.3 | 1000 | 1.1 |
| CpFatB1.2-M73 | 3 | V268I, R279H, D293V | 61.2 | 0.0 | 1.4 | 0.0 | 4.2 | 0.0 | 7.8 | 8.5 | 56.0 | 0.9 | 16.4 | 156.5 | 1000 | 3.0 |
| CpFatB1.2-M74 | ND | ND | 21.6 | 0.0 | 0.0 | 0.0 | 2.1 | 0.0 | 9.1 | 12.8 | 60.1 | 0.9 | 14.1 | 120.6 | 1000 | 1.0 |
| CpFatB1.2-M75 | ND | ND | 18.0 | 0.0 | 0.0 | 0.0 | 1.4 | 0.0 | 4.3 | 7.3 | 50.2 | 1.0 | 9.2 | 91.2 | 1000 | 0.9 |
| CpFatB1.2-M76 | 2 | K23E, L86Q | 46.6 | 0.0 | 0.6 | 0.0 | 2.5 | 0.0 | 6.6 | 11.9 | 58.6 | 0.9 | 16.9 | 144.6 | 1000 | 2.2 |
| CpFatB1.2-M77 | ND | ND | 21.4 | 0.0 | 0.0 | 0.0 | 1.9 | 0.0 | 8.2 | 14.4 | 62.9 | 1.1 | 15.5 | 125.4 | 1000 | 1.0 |
| CpFatB1.2-M78 | ND | ND | 28.2 | 0.0 | 0.6 | 0.0 | 2.4 | 0.0 | 8.7 | 12.6 | 66.9 | 1.2 | 15.6 | 135.7 | 1000 | 1.4 |
| CpFatB1.2-M79 | 3 | V9M, K15E, E236A | 42.0 | 0.0 | 0.0 | 0.0 | 3.3 | 0.0 | 8.5 | 12.6 | 59.1 | 1.0 | 17.9 | 144.9 | 1000 | 2.0 |
| CpFatB1.2-M80 | ND | ND | 19.9 | 0.0 | 0.0 | 0.0 | 1.3 | 0.0 | 6.3 | 10.4 | 59.8 | 1.1 | 12.4 | 111.2 | 1000 | 1.0 |

TABLE 2-continued

Fatty acid profile of 90 putative mutants. Each of the colonies selected was grown to isolate its plasmid. Isolate plasmids were transformed into the RL08ara (ΔfadD) strain and grown in LB 0.4% glycerol and 20 μM IPTG (mutants M1-M10) and 1 mM IPTG (mutants M3, M4, and M11-M90).

| Mutant | # Residue Changes | Mutations | C8:0 (mg/L) | C10:0 (mg/L) | C10:1 (mg/L) | C12:0 (mg/L) | C12:1 (mg/L) | C14:0 (mg/L) | C14:1 (mg/L) | C16:0 (mg/L) | C16:1 (mg/L) | C18:0 (mg/L) | C18:1 (mg/L) | Total FFA (mg/L) | Induction Lev Tested (μM) | C8:0 Fold Increase Relative to CpFatB1.2 at Same Induction Level |
|---|---|---|---|---|---|---|---|---|---|---|---|---|---|---|---|---|
| CpFatB1.2-M81 | ND | ND | 8.5 | 0.0 | 0.4 | 0.0 | 1.2 | 0.0 | 5.0 | 3.2 | 72.0 | 1.6 | 8.3 | 100.1 | 1000 | 0.4 |
| CpFatB1.2-M82 | ND | ND | 11.3 | 0.0 | 0.6 | 0.0 | 1.8 | 0.0 | 4.9 | 6.4 | 71.8 | 1.6 | 15.2 | 113.6 | 1000 | 0.5 |
| CpFatB1.2-M83 | ND | ND | 18.8 | 0.0 | 1.2 | 0.0 | 2.6 | 0.0 | 5.6 | 4.4 | 69.2 | 1.5 | 14.6 | 117.8 | 1000 | 0.9 |
| CpFatB1.2-M84 | ND | ND | 9.2 | 0.0 | 0.4 | 0.0 | 1.2 | 0.0 | 4.6 | 2.4 | 66.2 | 1.5 | 7.4 | 93.0 | 1000 | 0.4 |
| CpFatB1.2-M85 | ND | ND | 9.4 | 0.0 | 0.5 | 0.0 | 1.4 | 0.0 | 4.6 | 5.0 | 69.1 | 1.6 | 10.3 | 101.8 | 1000 | 0.5 |
| CpFatB1.2-M86 | ND | ND | 16.2 | 0.0 | 1.0 | 0.0 | 2.1 | 0.0 | 5.3 | 6.6 | 71.7 | 1.4 | 16.1 | 120.3 | 1000 | 0.8 |
| CpFatB1.2-M87 | ND | ND | 27.2 | 0.0 | 1.6 | 0.0 | 1.9 | 0.0 | 4.9 | 2.7 | 65.6 | 1.6 | 9.4 | 114.9 | 1000 | 1.3 |
| CpFatB1.2-M88 | ND | ND | 12.0 | 0.0 | 0.7 | 0.0 | 1.8 | 0.0 | 5.1 | 6.7 | 74.5 | 1.6 | 16.4 | 118.8 | 1000 | 0.6 |
| CpFatB1.2-M89 | ND | ND | 8.6 | 0.0 | 0.4 | 0.0 | 1.2 | 0.0 | 4.3 | 2.4 | 63.9 | 1.5 | 7.7 | 90.0 | 1000 | 0.4 |
| CpFatB1.2-M90 | ND | ND | 11.1 | 0.0 | 0.6 | 0.0 | 1.5 | 0.0 | 5.1 | 5.2 | 72.8 | 1.5 | 12.7 | 110.6 | 1000 | 0.5 |

Production of Octanol Via Fatty Acid Biosynthesis

Expression of the CpFatB1.2 variants enables high flux to octanoic acid. Analogous to work with the BTE and conversion of dodecanoic acid to dodecanol (U.S. Pat. No. 9,708,630), we can co-express the CpFatB1.2 variants, an acyl-CoA synthetase, and a hybrid acyl-CoA reductase/aldehyde reductase to produce octanol. FadD, the native acyl-CoA synthetase used in the prior dodecanol work (U.S. Pat. No. 9,708,630) has poor activity against octanoic acid, so we replaced it with variants from other organisms. The best variant was FadD6 from *Mycobacterium tuberculosis* (SEQ ID NO:15 (nucleotide coding sequence) and SEQ ID NO:16 (protein sequence)). When these genes were co-expressed from plasmids in *E. coli* NHL13 (ΔfadD::fadD6 Δpta ΔpoxB ΔldhA), we observed up to 1.1 g/L titers from cultures grown in Clomberg media. The CpFatB1.2-M4 variant produced the most octanol (FIG. 16). Another suitable acyl-CoA synthetase with high activity on C8:0 is *Pseudomonas putida* PP0763 (SEQ ID NO:17 (nucleotide coding sequence) and SEQ ID NO:18 (protein sequence)).

Structural Modeling Insights

It has been experimentally shown that the CpFatB1.2-M4-287 mutant exhibits 15-fold higher specific activity in vivo (FIG. 11) relative to the natural parent enzyme. The CpFatB1.2-M4-287 enzyme variant the N28S, I65M double mutation and an 18-residue N-terminal truncation. To evaluate how these mutations impacted activity, we constructed a computational model of the mutant and parent enzymes. These were prepared by homology modeling using the published structure of *U. californica* UcFatB1 (PDB:5x04)[29] as a template. Unfortunately, we could not predict the structure of the N-terminus of CpFatB1.2-M4-287 as the 12 N-terminal residues of M4-287 were not conserved with the crystallized protein and no empirical 3D template structure could be identified with >30% sequence identity to this region. This means that our CpFatB1.2 model structure has a 30-residue N-terminus truncation relative to CpFatB1.2 and thus excluding the important N28S mutation and the truncation introduced in variant M4-287. On the other hand, the model was able to project where the I65M mutation resided relative to the active site (FIGS. 17A and 17B). Ile65 was positioned at one end of the acyl-binding crevice farthest from the crevice opening, where the catalytic residues line the periphery of the opening. We hypothesize that the bulkier side chain of the methionine is occluding the crevice end introducing steric clashes with the omega-1 acyl carbon of $C_{12}$-ACP, the preferred substrate of the template (PDB: 5x04) thioesterase. This residue is thus seemingly important for altering $C_8$-specificity, not activity. However, Mendonça et al.[30] show that mutations to amino acids connected to an active site residue by three or less noncovalent interactions can have a high impact on enzyme activity, a feat consistent with I65M according to the contact map for this residue (FIG. 17C).

The CpFatB1.2-M3 also exhibited elevated enzymatic activities (~4 folds higher than wild-type in vivo). Our CpFatB1.2 computational model with the 30 amino acid truncation at the N-terminus was used as the starting point to generate the variant model. Unlike CpFatB1.2-M4-287, we could capture the effects of both A59S and K296R mutations in this model. We hypothesize K296R has indirect and A59S has direct effects on enzyme activity based on the number of noncovalent bonds that connect these residues to one or more catalytic residues. Lys296 is a surface residue that has its side chain facing away from the acyl-binding pocket. However, a K296R mutation introduces a stable salt bridge interaction (~3.2 Å) between the positively charged N atom of Arg296 side chain and side chain O atom of Glu254 (FIGS. 18A-18C Prior to mutation the orientation of the Lys296 side chain did not result in a salt-bridge (~5.3 Å apart). Contact map (FIG. 18C) reveals Lys296 needs at least five noncovalent interactions to reach an active site residue which is shorter than that before the K296R mutation, but is less likely to have as much effect as I65M from CpFatB1.2-M4-287 (separated by 3 noncovalent interactions). However, CpFatB1.2-M3 accounts for its increase in activity by the A59S mutation which is adjacent to a Asp220 (a key catalytic residue). The side chain OH of Ser59 is linked to the backbone O atom of Asp220 (~4.5 Å) (FIG. 18C) The aliphatic methyl-side chain of Ala59 before mutation prevented any such polar contacts.

The CpFatB1.2-M4-287 and CpFatB1.2-M3 contact maps reveal the importance of Met69 (see FIGS. 17C and 18C) in connecting the mutated residues to the active site residues as it is the most connected node in the map. It is noteworthy that Met69 maintains these contact networks by mostly hydrophobic interactions higher up the cascade and polar interactions lower down. The polar interactions are controlled by the backbone O atom whereas the hydrophobic ones require the side chain C atoms. We hypothesize that Met69 is important for ensuring a connected contact map for both these mutants and altering M69 to a charged amino acid or a small-side chain hydrophobic residue can significantly reduce the enhanced activity of the CpFatB1 mutants.

Conclusions

Using a lipoic acid selection, we isolated a mutated octanoyl-ACP thioesterase capable of high rates of hydrolysis while maintaining >90% specificity towards $C_8$ acyl chains. A cell harboring a single chromosomal copy of this thioesterase gene is capable of achieving the same high level of production observed from plasmids expressing the parent enzyme. Under the conditions tested we demonstrated a more than 3-fold improvement over the highest reported octanoic acid titers in the literature. In light of the improved activity, we conclude that this work removes the thioesterase bottleneck for producing $C_8$ compounds in *E. coli*. Additional examples and discussion can be found in Hernandez Lozada et al.[42], which is incorporated herein by reference in its entirety. Future work can now focus on optimizing the flux from octanoic acid to desired 8-carbon products with other chemical functionalities.

REFERENCES

1. Biermann, U. et al. Oils and fats as renewable raw materials in chemistry. *Angew. Chemie—Int. Ed.* 50, 3854-3871 (2011).
2. Lennen, R. M. & Pfleger, B. F. Microbial production of fatty acid-derived fuels and chemicals. *Curr. Opin. Biotechnol.* 24, 1044-1053 (2013).
3. Voelker, T. A. & Davies, H. M. Alteration of the specificity and regulation of fatty acid synthesis of *Escherichia coli* by expression of a plant medium-chain acyl-acyl carrier protein thioesterase. *J. Bacteriol.* 176, 7320-7 (1994).
4. Graham, S. A., Hirsinger, F. & Robbelen, G. Fatty Acids of Cuphea (Lythraceae) Seed Lipids and Their Systematic Significance. *Am. J. Bot.* 68, 908 (1981).

5. Sarria, S., Kruyer, N. S. & Peralta-Yahya, P. Microbial synthesis of medium-chain chemicals from renewables. *Nat. Biotechnol.* 35, 1158-1166 (2017).
6. Lennen, R. M. & Pfleger, B. F. Engineering Escherichia coli to synthesize free fatty acids. *Trends Biotechnol.* 30, 659-667 (2012).
7. Pfleger, B. F., Gossing, M. & Nielsen, J. Metabolic engineering strategies for microbial synthesis of oleochemicals. *Metab. Eng.* 29, 1-11 (2015).
8. Cantu, D. C., Chen, Y., Lemons, M. L. & Reilly, P. J. ThYme: a database for thioester-active enzymes. *Nucleic Acids Res.* 39, D342-6 (2011).
9. Grisewood, M. J. et al. Computational Redesign of Acyl-ACP Thioesterase with Improved Selectivity toward Medium-Chain-Length Fatty Acids. *ACS Catal.* 3837-3849 (2017). doi:10.1021/acscatal.7b00408
10. Rupilius, W. & Ahmad, S. Palm oil and palm kernel oil as raw materials for basic oleochemicals and biodiesel. *Eur. J. Lipid Sci. Technol.* 109, 433-439 (2007).
11. Salimon, J., Salih, N. & Yousif, E. Industrial development and applications of plant oils and their biobased oleochemicals. *Arab. J. Chem.* 5, 135-145 (2012).
12. Benning, C. Mechanisms of lipid transport involved in organelle biogenesis in plant cells. *Annu. Rev. Cell Dev. Biol.* 25, 71-91 (2009).
13. Lennen, R. M., Braden, D. J., West, R. M., Dumesic, J. A. & Pfleger, B. F. A process for microbial hydrocarbon synthesis: Overproduction of fatty acids in Escherichia coli and catalytic conversion to alkanes. *Biotechnol. Bioeng.* 106, 193-202 (2010).
14. Cho, H. & Cronan, J. E. Defective export of a periplasmic enzyme disrupts regulation of fatty acid synthesis. *J. Biol. Chem.* 270, 4216-9 (1995).
15. Torella, J. P. et al. Tailored fatty acid synthesis via dynamic control of fatty acid elongation. *Proc. Natl. Acad. Sci. U.S.A.* 110, 11290-5 (2013).
16. Zhang, F. et al. Enhancing fatty acid production by the expression of the regulatory transcription factor FadR. *Metab. Eng.* 14, 653-60 (2012).
17. Jing, F., Zhao, L., Yandeau-Nelson, M. D. & Nikolau, B. J. Two distinct domains contribute to the substrate acyl chain length selectivity of plant acyl-ACP thioesterase. *Nat. Commun.* 9, 860 (2018).
18. Zhang, F., Carothers, J. M. & Keasling, J. D. Design of a dynamic sensor-regulator system for production of chemicals and fuels derived from fatty acids. *Nat. Biotechnol.* 30, 354-359 (2012).
19. Mukherjee, K., Bhattacharyya, S. & Peralta-Yahya, P. GPCR-Based Chemical Biosensors for Medium-Chain Fatty Acids. *ACS Synth. Biol.* 4, 1261-1269 (2015).
20. Cronan, J. E., Zhao, X. & Jiang, Y. *Function, Attachment and Synthesis of Lipoic Acid in Escherichia coli.* Advances in Microbial Physiology 50, (Elsevier Masson S A S, 2005).
21. Zhao, X., Miller, J. R., Jiang, Y., Marietta, M. A. & Cronan, J. E. Assembly of the Covalent Linkage between Lipoic Acid and Its Cognate Enzymes. Chem. Biol. 10, 1293-1302 (2003).
22. Dehesh, K., Edwards, P., Hayes, T., Cranmer, A. M. & Fillatti, J. Two novel thioesterases are key determinants of the bimodal distribution of acyl chain length of Cuphea palustris seed oil. *Plant Physiol.* 110, 203-210 (1996).
23. Jing, F. et al. Phylogenetic and experimental characterization of an acyl-ACP thioesterase family reveals significant diversity in enzymatic specificity and activity. *BMC Biochem.* 12, 44 (2011).
24. Neidhardt, F. C., Bloch, P. L. & Smith, D. F. Culture Medium for Enterobacteria. *J. Bacteriol.* 119, 736-747 (1974).
25. Kim, S., Clomburg, J. M. & Gonzalez, R. Synthesis of medium-chain length (C6-C10) fuels and chemicals via β-oxidation reversal in Escherichia coli. *J. Ind. Microbiol. Biotechnol.* 42, 465-475 (2015).
26. Beld, J., Finzel, K. & Burkart, M. D. Versatility of acyl-acyl carrier protein synthetases. *Chem. Biol.* 21, 1293-1299 (2014).
27. Royce, L. A., Liu, P., Stebbins, M. J., Hanson, B. C. & Jarboe, L. R. The damaging effects of short chain fatty acids on Escherichia coli membranes. *Appl. Microbiol. Biotechnol.* 97, 8317-27 (2013).
28. Royce, L. A. et al. Evolution for exogenous octanoic acid tolerance improves carboxylic acid production and membrane integrity. *Metab. Eng.* 1-9 (2015). doi:10.1016/j.ymben.2015.03.014
29. Feng, Y. et al. Structural Insight into Acyl-ACP Thioesterase toward Substrate Specificity Design. *ACS Chem. Biol.* 12, 2830-2836 (2017).
30. Mendonca, L. M. F. & Marana, S. R. Single mutations outside the active site affect the substrate specificity in a β-glycosidase. *Biochim. Biophys. Acta—Proteins Proteomics* 1814, 1616-1623 (2011).
31. Lu, Z., Wang, Q., Jiang, S., Zhang, G. & Ma, Y. Truncation of the unique N-terminal domain improved the thermos-stability and specific activity of alkaline α-amylase Amy703. *Sci. Rep.* 6, 1-10 (2016).
32. Li, Y. et al. Metabolic engineering of Escherichia coli using CRISPR-Cas9 meditated genome editing. *Metab. Eng.* 31, 13-21 (2015).
33. Datsenko, K. A. & Wanner, B. L. One-step inactivation of chromosomal genes in Escherichia coli K-12 using PCR products. *Proc. Natl. Acad. Sci. U.S.A.* 97, 6640-6645 (2000).
34. Gibson, D. G. et al. Enzymatic assembly of DNA molecules up to several hundred kilobases. *Nat. Methods* 6, 343-5 (2009).
35. Lennen, R. M. & Pfleger, B. F. Modulating Membrane Composition Alters Free Fatty Acid Tolerance in Escherichia coli. *PLoS One* 8, e54031 (2013).
36. Youngquist, J. T., Rose, J. P. & Pfleger, B. F. Free fatty acid production in Escherichia coli under phosphate-limited conditions. *Appl. Microbiol. Biotechnol.* 97, 5149-5159 (2013).
37. Pantazes, R. J., Grisewood, M. J., Li, T., Gifford, N. P. & Maranas, C. D. The Iterative Protein Redesign and Optimization (IPRO) suite of programs. *J. Comput. Chem.* 36, 251-263 (2015).
38. Agnew, D. E., Stevermer, A. K., Youngquist, J. T. & Pfleger, B. F. Engineering Escherichia coli for production of $C_{12}$-$C_{14}$ polyhydroxyalkanoate from glucose. *Metab. Eng.* 14, 705-13 (2012).
39. Youngquist, J. T. et al. Production of medium chain length fatty alcohols from glucose in Escherichia coli. *Metab. Eng.* 20, 177-186 (2013).
40. Amann, E., Ochs, B. & Abel, K. J. Tightly regulated tac promoter vectors useful for the expression of unfused and fused proteins in Escherichia coli. *Gene* 69, 301-315 (1988).
41. Guzman, L.-M., Belin, D., Carson, M. J. & Beckwith, J. Tight Regulation, Modulation, and High-Level Expression by Vectors Containing the Arabinose P BAD Promoter. *J. Bacteriol.* 177, 4121-4130 (1995).
42. Hernández Lozada N J, Lai R Y, Simmons T R, Thomas K A, Chowdhury R, Maranas C D, Pfleger B F. Highly Active C(8)-Acyl-ACP Thioesterase Variant Isolated by a Synthetic Selection Strategy. *ACS Synth Biol.* 2018 Sep. 21;7(9):2205-2215.

What is claimed is:

1. An unnatural, mutated protein comprising an amino acid sequence at least about 80% identical to positions 19-317 of SEQ ID NO:4, wherein:
   the amino acid sequence comprises:
      a residue other than asparagine at a position corresponding to position 28 of SEQ ID NO:4; and
      a residue other than isoleucine at a position corresponding to position 65 of SEQ ID NO:4;
   the protein lacks an N-terminal portion having an amino acid sequence identical to positions 1-18 of SEQ ID NO:4; and
   the protein exhibits thioesterase activity.

2. The protein of claim 1, wherein the amino acid sequence at least about 80% identical to positions 19-317 of SEQ ID NO:4 comprises:
   a serine, cysteine, threonine, tyrosine, or glutamine at the position corresponding to position 28 of SEQ ID NO:4; and
   a methionine, alanine, leucine, phenylalanine, valine, proline, or glycine at the position corresponding to position 65 of SEQ ID NO:4.

3. The protein of claim 2, wherein the protein comprises, relative to a protein consisting of an amino acid sequence of SEQ ID NO:4, an N-terminal truncation of positions 1-18 of SEQ ID NO:4.

4. The protein of claim 1, wherein the amino acid sequence at least about 80% identical to positions 19-317 of SEQ ID NO:4 comprises:
   a serine at the position corresponding to position 28 of SEQ ID NO:4; and a methionine at the position corresponding to position 65 of SEQ ID NO:4.

5. The protein of claim 4, wherein the protein comprises, relative to a protein consisting of an amino acid sequence of SEQ ID NO:4, an N-terminal truncation of positions 1-18 of SEQ ID NO:4.

6. The protein of claim 1, wherein the protein comprises, relative to a protein consisting of an amino acid sequence of SEQ ID NO:4, an N-terminal truncation of positions 1-18 of SEQ ID NO:4.

7. The protein of claim 1, wherein the amino acid sequence at least about 80% identical to positions 19-317 of SEQ ID NO:4 is an amino acid sequence at least about 85% identical to positions 19-317 of SEQ ID NO:4.

8. The protein of claim 7, wherein the amino acid sequence at least about 85% identical to positions 19-317 of SEQ ID NO:4 comprises:
   a serine, cysteine, threonine, tyrosine, or glutamine at the position corresponding to position 28 of SEQ ID NO:4; and
   a methionine, alanine, leucine, phenylalanine, valine, proline, or glycine at the position corresponding to position 65 of SEQ ID NO:4.

9. The protein of claim 8, wherein the protein comprises, relative to a protein consisting of an amino acid sequence of SEQ ID NO:4, an N-terminal truncation of positions 1-18 of SEQ ID NO:4.

10. The protein of claim 7, wherein the amino acid sequence at least about 85% identical to positions 19-317 of SEQ ID NO:4 comprises:
    a serine at the position corresponding to position 28 of SEQ ID NO:4; and
    a methionine at the position corresponding to position 65 of SEQ ID NO:4.

11. The protein of claim 10, wherein the protein comprises, relative to a protein consisting of an amino acid sequence of SEQ ID NO:4, an N-terminal truncation of positions 1-18 of SEQ ID NO:4.

12. The protein of claim 7, wherein the protein comprises, relative to a protein consisting of an amino acid sequence of SEQ ID NO:4, an N-terminal truncation of positions 1-18 of SEQ ID NO:4.

13. The protein of claim 1, wherein the amino acid sequence at least about 80% identical to positions 19-317 of SEQ ID NO:4 is an amino acid sequence at least about 90% identical to positions 19-317 of SEQ ID NO:4.

14. The protein of claim 13, wherein the amino acid sequence at least about 90% identical to positions 19-317 of SEQ ID NO:4 comprises:
    a serine, cysteine, threonine, tyrosine, or glutamine at the position corresponding to position 28 of SEQ ID NO:4; and
    a methionine, alanine, leucine, phenylalanine, valine, proline, or glycine at the position corresponding to position 65 of SEQ ID NO:4.

15. The protein of claim 14, wherein the protein comprises, relative to a protein consisting of an amino acid sequence of SEQ ID NO:4, an N-terminal truncation of positions 1-18 of SEQ ID NO:4.

16. The protein of claim 13, wherein the amino acid sequence at least about 90% identical to positions 19-317 of SEQ ID NO:4 comprises:
    a serine at the position corresponding to position 28 of SEQ ID NO:4; and
    a methionine at the position corresponding to position 65 of SEQ ID NO:4.

17. The protein of claim 16, wherein the protein comprises, relative to a protein consisting of an amino acid sequence of SEQ ID NO:4, an N-terminal truncation of positions 1-18 of SEQ ID NO:4.

18. The protein of claim 13, wherein the protein comprises, relative to a protein consisting of an amino acid sequence of SEQ ID NO:4, an N-terminal truncation of positions 1-18 of SEQ ID NO:4.

19. The protein of claim 1, wherein the amino acid sequence at least about 80% identical to positions 19-317 of SEQ ID NO:4 is an amino acid sequence at least about 95% identical to positions 19-317 of SEQ ID NO:4.

20. The protein of claim 19, wherein the amino acid sequence at least about 95% identical to positions 19-317 of SEQ ID NO:4 comprises:
    a serine, cysteine, threonine, tyrosine, or glutamine at the position corresponding to position 28 of SEQ ID NO:4; and
    a methionine, alanine, leucine, phenylalanine, valine, proline, or glycine at the position corresponding to position 65 of SEQ ID NO:4.

21. The protein of claim 20, wherein the protein comprises, relative to a protein consisting of an amino acid sequence of SEQ ID NO:4, an N-terminal truncation of positions 1-18 of SEQ ID NO:4.

22. The protein of claim 19, wherein the amino acid sequence at least about 95% identical to positions 19-317 of SEQ ID NO:4 comprises:
    a serine at the position corresponding to position 28 of SEQ ID NO:4; and
    a methionine at the position corresponding to position 65 of SEQ ID NO:4.

23. The protein of claim 22, wherein the protein comprises, relative to a protein consisting of an amino acid sequence of SEQ ID NO:4, an N-terminal truncation of positions 1-18 of SEQ ID NO:4.

24. The protein of claim 19, wherein the protein comprises, relative to a protein consisting of an amino acid sequence of SEQ ID NO:4, an N-terminal truncation of positions 1-18 of SEQ ID NO:4.

* * * * *